(12) United States Patent
Dang et al.

(10) Patent No.: US 12,201,801 B2
(45) Date of Patent: Jan. 21, 2025

(54) TUBING HAVING VISUAL MARKERS FOR VISUALIZATION OF MEDIA THEREIN

(71) Applicant: Eli Lilly and Company, Indianapolis, IN (US)

(72) Inventors: Xiangnan Dang, Sharon, MA (US); Daniel Morris Hartmann, Arlington, MA (US); Michael David Sanchez, Alexandria, VA (US)

(73) Assignee: Eli Lilly and Company, Indianapolis, IN (US)

( * ) Notice: Subject to any disclaimer, the term of this patent is extended or adjusted under 35 U.S.C. 154(b) by 1064 days.

(21) Appl. No.: 16/652,567

(22) PCT Filed: Sep. 27, 2018

(86) PCT No.: PCT/US2018/053022
§ 371 (c)(1),
(2) Date: Mar. 31, 2020

(87) PCT Pub. No.: WO2019/070486
PCT Pub. Date: Apr. 11, 2019

(65) Prior Publication Data
US 2020/0238068 A1     Jul. 30, 2020

Related U.S. Application Data

(60) Provisional application No. 62/663,305, filed on Apr. 27, 2018, provisional application No. 62/567,890, filed on Oct. 4, 2017.

(51) Int. Cl.
*A61M 39/08*     (2006.01)
*A61M 5/168*     (2006.01)
*A61M 25/00*     (2006.01)

(52) U.S. Cl.
CPC ............ *A61M 39/08* (2013.01); *A61M 5/168* (2013.01); *A61M 25/0012* (2013.01);
(Continued)

(58) Field of Classification Search
CPC ...... A61M 2205/585; A61M 2205/583; A61M 2205/3306; A61M 5/365; A61M 2025/006; A61M 2025/0008
See application file for complete search history.

(56) References Cited

U.S. PATENT DOCUMENTS

| | | |
|---|---|---|
| 4,452,251 A | 6/1984 | Heilman |
| 4,764,806 A | 8/1988 | Altman |

(Continued)

FOREIGN PATENT DOCUMENTS

| | | |
|---|---|---|
| DE | 4336520 | 4/1995 |
| DE | 10147597 | 4/2003 |

(Continued)

OTHER PUBLICATIONS

International Search Report of the International Searching Authority pertaining to International Application No. PCT/US2018/053022; Date of Mailing: Dec. 19, 2018; 6 pages.

(Continued)

*Primary Examiner* — Scott J Medway
*Assistant Examiner* — Anh Bui
(74) *Attorney, Agent, or Firm* — Jonathan C. Anderson

(57) ABSTRACT

A transparent tubing is provided comprising a longitudinal axis having a center; an inner circumferential surface defining a fluid pathway therethrough for delivering a first medium having a first index of refraction m; an outer circumferential surface; at least one visual marker; and, at least one integrated lens disposed opposite from the at least one visual marker, the at least one integrated lens configured to direct light from the at least one visual marker for (Continued)

detecting a presence or an absence in the fluid pathway of a second medium having a second index of refraction $n_2$, where n2 is different from the first index of refraction $n_1$. A method of making transparent tubing having at least one integrated lens is also provided.

27 Claims, 42 Drawing Sheets

(52) U.S. Cl.
CPC . *A61M 25/0043* (2013.01); *A61M 2025/0008* (2013.01); *A61M 2025/006* (2013.01); *A61M 2205/3306* (2013.01); *A61M 2205/583* (2013.01); *A61M 2207/00* (2013.01)

(56) References Cited

U.S. PATENT DOCUMENTS

| | | | |
|---|---|---|---|
| 5,030,207 A * | 7/1991 | Mersch | A61B 5/150389 604/168.01 |
| 5,672,887 A | 9/1997 | Shaw et al. | |
| 6,110,153 A | 8/2000 | Davis et al. | |
| 8,398,590 B2 | 3/2013 | Sternberg et al. | |
| 8,721,596 B2 | 5/2014 | Trocki et al. | |
| 9,033,923 B2 | 5/2015 | Hartman et al. | |
| 2006/0116660 A1 * | 6/2006 | Cawley | A61M 39/12 604/93.01 |
| 2011/0071480 A1 * | 3/2011 | Katerkamp | A61M 25/0693 604/272 |
| 2011/0092888 A1 * | 4/2011 | Gerg | A61F 9/00736 604/22 |
| 2012/0268741 A1 * | 10/2012 | Pommereau | G01F 23/2921 356/343 |

FOREIGN PATENT DOCUMENTS

| | | |
|---|---|---|
| FR | 2660755 | 10/1991 |
| WO | 2009027896 | 3/2009 |

OTHER PUBLICATIONS

Written Opinion of the International Searching Authority pertaining to International Application No. PCT/US2018/053022; Date of Mailing: Dec. 19, 2018; 9 pages.

* cited by examiner

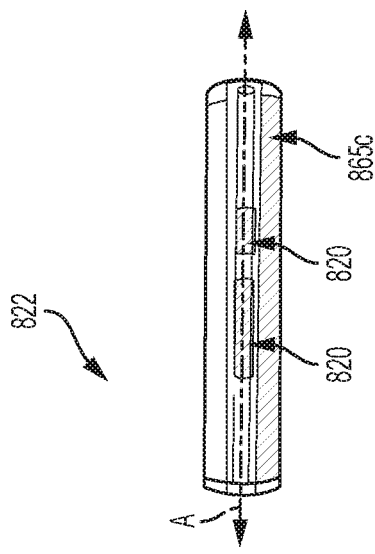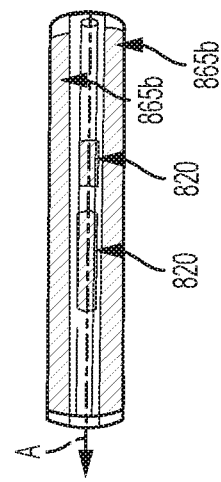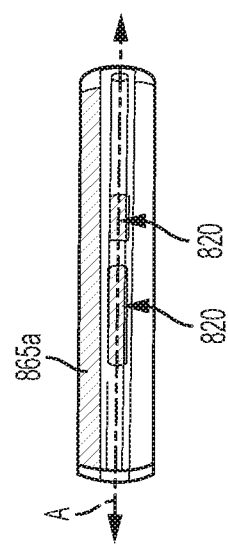

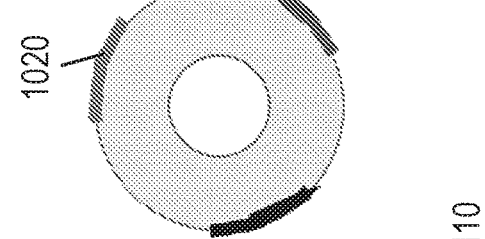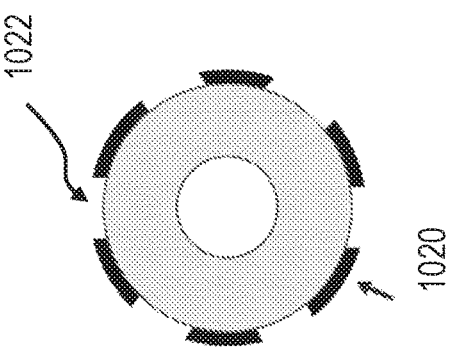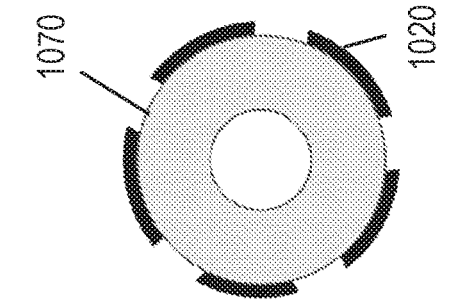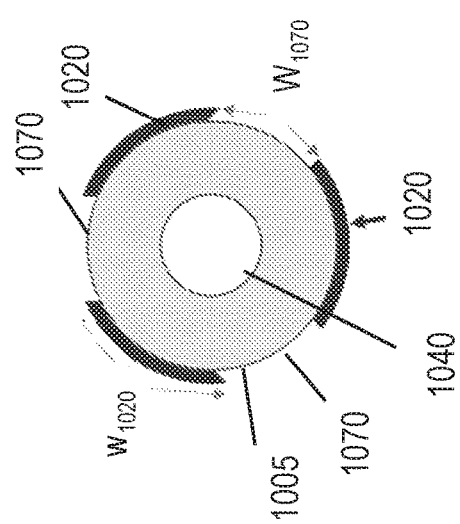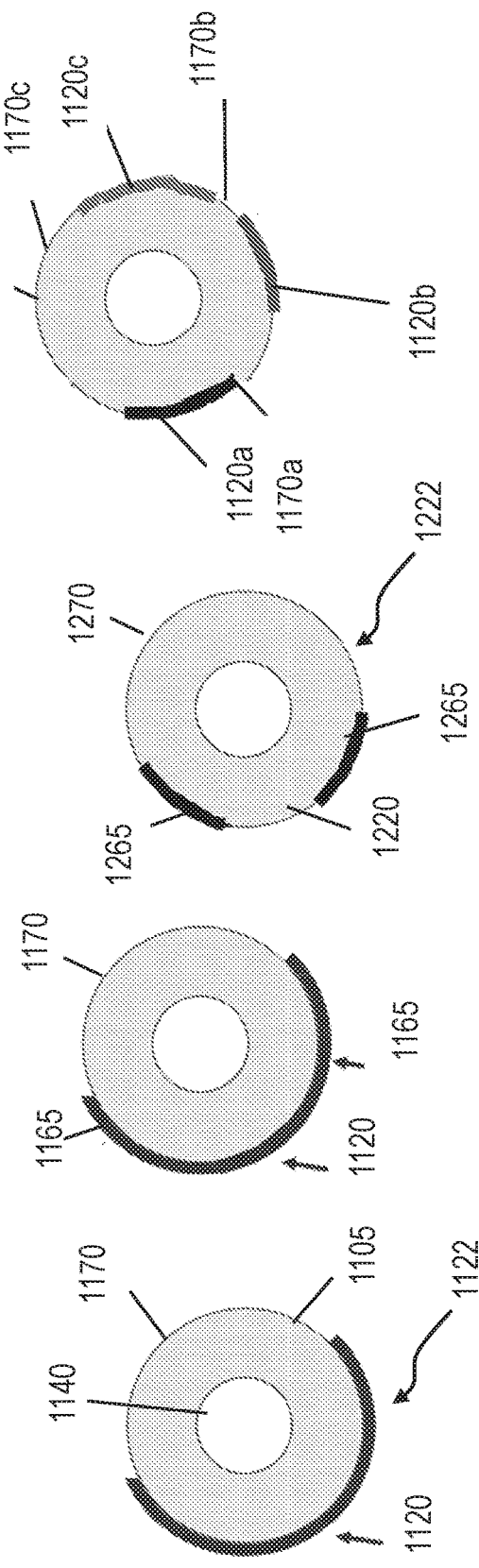

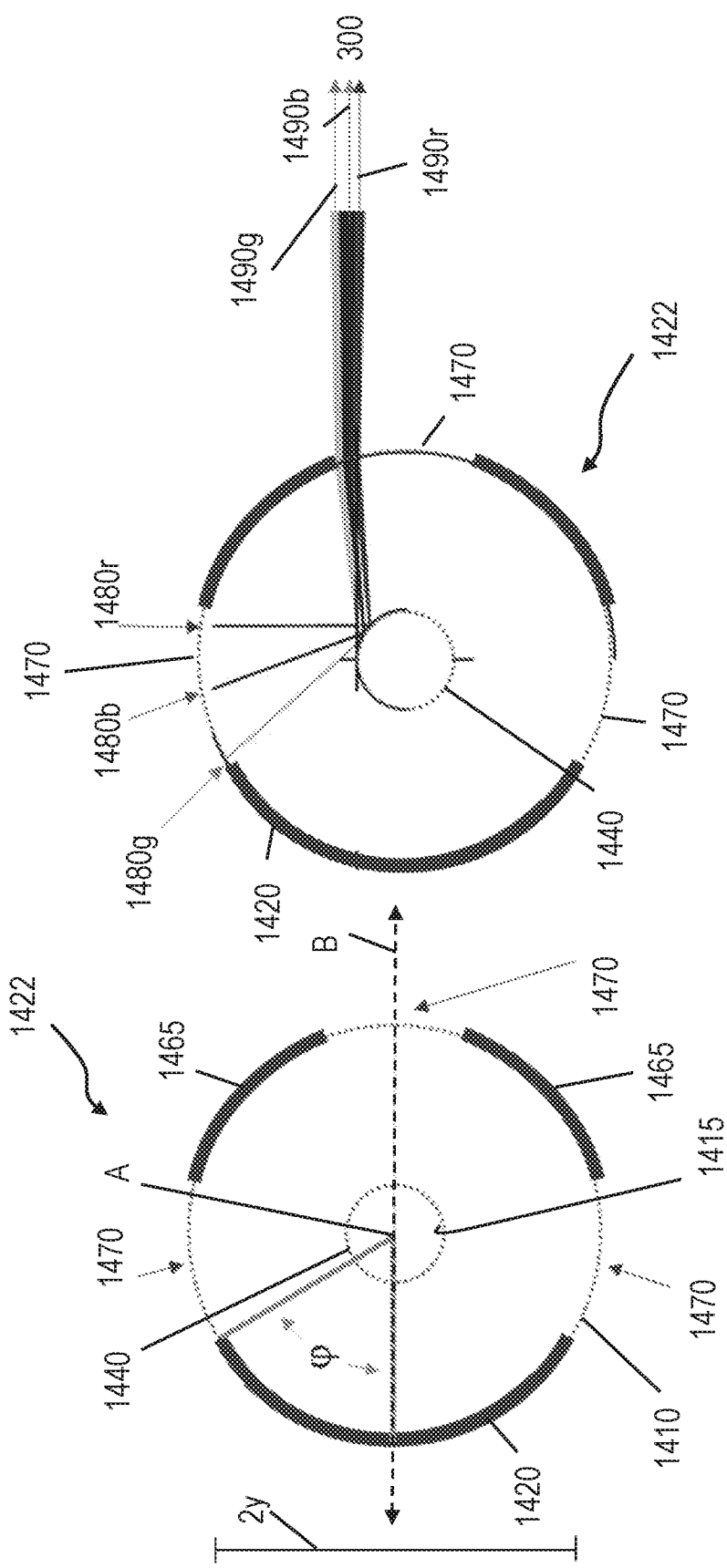

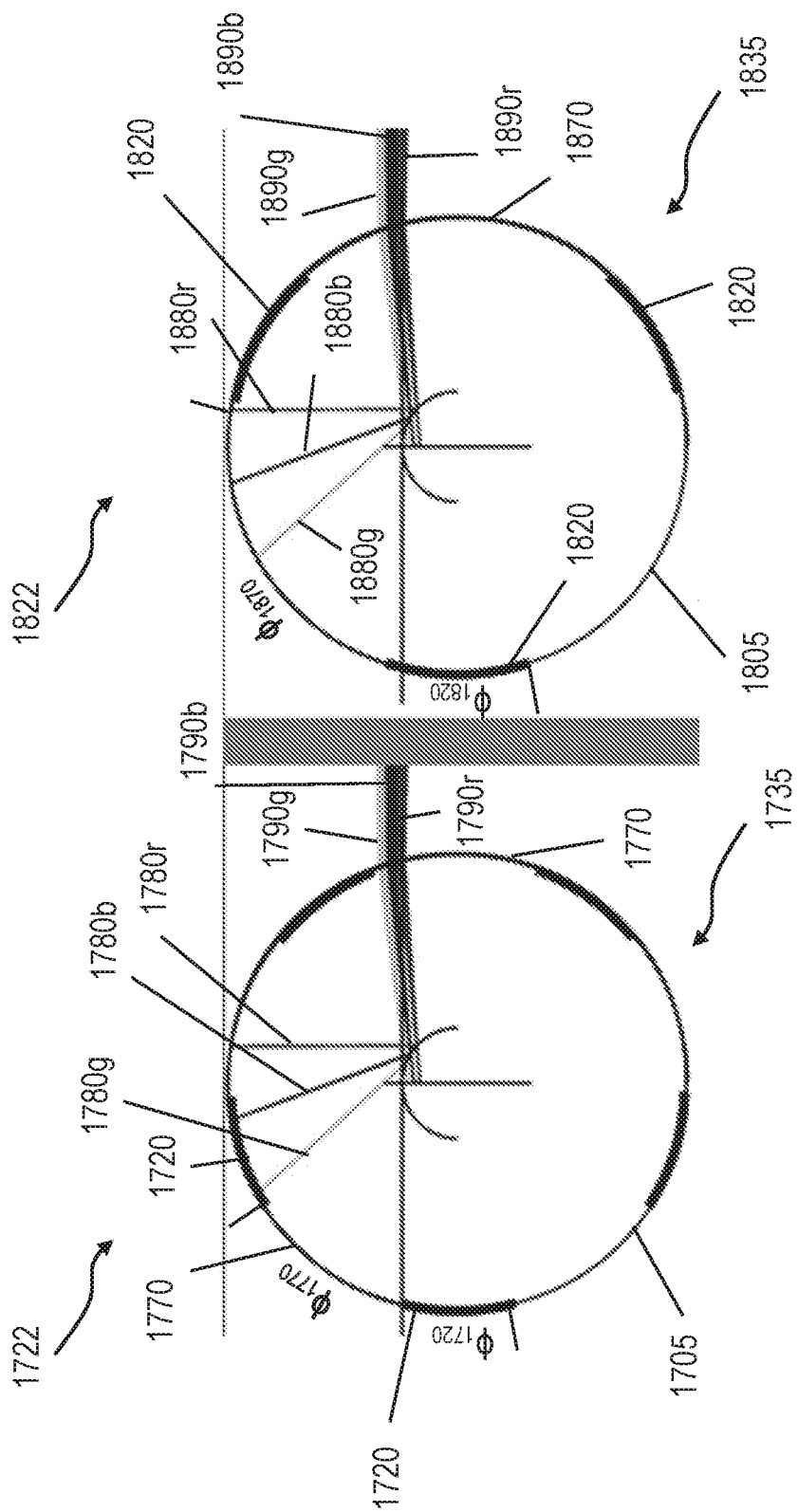

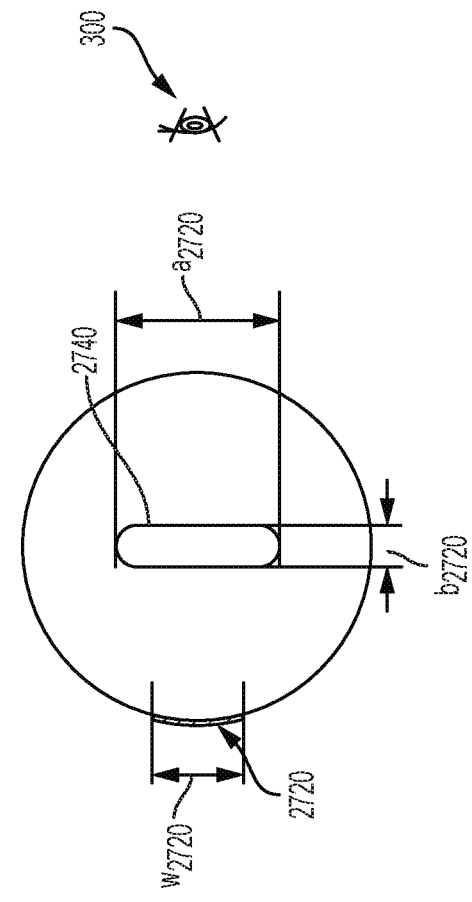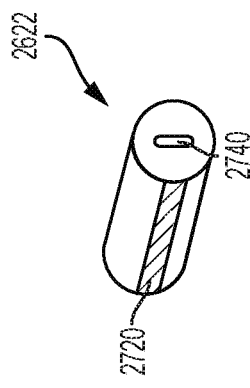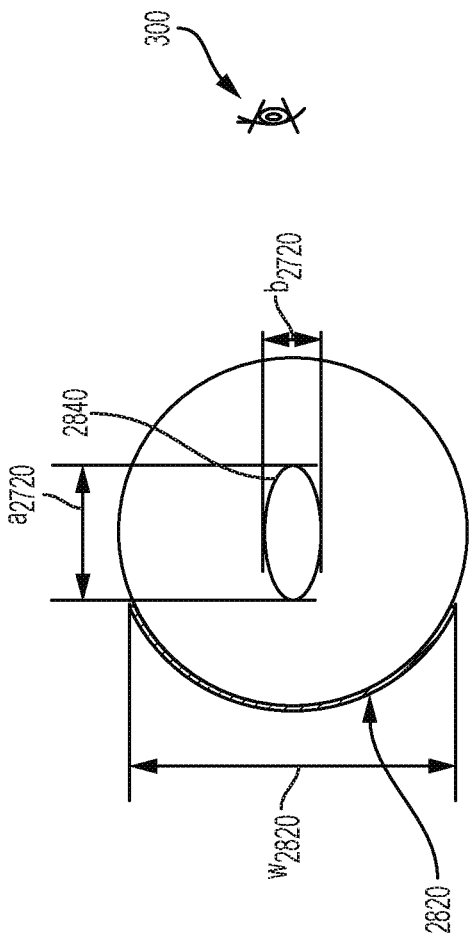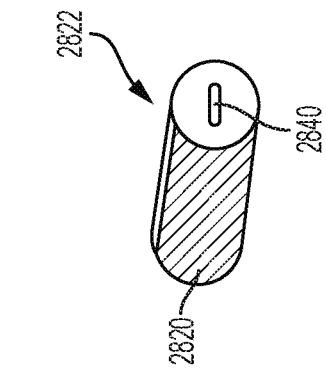
FIG. 65
FIG. 66
FIG. 67
FIG. 68

TUBING HAVING VISUAL MARKERS FOR VISUALIZATION OF MEDIA THEREIN

CROSS REFERENCE TO RELATED APPLICATIONS

This application is a National Stage of International Application No. PCT/US2018/053022, filed Sep. 27, 2018, which claims priority to U.S. Provisional Patent Application Ser. No. 62/567,890, filed Oct. 4, 2017 and entitled TUBING HAVING INTEGRATED LENSES FOR VISUALIZATION OF MEDIA THEREIN, and U.S. Provisional Patent Application Ser. No. 62/663,305, filed Apr. 27, 2018 and entitled TUBING HAVING VISUAL MARKERS FOR VISUALIZATION OF MEDIA THEREIN, the entire disclosures of which are hereby expressly incorporated by reference herein.

FIELD OF THE DISCLOSURE

The present disclosure relates to a device for fluid delivery, specifically for parenteral drug delivery, and more specifically for continuous subcutaneous insulin infusion (CSII).

BACKGROUND OF THE DISCLOSURE

Transparent tubing is used for many applications including parenteral drug delivery. An example is tubing used for continuous subcutaneous insulin infusion (CSII). During use, the insulin infusion set (IIS) tubing should be full of an insulin formulation or another suitable drug product and free of any air bubbles. Such air bubbles may cause increased compliance and resistance to flow through the IIS device. Also, such air bubbles may be delivered to the patient in place of the desired drug product, meaning that the actual dose of the desired drug product would be less than the expected dose. For these reasons, IIS devices are primed with the drug product and inspected for air bubbles prior to use. Visual inspection of the tubing may also be conducted during use if inefficacious drug delivery is suspected—as when a person experiences unexpected hyperglycemic events. However, it is difficult to visualize air bubbles in existing IIS devices, especially when the drug product is transparent.

SUMMARY

The present disclosure provides a transparent tubing, the tubing comprising a longitudinal axis having a center; an inner circumferential surface defining a fluid pathway therethrough for delivering a first medium having a first index of refraction $n_1$; an outer circumferential surface; at least one visual marker; and, at least one integrated lens disposed opposite from the at least one visual marker, the at least one integrated lens configured to direct light from the at least one visual marker for detecting a presence or an absence in the fluid pathway of a second medium having a second index of refraction $n_2$, where $n_2$ is different from the first index of refraction $n_1$.

According to an embodiment of the present disclosure, the inner circumferential surface is disposed at a first radial distance ($r_1$) from the center; and, the outer circumferential surface is disposed at a second radial distance ($r_2$) from the center.

According to an embodiment of the present disclosure, the at least one integrated lens further comprises an exterior surface including at least one point coincident with the outer circumferential surface, wherein the exterior surface of the at least one integrated lens protrudes from the outer circumferential surface, and wherein the exterior surface of the lens includes at least one point at a third radial distance ($r_3$) from the center, wherein the third radial distance ($r_3$) is greater than the second radial distance ($r_2$). In some embodiments of the present disclosure, the exterior surface of the lens is convex.

According to an embodiment of the present disclosure, the outer circumferential surface has a first radius of curvature ($R_1$) and the exterior surface of the lens has a second radius of curvature ($R_2$), wherein the first radius of curvature ($R_1$) and the second radius of curvature ($R_2$) are different.

According to an embodiment of the present disclosure, the outer circumferential surface has a first radius of curvature ($R_1$) and the exterior surface of the lens has a second radius of curvature ($R_2$), wherein the first radius of curvature ($R_1$) is greater than the second radius of curvature ($R_2$).

According to an embodiment of the present disclosure, the outer circumferential surface has a first radius curvature ($R_1$) and the exterior surface of the lens has a plurality of radii of curvature ($R_{2-5}$).

According to an embodiment of the present disclosure, the outer circumferential surface and the exterior surface of the lens meet at first and second edges.

According to an embodiment of the present disclosure, the outer circumferential surface is connected to the exterior surface of the lens by first and second planar faces.

According to an embodiment of the present disclosure, the first planar face is inclined at a first slope and the second planar face is inclined at a second slope, wherein the first slope is opposite the second slope.

According to an embodiment of the present disclosure, the integrated lens includes an exterior surface connected to the outer circumferential surface by first and second coplanar faces, wherein the exterior surface of the lens includes at least one point at a third radial distance ($r_3$) from the center, wherein the third radial distance ($r_3$) is greater than the first radial distance ($r_1$).

According to an embodiment of the present disclosure, the integrated lens is aspheric.

According to an embodiment of the present disclosure, the transparent tubing is a material chosen from at least one of polypropylene, polyvinyl chloride, polyethylene, polyurethane, silicone, and glass.

According to an embodiment of the present disclosure, the transparent tubing including the integrated lens is formed in a single extrusion process.

According to an embodiment of the present disclosure, the integrated lens comprises a plurality of plano-convex lenses disposed linearly and parallel to the longitudinal axis.

According to an embodiment of the present disclosure, the integrated lens is an elongated cylindrical lens disposed parallel to the longitudinal axis.

According to an embodiment of the present disclosure, the integrated lens further includes an interior surface protruding from the inner circumferential surface at a fourth radial distance ($r_4$) from the center, wherein the fourth radial distance ($r_4$) is less than the first radial distance ($r_1$).

According to an embodiment of the present disclosure, the at least one integrated lens has a third index of refraction $n_3$, wherein $n_3$ is different from $n_1$ and $n_2$.

According to an embodiment of the present disclosure, the transparent tubing further comprises a wall disposed between the inner surface and the outer surface, the wall having a fourth index of refraction $n_4$, wherein $n_4$ and $n_3$ are the same or different.

According to an embodiment of the present disclosure, the wall is made of glass or plastic.

According to an embodiment of the present disclosure, the inner surface has a conic section cross-sectional shape.

According to an embodiment of the present disclosure, the inner surface has a polygonal cross-sectional shape.

According to an embodiment of the present disclosure, the transparent tubing is a transparent infusion-set tubing for an insulin pump.

According to another embodiment of the present disclosure, a transparent tubing is provided, the transparent tubing comprising a longitudinal axis having a center; an inner circumferential surface at a first radial distance ($r_1$) from the center, the inner circumferential surface defining a fluid pathway therethrough for delivering a first medium, the first medium having a first index of refraction $n_1$; an outer circumferential surface at a second radial distance ($r_2$) from the center; and, at least one integrated lens configured to direct light from the fluid pathway to detect a presence or an absence of a second medium, the second medium having a second index of refraction $n_2$, where $n_2$ is different from $n_1$.

According to yet another embodiment of the present disclosure, a method of making a transparent tubing is provided. The method comprises selecting a transparent material; forming the transparent material into an elongated tubing having a fluid pathway and a longitudinal axis therethrough for delivering a first medium having a first index of refraction $n_1$, the elongated tubing including at least one visual marker; and, integrating at least one lens in the elongated tubing, the at least one lens disposed opposite from the at least one visual marker, the lens configured to direct light from the at least one visual marker for detecting a presence or an absence of a second medium in the fluid pathway, the second medium having a second index of refraction $n_2$, where $n_2$ is different from the first index of refraction $n_1$.

According to an embodiment of the present disclosure, the transparent material is chosen from at least one of polypropylene, polyvinyl chloride, polyethylene, polyurethane, silicone, and glass.

According to an embodiment of the present disclosure, forming the material includes coextruding the elongated tubing and the lens. In some embodiments of the method, integrating the lens includes molding. In some embodiments of the method, the lens is discontinuously disposed with respect to the elongated tubing.

According to another embodiment of the present disclosure, a tubing is provided comprising an inner circumferential surface defining a lumen configured to deliver a first medium having a first index of refraction $n_1$, an outer circumferential surface having at least one visual marker, the outer circumferential surface and the inner circumferential surface defining a tubing wall having a second index of refraction $n_2$ different from the first index of refraction $n_1$; and at least one window opposite the visual marker for transmitting an image of the visual marker, the image configured to distinguish the first medium in the lumen from air in the lumen.

According to an embodiment of the present disclosure, a magnification of the image differs when the lumen contains the first medium compared to when the lumen contains air. For example, the image may be more magnified when the lumen contains the first medium than when the lumen contains air.

According to an embodiment of the present disclosure, light reflections at an interface between the inner circumferential surface and the lumen differ when the lumen contains the first medium compared to when the lumen contains air.

According to an embodiment of the present disclosure, a translation of the image differs when the lumen contains the first medium compared to when the lumen contains air.

According to another embodiment of the present disclosure, a tubing is provided comprising an inner circumferential surface defining a lumen having a radius $R_L$, the lumen being configured to deliver a first medium having a first index of refraction $n_1$; an outer circumferential surface, the outer circumferential surface and the inner circumferential surface defining a tubing wall having a second index of refraction $n_2$; and at least one visual marker at the outer circumferential surface, the visual marker having a width from about $0.25R_L$ to about $0.90R_L$.

According to another embodiment of the present disclosure, a tubing is provided comprising at least one lumen; a tubing wall surrounding the at least one lumen, the tubing wall being at least partially transparent and having an outer surface; a pattern at the outer surface, the pattern including: at least one visual marker; at least one window opposite the visual marker for transmitting an image of the visual marker; and at least one mask configured to inhibit secondary images from being transmitted through the at least one window.

According to an embodiment of the present disclosure, the tubing further comprises a second window positioned between the at least one visual marker and the at least one mask.

According to an embodiment of the present disclosure, the tubing further comprises a second visual marker and a third visual marker, wherein the visual markers have the same angular extent.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein:

FIGS. 23-25 are top views of a tubing of the present disclosure showing secondary optical imaging effects as a function of rotating the tubing slightly with respect to longitudinal axis A, wherein FIG. 23 and FIG. 25 are rotated negatively and positively off axis as compared with FIG. 24;

FIGS. 29-32 are cross-sectional views of tubing of the present disclosure having radially symmetric patterns, wherein FIG. 29 shows a pattern where the number of markers $N_m=3$, FIG. 30 shows a pattern where the number of markers $N_m=5$, FIG. 31 shows a pattern where the number of markers $N_m=6$, and FIG. 32 shows a pattern where the number of markers $N_m=3$ and the markers are each of a different color as in FIG. 28;

FIGS. 33-36 are cross-sectional views of tubing of the present disclosure having radially asymmetric patterns, wherein in FIG. 33 shows a pattern having one marker and one window, FIG. 34 shows a pattern having one visual marker, two masking markers, and one window, FIG. 35 shows a pattern having two masking markers, a visual marker, and a window, and FIG. 36 shows a pattern as in FIG. 32 having three visual markers of different colors except that the marker widths are not equal and the window widths are not equal;

FIG. 39 is a cross-sectional view of the angular width of a radially asymmetric pattern having a marker;

FIG. 40 is a ray-trace diagram of the model of FIG. 39;

FIGS. 43 and 44 are ray-trace diagrams for tubing of the present disclosure having patterns wherein the markers ($N_m=5$ as in FIG. 43 and $N_m=3$ as in FIG. 44), wherein the markers and windows are of unequal widths;

FIG. 65 is a perspective, isometric view of a portion of tubing of the present disclosure having a slot-shaped lumen geometry;

FIG. 66 is a cross-sectional view of the tubing of FIG. 65;

FIG. 67 is a perspective, isometric view of a portion of tubing of the present disclosure having a slot-shaped lumen geometry; and FIG. 68 is a cross-sectional view of the tubing of FIG. 67.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

1. IIS Device

Figure 1:
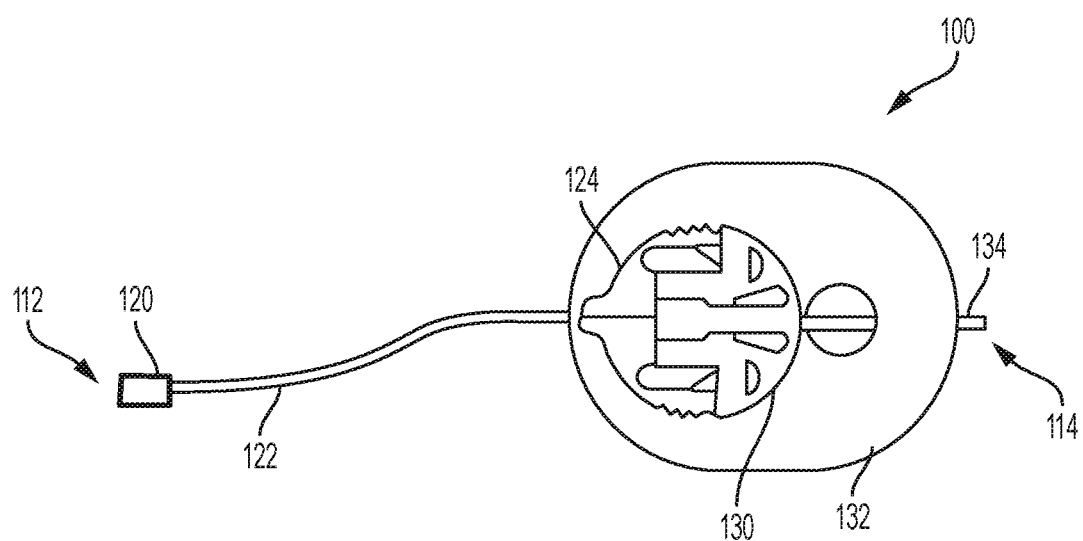
FIG. 1 is a top plan view of an exemplary insulin infusion set (IIS) device of the present disclosure.

An exemplary IIS device 100 of the present disclosure is shown in FIG. 1. The illustrative device 100 includes a first, proximal end 112 that communicates with an insulin reservoir of a pump (not shown) to receive an insulin formulation and a second, distal end 114 that communicates with a patient (not shown) to deliver the insulin formulation (i.e., the infusate). At the first end 112, the illustrative device 100 includes a reservoir connector 120 configured to couple with the insulin reservoir, a flexible line set tubing 122, and a base connector 124 in the shape of a male buckle portion. At the second end 114, the illustrative device 100 includes an infusion base 130 in the shape of a female buckle portion configured to receive the base connector 124, an adhesive pad 132 configured to adhere the infusion base 130 to the patient's skin, and an infusion catheter 134 configured for insertion into the patient's skin. In use, the insulin formulation is directed from the pump, through the line set tubing 122, through the infusion catheter 134, and into the patient's subcutaneous (SC) tissue.

Device 100 may include a viewing area with one or more visual effects to promote visibility of any air bubbles traveling through the viewing area. These effects, including optical features such as magnification, may help distinguish undesired air bubbles from the desired liquid drug product based on the different indices of refraction between air (about 1.0) and most liquid drug products or other aqueous solutions (about 1.33). Thus, the optical properties of device 100 will change depending on whether device 100 contains undesired air bubbles and/or the desired liquid drug product. Device 100 may be described as being "filled" when tubing 122 is filled with the desired liquid product and free of air bubbles. On the other hand, device 100 may be described as being "unfilled" or "empty" when tubing 122 is filled with air. Between these two conditions, device 100 may be described as being "partially filled" when tubing 122 contains air bubbles dispersed in the desired liquid product. Device 100 may enable the user to distinguish the desired "filled" condition from the other conditions. Exemplary features are described further below.

While the present disclosure focuses on an IIS platform, the principles described herein have broad applicability in the field of fluid delivery, specifically drug delivery, and more specifically parenteral drug delivery. For example, the principles described herein may be used to distinguish any media having different indices of refraction, such as two immiscible liquids.

2. IIS Device Index-Matched to Drug Product

Figure 2:
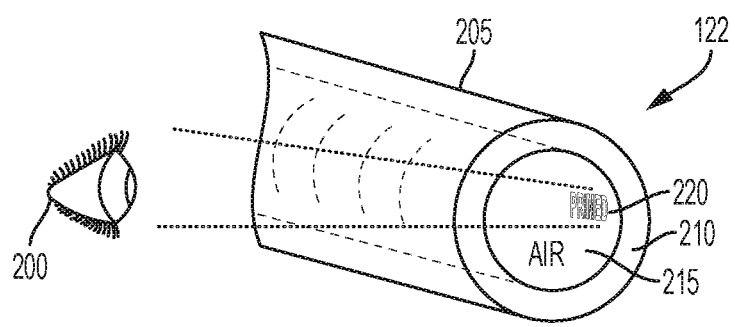
FIG. 2 is a perspective view of a transparent tubing having a viewing location on a roughened interior surface according to some embodiments of the present disclosure.

According to an exemplary embodiment of the present disclosure, as shown in FIG. 2 device 100 includes a viewing area 220 that has an index of refraction that is closer to that of the liquid drug product than to that of air. The viewing area 220 may be located in tubing 122 of device 100 (FIG. 1) or another suitable area of device 100. The viewing area 220 may be located in the fluid pathway within tubing 122. The viewing area 220 may include a visual marker 225 such as a word (e.g., "PRIMED"), symbol, and/or pattern. The viewing area 220 may be localized or extended along any length of the device.

Figure 3:
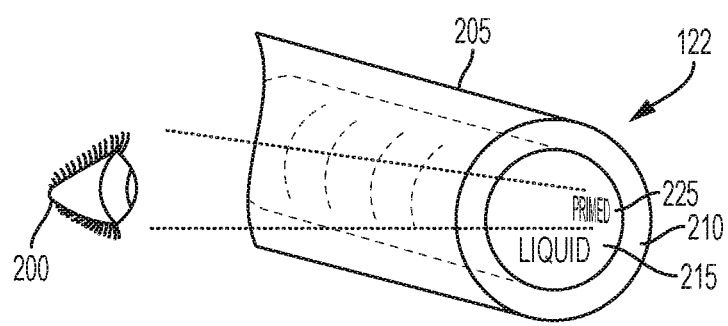
FIG. 3 is a perspective view of the transparent tubing of FIG. 2 including a liquid drug product therethrough.

In one embodiment of this invention, the transparent infusion set tubing 122 has an index of refraction close to that of the drug product delivered therethrough. In an example aspect, the drug product is an aqueous solution having an index of refraction of about 1.33. By comparison, the index of refraction of air, for example a bubble within the tubing 122, is about 1.0. As shown in FIGS. 2 and 3, tubing 122 has an outer surface 205, with a smooth finish that is free of defects, irregularities, or micro-scratches. Inner surface 215 of tubing 122 defines a fluid pathway and may be deliberately made rough, preferably by introducing surface roughness in the form of micro-scratches during the extruding process. The rough inner surface 215 of tubing 122 makes it opaque or semi-opaque when the lumen is filled with air. FIG. 2 shows tubing 122 wherein no fluid drug product is flowing through and air is contained with the tubing. Therefore the location 220 is difficult to read, for the example as shown in FIG. 2 the word "PRIMED" at viewing location 220 is blurry. When the drug product flows into tubing 122, as shown in FIG. 3, and displaces the air or air bubbles, the liquid drug product fills the micro-scratches on inner surface 215 of tubing 122. Because the drug product—compared to air—has an index of refraction that is closer to that of the tubing material, the tubing appears visually to be more transparent. Tubing 122 is typically plastic; suitable materials for tubing 122 include polypropylene, polyvinyl chloride, polyethylene, polyurethane, and silicone. However, any fully transparent or partially transparent (i.e., translucent) tubing made of any plastic or glass may be employed. The index of refraction (n) for the plastic tubing ranges from about 1.40 to 1.53, and the non-limiting example of fused silica glass has an index of refraction of 1.458, and these n values are more closely matched with the aqueous drug product having an index of refraction of about 1.33 (as compared with air at 1.0). The change in transparency allows a user 200 (e.g., a caregiver or a patient utilizing insulin pump therapy) to see a word or pattern that is engraved or drawn on the inner surface 215 of the far wall 210, or on the outer surface 205 of the far wall 210. This embodiment is shown in FIG. 3 wherein the word "PRIMED" 225 at viewing location 220 is visible indicating to the user 200 that the tubing is free of air bubbles. In embodiments in which the device has an extended viewing area 220, the word "PRIMED" 225 or any other appropriate pattern, may be repeated along the full length of the viewing area 220.

3. IIS Device with Integrated Lens

Figure 4:
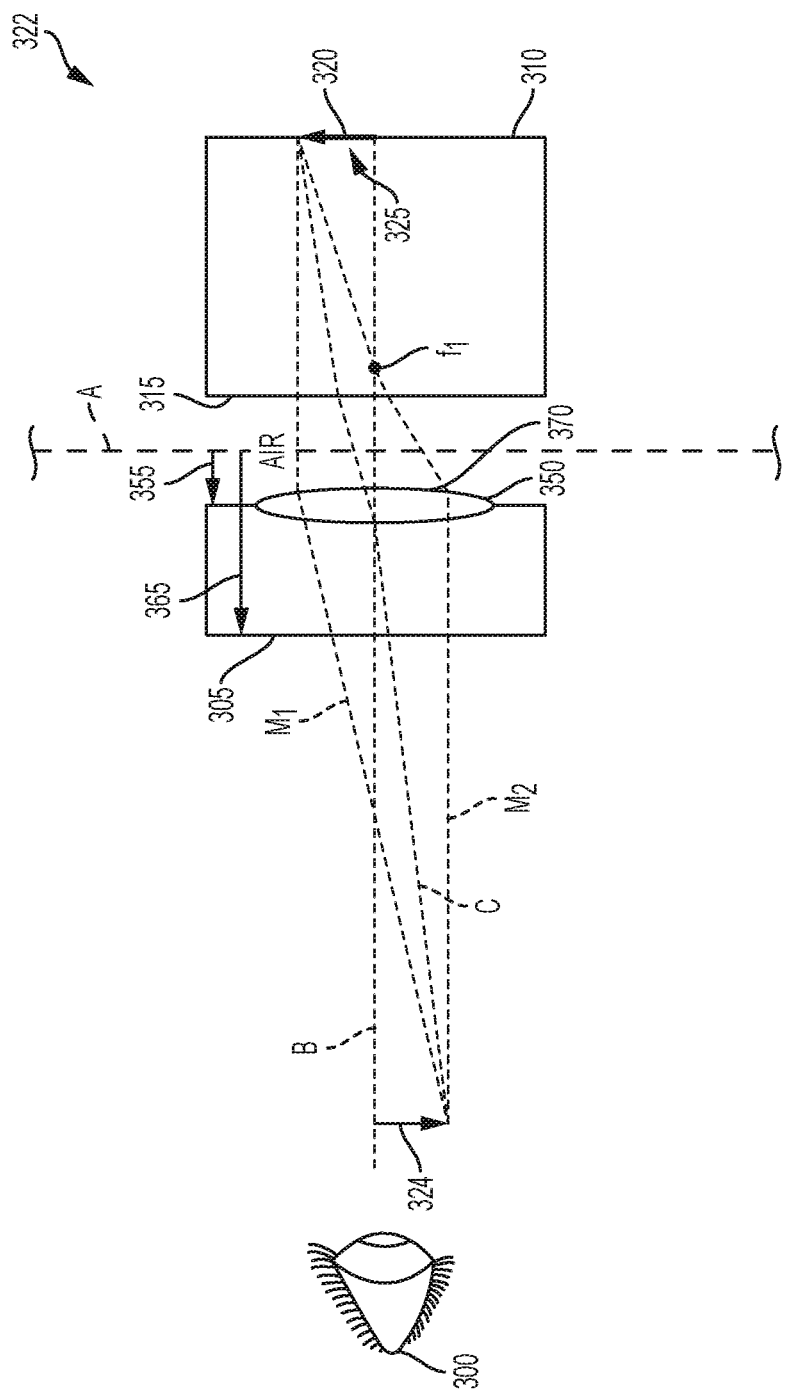
FIG. 4 is a longitudinal partial cross-sectional view of a transparent tubing having a viewing location, the transparent tubing having an integrated lens protruding from the interior of the tubing, according to some embodiments of the present disclosure.
Figure 5:
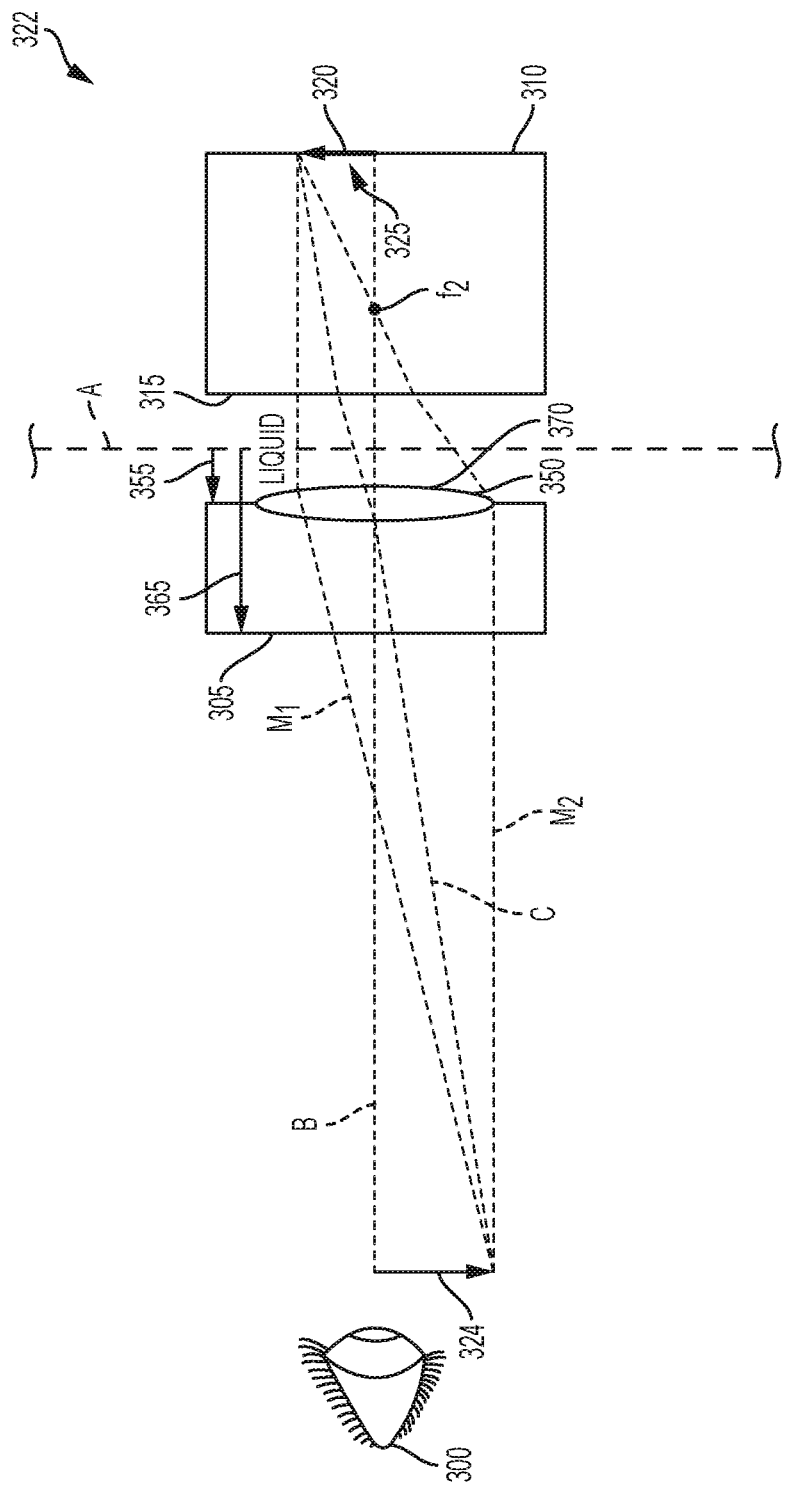
FIG. 5 is a longitudinal partial cross-sectional view of the transparent tubing of FIG. 4 including a liquid drug product therethrough.

An exemplary embodiment of the present disclosure, utilizing at least the index of refraction of the drug product flowing within the tubing 322 to cause a change in appearance that is visible to the user's eye 300, is illustrated in FIGS. 4 and 5. FIGS. 4 and 5 represent a cross-sectional view of the tubing 322, with the section cut aligned with the longitudinal axis A of the tubing 322. User's eye 300 is looking down optical axis B, which is perpendicular to longitudinal axis A. Tubing 322 (which may be similar to the above-described tubing 122) includes at least one viewing area 325 with a visual marker 320 such as an arrow (e.g., "↑") or another symbol, word or phrase, and/or pattern printed onto, embedded into, or otherwise incorporated into far wall 310 of tubing 322. As in FIGS. 4 and 5, visual marker 320 is represented by an arrow ↑. Tubing 322 also includes an integrated lens 350 incorporated into the transparent tubing 322 and located opposite from (e.g., about 180 degrees from) the viewing area 325, such that viewing area 325 is visible through lens 350 and along optical axis B. Tubing 322 further includes longitudinal axis A, inner circumferential surface 315 at a radial distance 355 from center, and an outer circumferential surface 305 at a radial distance 365 from center. The inner circumferential surface 315 defines a fluid pathway for delivering a first medium therethrough. In some embodiments, the first medium is a liquid drug product. The integrated lens 350 is disposed at the inner circumferential surface 315 of the tubing 322 and includes an interior surface 370 protruding from the inner circumferential surface 315. The viewing area 325 may be coaxial with the longitudinal axis A of the tubing 322. When viewing area 325 is viewed through lens 350, an image 324 of the marker 320 is formed in the user's eye 300. As in FIGS. 4 and 5, image 324 is represented by an inverted arrow ↓. The magnification effect, as detailed in the embodiments of FIGS. 4 and 5, and other optical qualities of the image 324 formed depend on the shape and dimensions of the tubing 322 and lens 350, as well as the index of refraction of the medium within the tubing 322. Other optical qualities and/or effects are discussed and detailed in embodiments disclosed further in the disclosure below.

In the exemplary embodiment of FIGS. 4 and 5, the effective back focal length (i.e. $f_1$, $f_2$, etc.) of the lens 350 is shifted depending on the presence or absence of a first medium, a second medium, or a combination of first and second media within the tubing 322. This shift in focal distance results in a corresponding change in the path of the chief C and meridional rays $M_1$ and $M_2$, and thus also a corresponding change of the location and size of the image 324 formed by the lens 350 as seen by the observer's eye 300. That is, in this exemplary embodiment, the magnification of the marker 320 depends on the index of refraction of the medium or media in the tubing 322. The use of lens 350 further amplifies the difference in magnification of the marker 320, as compared to a configuration with no lens 350 present. In FIG. 4, for example, the observer's eye 300 sees a relatively small image 324, which indicates the presence of the second medium (e.g., air). In FIG. 5, for example, the observer's eye 300 sees a relatively large image 324, which indicates the presence of the first medium (e.g., liquid drug product) and the absence of the second medium (e.g., air). While in the cross-sectional views of FIGS. 4 and 5 a single lens 350 in the tubing 322 is shown, multiple lenses in series may be utilized or, alternatively a long extended lens could be extruded as part of the tubing 322, and therefore run the full length of the tubing 322. In some embodiments, a plurality of viewing areas 325 are disposed continuously or intermittently along the length of the tubing 322, i.e. parallel to a longitudinal axis A.

While the embodiments depicted in FIGS. 4 and 5 illustrate a transparent tubing 322 system utilizing visual effects caused at least by differences in media indices of refraction in conjunction with lensing magnification to amplify those differences in order to promote ease of detection, it will be evident to those of skill of the art that a variety of differential visual effects may be produced depending on the specific design of optical elements useful in the tubing, the tubing structure 322 and materials, and the indices of refraction of the at least first and second media. Optical qualities that may be modified singularly or in combination include non-limiting examples such as magnification, displacement, distortion, brightness and color.

Figure 6:
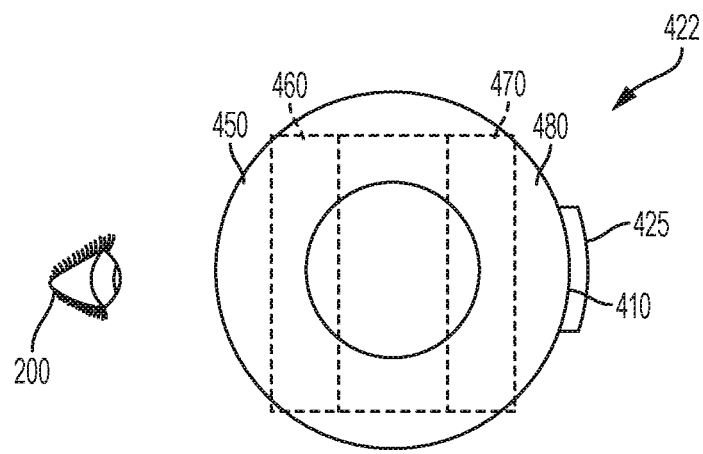
FIG. 6 is a cross-sectional view of a transparent tubing having an integrated lens within the tubing according to some embodiments of the present disclosure.

In another exemplary embodiment of the present disclosure, the tubing 422 itself serves as the lensing elements that enable detection of air bubbles in the tubing. FIG. 6 schematically illustrates tubing 422 in cross-section including multiple lenses in series across tubing 422 (which may be similar to the above-described tubing 122). Tubing 422 includes four lenses: plano-convex lens 450, plano-concave lens 460, plano-concave lens 470, and plano-convex lens 480. The series of lenses 450-480 bends light rays 490 depending upon at least (i) the material from which the tubing lenses 450-480 are made; and, (ii) the media in which the tubing lenses 450-480 are filled. With respect to characteristic (i), each lens 450-480 may be constructed of a desired material having a desired index of refraction to direct light in tubing 422 and optimize the detection of air bubbles in tubing 422. With respect to characteristic (ii), the media (i.e. tubing 422 filled with air or a liquid, for example a liquid drug product) have different indices of refraction. Tubing 422 also includes at least one viewing area 425 (which may be similar to the above-described viewing area 325) with a visual marker such as a word, symbol, and/or pattern printed onto, embedded into, or otherwise incorporated into far wall 410 of tubing 422. When viewing area 425 is viewed through lenses 450-480, the visual appearance of the visual marker is dependent upon whether the fluid pathway or lumen of the tube 422 is filled with a first medium, such as a drug product, having a first index of refraction $n_1$, or a second medium, such as air bubbles, having a second index of refraction, $n_2$, which enables a user to distinguish the drug product from the air bubbles in a non-limiting example. Further modification to the tubing 422 as detailed below may enable a user to more easily distinguish air bubbles from the liquid drug product. In some embodiments, a first medium as referred to herein is a liquid drug product and a second medium as referred to herein is air or air bubbles.

As shown in FIGS. 7-10, tubing 522A-522D each includes longitudinal axis (not shown) extending through a center 50. Tubing 522A-522D each has an inner circumferential surface 515 at a first radial distance ($r_1$) from center 50, wherein the inner circumferential surface 515 defines a fluid pathway therethrough for delivering a first medium, for example a liquid drug product, having a first index of refraction $n_1$. Tubing 522A-522D each has an outer circumferential surface 505 at a second radial distance ($r_2$) from center 50. Tubing 522A-522D each has at least one integrated lens 550A-550D. FIGS. 7-10 are cross-sectional views of exemplary tubing 522A-522D (which may be similar to the above-described tubing 122) having integrated lenses 550A-550D, each lens 550A-550D disposed at the outer circumferential surface 505 of the tubing 522A-522D according to alternative embodiments of the present disclosure. Tubing 522A-522D each has at least one viewing area, 525 (which may be similar to the above-described viewing areas 325 and 425) with a visual marker such as a word, symbol, and/or pattern printed onto, embedded into, or otherwise incorporated into far wall 510 of tubing 522. When viewing area 525 is viewed through the corresponding lens 550A-550D, the visual appearance of the visual marker is dependent upon whether the fluid pathway of the tube is filled with a first medium, such as a drug product, having a first index of refraction $n_1$, or a second medium, such as air bubbles, having a second index of refraction, $n_2$. By modifying the tubing 522A-522D radii of curvature of the outer diameters of the tubing, optical differences may be enhanced thus making detection of the second medium, for example any air bubbles present, much easier.

Figure 7:
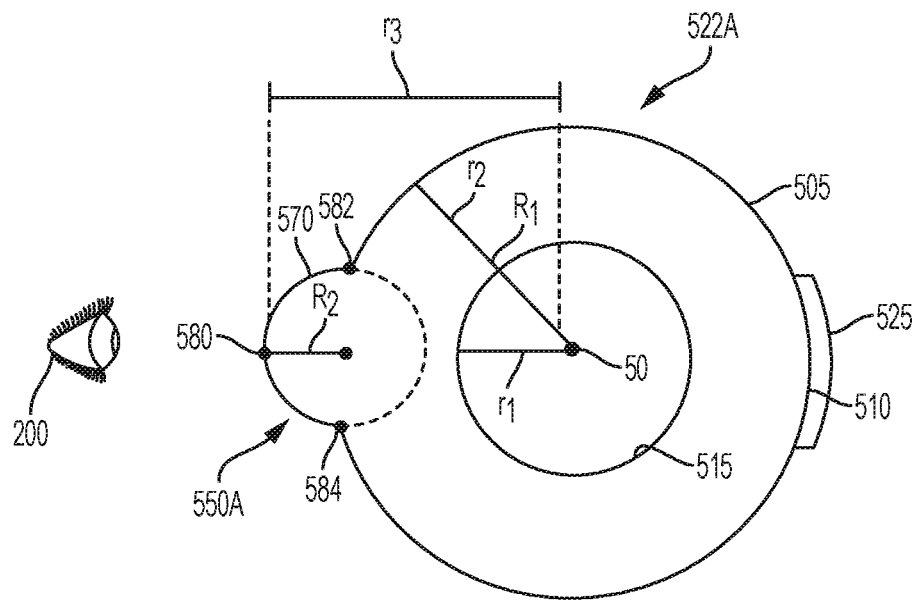
FIGS. 7-10 are cross-sectional views of a transparent tubing having an integrated lens disposed at the exterior of the transparent tubing according to alternative embodiments of the present disclosure.
Figure 8:
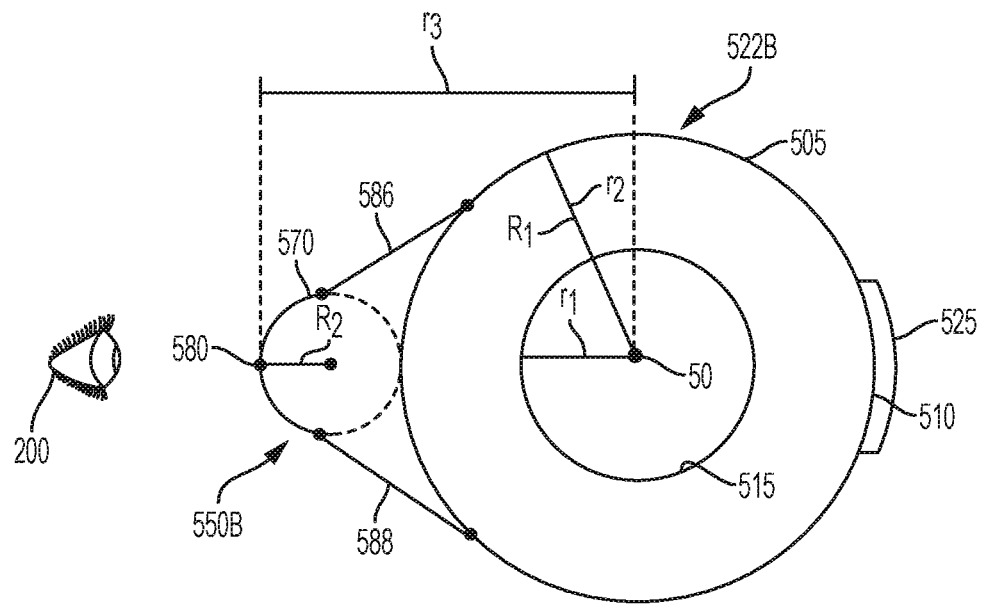
Figure 9:
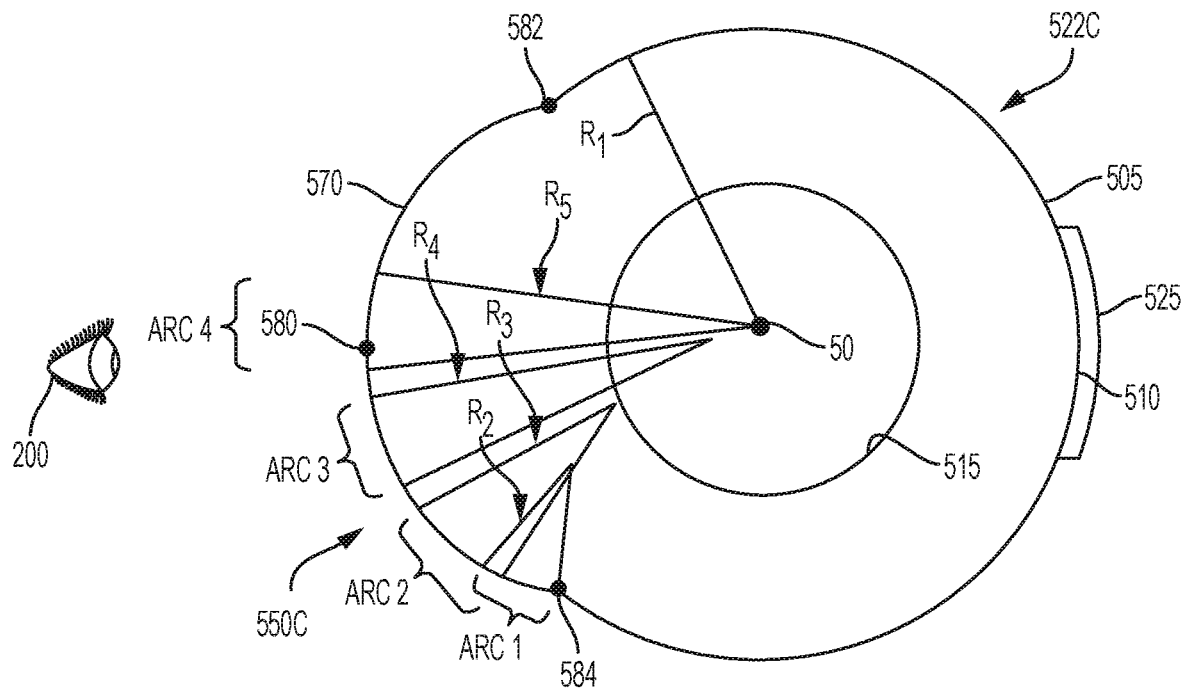

FIGS. 7-9 show tubing 522A-522C, wherein each integrated lens 550A, 550B, and 550C includes exterior surface 570 protruding from outer circumferential surface 505. Exterior surface 570 of each lens 550A, 550B, 550C includes at least one point 580 at a third radial distance ($r_3$) from the center 50. The third radial distance ($r_3$) is greater than the second radial distance ($r_2$). In these and other embodiments, exterior surface 570 of each lens 550A, 550B, 550C is convex. Outer circumferential surface 505 has a first radius of curvature ($R_1$) and exterior surface 570 of the lens 550A, 550B, 550C has a second radius of curvature ($R_2$). First radius of curvature ($R_1$) and the second radius of curvature ($R_2$) are different as shown in FIGS. 7-9. In the illustrated embodiment of FIGS. 7 and 8, outer circumferential surface 505 has a first radius curvature ($R_1$) and exterior surface 570 of the lens 550A, 550B has a second radius of curvature ($R_2$), wherein the first radius of curvature ($R_1$) is greater than the second radius of curvature ($R_2$). In the illustrated embodiment of FIG. 9, outer circumferential surface 505 has a first radius curvature ($R_1$) and the exterior surface 570 of the lens 550C has a plurality of radii of curvature ($R_{2\text{-}5}$). While $R_{2\text{-}5}$ are shown in FIG. 9, the number of radii of curvature for the exterior surface 570 of lens 550C are not limited to $R_2$, $R_3$, $R_4$, and $R_5$. As one of skill in the art would recognize, changing the radius of curvature for the exterior surface 570 of lens 550C may include any number of radii of curvature. Outer circumferential surface 505 and exterior surface 570 of the lens 550 meet at edges 582 and 584 as shown in FIGS. 7 and 9. Outer circumferential surface 505 is connected to exterior surface 570 of the lens 550 at planar faces 586 and 588 as shown in FIG. 8. Planar face 586 is inclined at a first slope and planar face 588 is inclined at a second slope, wherein the first slope is opposite the second slope.

Alternatively, the lens is an aspheric surface, wherein the aspheric surface defined as a conic section or traditional asphere. In some embodiments of the present disclosure, the integrated lens 350, 450-480, 550A-D is aspheric, in other words, optical surfaces with non-spherical profiles. In other embodiments, the lens is a freeform surface, wherein the curvature is arbitrary. In some embodiments of the present disclosure, the tubing 122, 322, 422, 522A-D including the integrated lens 350, 450-480, 550A-D is formed as a single-piece construction. In other embodiments the tubing 122, 322, 422, 522A-D having the at least one integrated lens 350, 450-480, and 550A-D is of multi-layer or compound construction.

Figure 10:
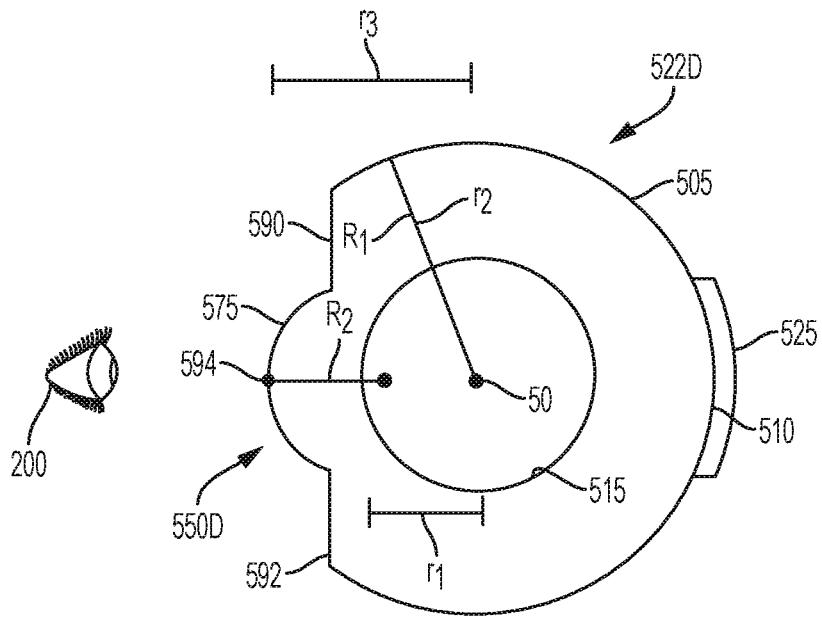

As shown in FIG. 10, integrated lens 550D includes exterior surface 575 connected to outer circumferential surface 505 by coplanar faces 590 and 592, wherein exterior surface 575 of the lens 550D includes at least one point 594 at a third radial distance ($r_3$) from the center 50, wherein the third radial distance ($r_3$) is greater than the first radial distance ($r_1$). Wherein planar faces are shown as in FIG. 10, the functional surfaces and their relative orientation are variable and the shape of the tubing can take many forms.

Figure 11:
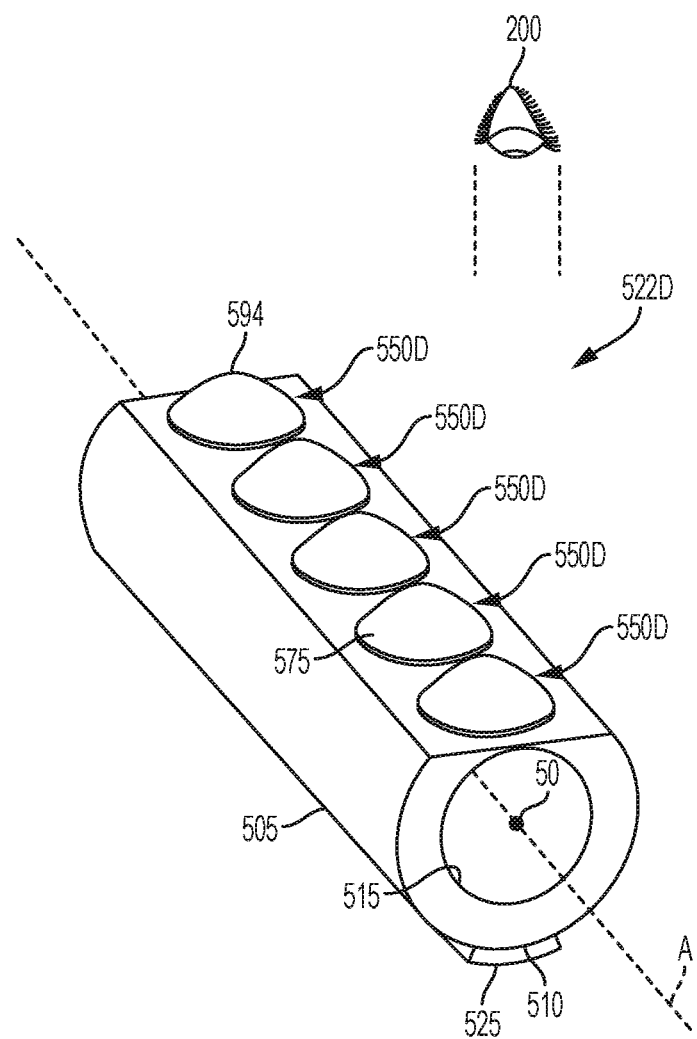
FIG. 11 is a perspective view of a transparent tubing having a series of plano-convex lenses, as shown in FIG. 10, integrated into the exterior surface of the tubing.

FIG. 11 is a perspective view of tubing 522D of FIG. 10 having a series of plano-convex lenses 550D integrated into the exterior surface 505 of the tubing 522D according to some embodiments of the present disclosure. As shown in FIG. 11, the plurality of plano-convex lenses 550D are disposed linearly and parallel to the longitudinal axis A. That is, the lenses are in a row, the row being disposed in parallel to the longitudinal axis of the tubing, with the optical axis of each individual lens being perpendicular to the longitudinal axis of the tubing. Lenses 550D are disposed opposite from (e.g., about 180 degrees from) the viewing area 525. Alternatively, as is envisioned but not shown in the perspective view of FIG. 11, the tubing 522D of FIG. 10 may include one continuous integrated lens disposed parallel to longitudinal axis A.

Figure 12:
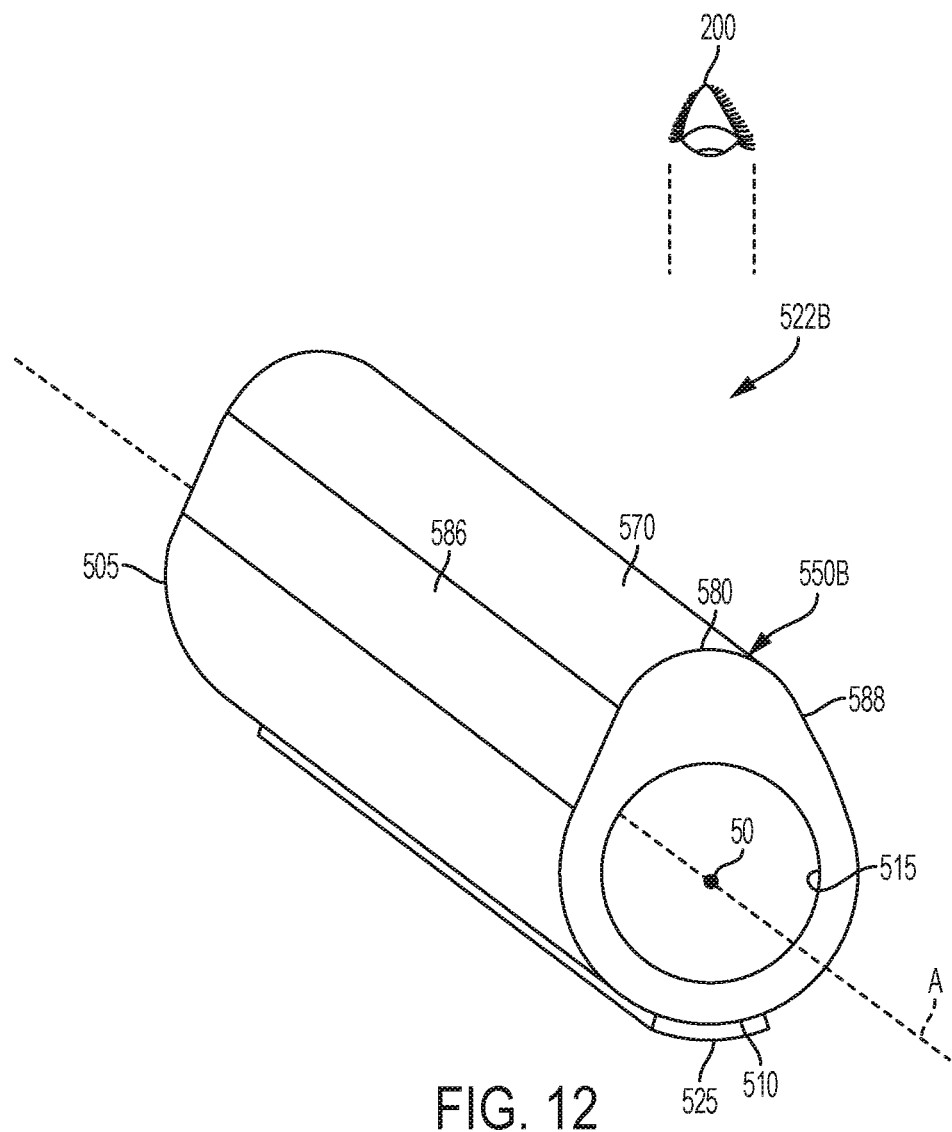
FIG. 12 is a perspective view of a transparent tubing having an elongated quasi-cylindrical lens, as shown in FIG. 8, integrated into the exterior surface of the tubing.

FIG. 12 is a perspective view of tubing 522B of FIG. 8 having an elongated quasi-cylindrical lens 550B integrated into the exterior surface 505 of the tubing 522B according to some embodiments of the present disclosure. Tubing 522B includes integrated lens 550B having an optical axis (or axes) that is perpendicular to the longitudinal axis of the tubing. As shown in FIG. 12, tubing 522B comprises an elongated cylindrical lens 550B disposed parallel to the longitudinal axis A. Lens 550B is disposed opposite from (e.g., about 180 degrees opposite from) the viewing area 525. While lens 550B is shown as one continuous lens, alternatively lens 550B is a plurality of lenses distributed longitudinally.

The embodiments of FIGS. 11 and 12 are two non-limiting examples of the present disclosure. As one of skill in the art would recognize, changing the radius of curvature of the outside of the tube 522B, 522D can be accomplished in one or two dimensions. By altering the external shape of the tubing 522B, 522D, optical paths are created that change and enhance detection of air within the otherwise liquid drug product filled fluid pathway as defined by the inner circumferential surface 515. Additionally, although the illustrative inner surface 515 is a conic section, appearing circular in shape, the inner surface 515 may also be polygonal-shaped, square-shaped, or another suitable shape.

While any suitable material compatible for medical device tubing 122, 322, 422, 522A-D may be used, infusion set tubing is typically made from one or more of the following materials:

TABLE 1

Tubing Materials

| Material | Index of Refraction |
|---|---|
| polypropylene | 1.49 |
| polyvinyl chloride | 1.53 |
| polyethylene | 1.51 |
| polyurethane | 1.48 |
| silicone | 1.4-1.6 |
| fused silica glass | 1.46 |

The index of refraction does not vary significantly between the materials of Table 1. Moreover, these materials are inexpensive, lend themselves to extrusion forming methods, and are compatible with the liquid drug product. Materials may also be co-extruded. In other words, tubing may be formed with more than one material. Generally, co-extruded tubing is formed in layers or in a laminar arrangement. Referring back to the discussion above wherein light rays depend upon at least (i) the material from which the tubing lenses 350, 450-480, 550A-D are made; and, (ii) the media in which the tubing lenses 350, 450-480, 550A-D are filled, it has been shown that changes to the optics (i.e. by changing radii of curvature) are advantageously achieved in the present disclosure without having to alter the materials used in forming the tubing 122, 322, 422, 522A-D.

In some embodiments of the present disclosure, a transparent tubing is provided, wherein the transparent tubing comprises: a longitudinal axis having a center; an inner circumferential surface at a first radial distance ($r_1$) from the center, the inner circumferential surface defining a fluid pathway therethrough for delivering a first medium; an outer circumferential surface at a second radial distance ($r_2$) from the center; and, at least one integrated lens configured to direct light from the fluid pathway to detect a presence or an absence of a second medium, the second medium having a second index of refraction $n_2$, where $n_2$ is different from $n_1$.

In some embodiments of the present disclosure, a method 101 of making a transparent tube, having at least one viewing area with a visual marker that may be imaged by lenses integrated into the tubing, and as may be used for infusion-set tubing for an insulin pump, is provided. As illustrated in the flow chart of FIG. 13, the method 101 comprises selecting a material as in step 1000. The material is, for example, at least one material chosen from polypropylene, polyvinyl chloride, polyethylene, polyurethane, silicone, and glass. Next the method includes forming the material into an elongated tubing having a fluid pathway therethrough for delivering a liquid drug product as in step 1010. Exemplary tubings 122, 322, 422, 522A-D are described above. Step 1020 includes integrating a lens in the elongated tubing, the lens configured to direct light from a pattern or other visual marker of the viewing area, which may be printed-on or embedded in a far wall, the visual appearance of the visual marker being dependent upon the medium in the fluid pathway. Exemplary lenses 350, 450-480, 550A-D are described above. In some embodiments, integrating the lens includes constructing the lens of at least one material chosen from polypropylene, polyvinyl chloride, polyethylene, polyurethane, silicone, and glass. The material selected for the tubing in step 1000 may be the same or different than the material selected for integrating the lens in step 1020. Additionally, step 1020 may be performed after or concurrently with step 1010. Integrating the lens in the elongated tubing can mean along the entire length of the elongated tubing (as in a continuous lens), i.e. forming the material includes coextruding the elongated tubing and the lens. Alternatively, integrating the lens is performed discontinuously or intermittently with respect to the longitudinal axis (as in at least one lens or a series thereof integrated in the tubing). In some embodiments of the present disclosure, the lens is discontinuously disposed with respect to the elongated tubing longitudinally and/or circumferentially.

Figure 13:
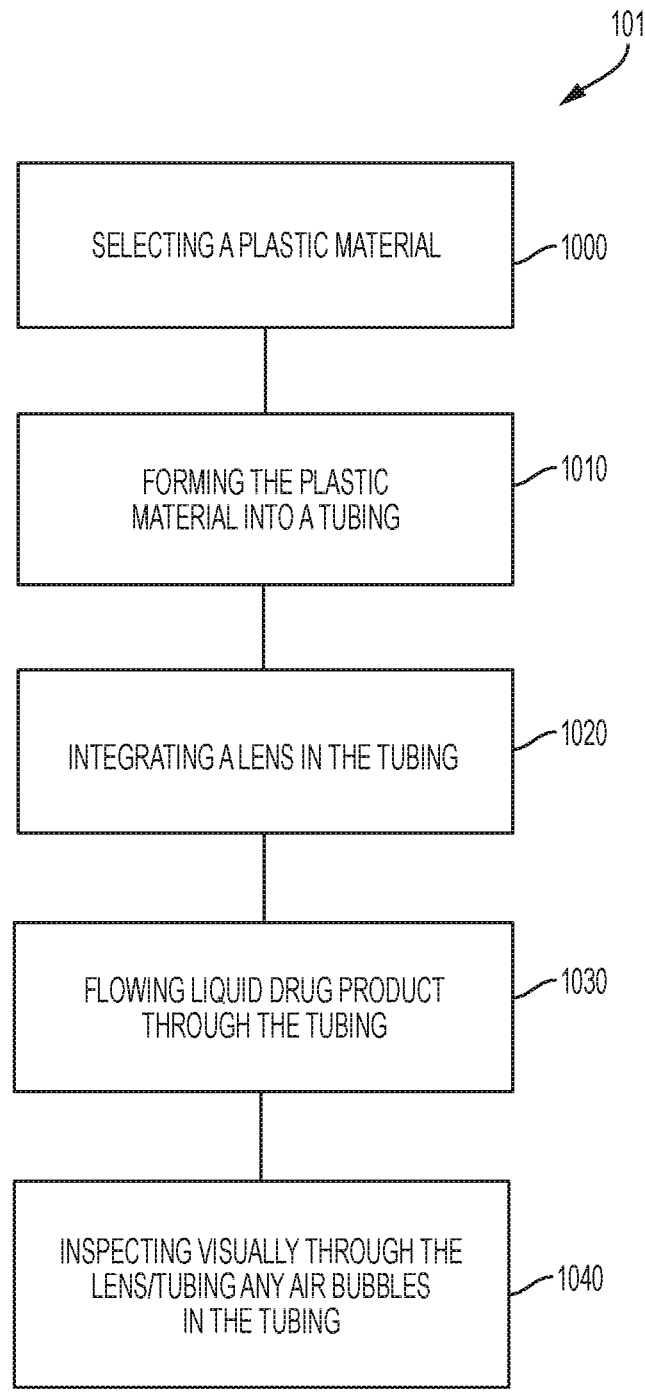
FIG. 13 is a flow chart illustrating a method of the present disclosure of making a transparent infusion-set tubing for an insulin pump.

FIG. 13 illustrates further optional steps after making the tubing for using the transparent infusion-set tubing for an insulin pump. Steps for using include flowing a liquid drug product through the tubing as in step 1030 and inspecting visually through the lens/tubing any air bubbles in the tubing as in step 1040.

Figure 14:
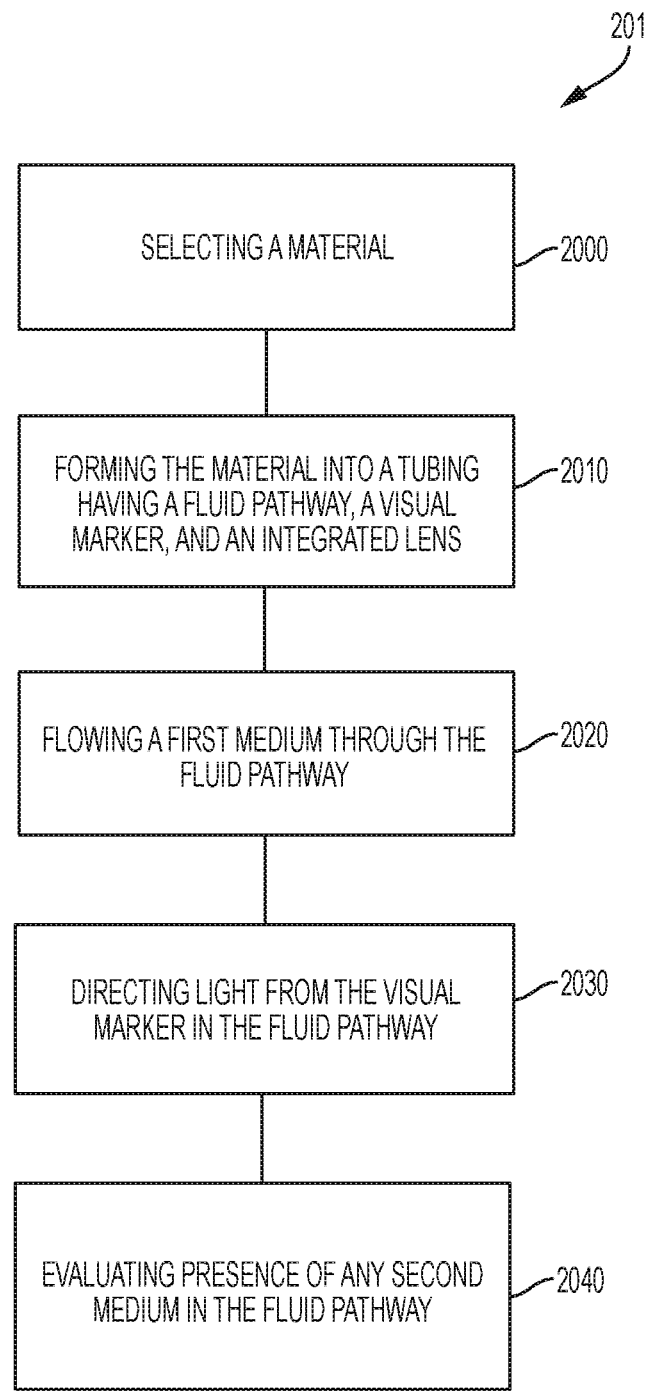
FIG. 14 is a flow chart illustrating another method of the present disclosure of making a transparent tubing.

FIG. 14 illustrates method 201 for making a transparent tube and detecting media therethrough. Step 2000 includes selecting a material chosen from at least one of polypropylene, polyvinyl chloride, polyethylene, polyurethane, silicone, and glass. Step 2010 includes forming the material into an elongated tubing. The elongated tubing includes a fluid pathway and a longitudinal axis therethrough for delivering a first medium having a first index of refraction $n_1$, the elongated tubing including at least one viewing area with a visual marker parallel to the longitudinal axis. Step 2010 further includes integrating at least one lens in the elongated tubing, the at least one lens disposed opposite from (e.g., about 180 degrees from) the at least one visual marker. The lens is configured to direct light from the at least one visual marker for detecting a presence or an absence of a second medium in the fluid pathway, the second medium having a second index of refraction $n_2$, where $n_2$ is different from the first index of refraction $n_1$. Alternatively, step 2010 may include multiple sub-steps wherein (i) the tubing is formed, (ii) the visual marker is applied to, etched onto, or otherwise embedded or integrating into the tubing, (iii) the integrated lens is formed onto and/or within the tubing, and (iv) combinations of steps thereof. Step 2020 includes flowing the first medium having $n_1$ through the fluid pathway. Step 2030 includes directing light to pass from the visual marker in the fluid pathway. Step 2040 includes detecting the second medium having $n_2$ if present in the fluid pathway as discerned by evaluating the visual marker.

4. Optical Effects

Figure 15:
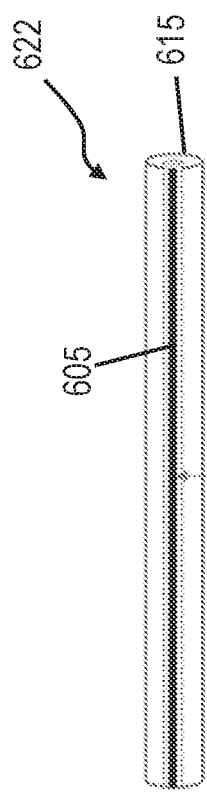
FIG. 15 is a perspective view of a tubing having a lumen and a visual marker of the present disclosure.
Figure 16:
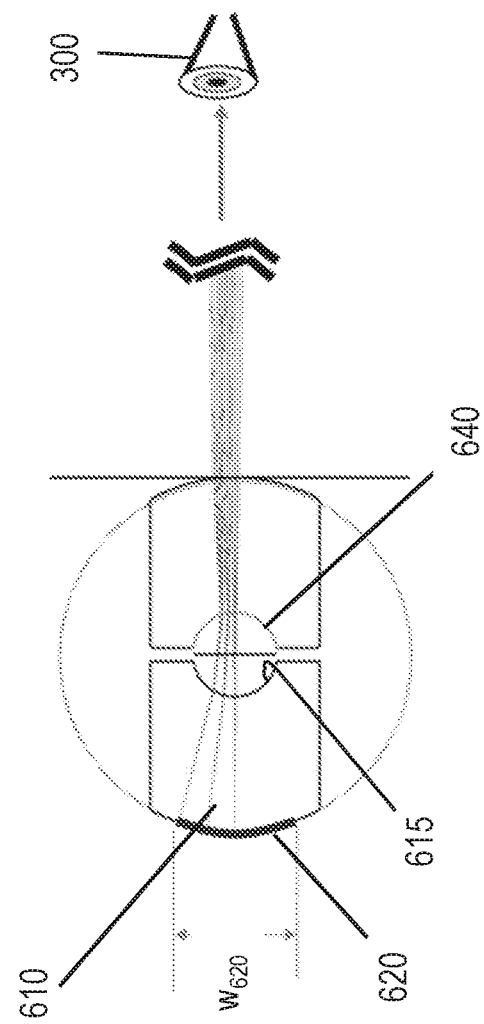
FIG. 16 is a cross-sectional view of the tubing of FIG. 15.

An exemplary embodiment of the present disclosure, utilizing at least one optical effect to cause a change in appearance that is visible to the user's eye 300 when the drug product is flowing within the tubing 622, is illustrated in FIGS. 15-16. Tubing 622, or a "simple tube," is defined here as a cylindrical tube with a concentric cylindrical lumen 640. Tubing 622 itself may act as a lens and include patterns or geometric features thereon or therein to provide optical effects to enhance visualization of media within the tubing 622. FIG. 15 illustrates a visual marker or stripe 620 along the outer circumferential surface 605 of tubing 622, while inner circumferential surface 615 defines the lumen 640, which serves as a fluid pathway. As is similar to the embodiment of FIGS. 4 and 5, a magnification optical effect is utilized. With user's eye 300 viewing a stripe 620 on the far wall 610 through tubing 622, the image of the stripe 620 is magnified by an amount that depends upon whether the lumen 640 of the tubing 622 is filled (e.g., contains liquid drug product) or unfilled (e.g., contains air). For tubing 622 having lumen 640 filled with air and no liquid drug product, the width of stripe 620 is magnified or demagnified by a first amount. For tubing 622 having lumen 640 filled with liquid drug product, the width of stripe 620 is magnified or demagnified by a second amount. As in the prior embodiments, tubing 622 of the present disclosure may be fully transparent or partially transparent (e.g., tinted); may be large or small; may be composed of a single material, or may be a multi-laminate construction. The tubing 622 may be made of glass or plastic or any other suitable material, and the material(s) from which it is composed may have any suitable index of refraction. The liquid flowing within the lumen may be of any type, provided that its index of refraction differs from that of the other medium (e.g. air) that it is displacing or from which it is being distinguished. The stripe 620 on tubing 622 may be modified with patterns and/or geometric features to enable easy visualization of air bubbles contained therein.

An exemplary pattern according to the present disclosure is a single opaque or translucent stripe 620 that runs longitudinally on the outer circumferential surface 605 of tubing 622, parallel to the lumen 640, as shown in FIGS. 15 and 16. At least one optical effect occurs when stripe 620 is viewed by the user's eye 300 through the tubing 622. These optical effects include (a) imaging with magnification through the lumen (as described above), (b) reflections at the lumen/cladding interface, and (c) secondary imaging bypassing the lumen. These optical effects and their impact on the visualization of media within tubing 622 of the present disclosure are detailed below.

Imaging with Magnification Through the Lumen.

Figure 18:
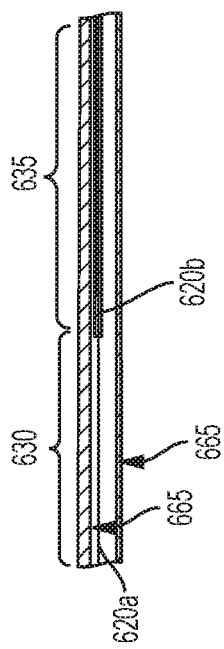
FIG. 18 is a top view of the tubing of FIG. 17.
Figure 17:
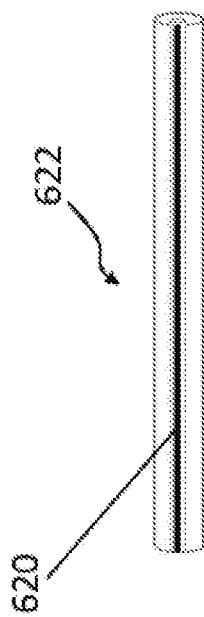
FIG. 17 is a perspective view of a tubing having a lumen and a visual marker of the present disclosure.
Figure 20:
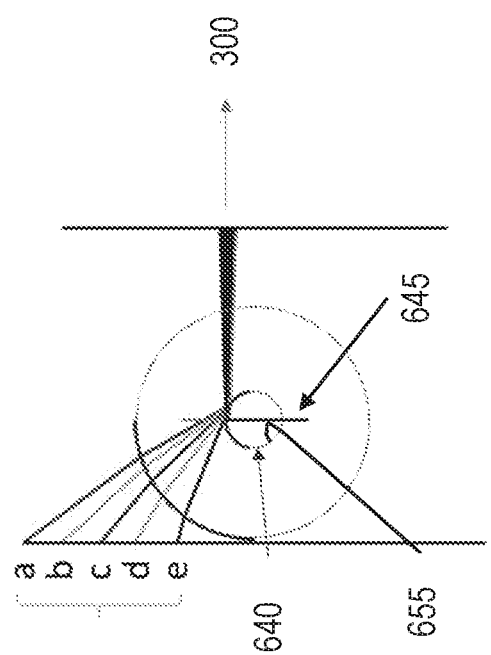
FIG. 20 is a schematic ray-trace diagram for the tubing of FIG. 19.
Figure 19:
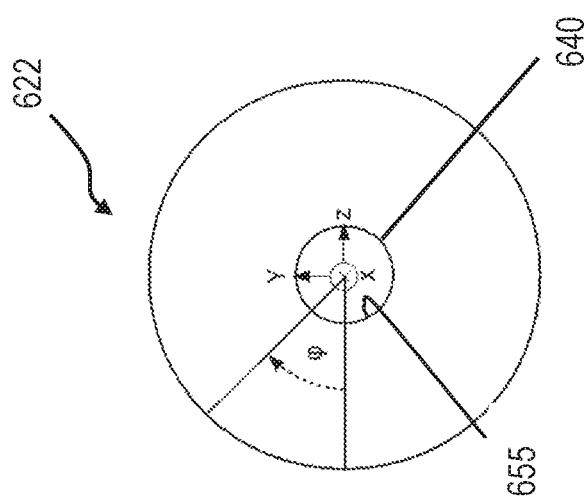
FIG. 19 is a cross-sectional view of the tubing of FIGS. 17-18.

A magnification optical effect occurs when a user 300 looks through tubing 622 at a visual marker, such as a stripe 620 on the far wall 610, the magnitude of the effect dependent upon whether the lumen 640 of the tubing 622 is filled (e.g., contains liquid drug product) or unfilled (e.g., contains air), as described above and as shown in FIGS. 15 and 16. Optical modeling of the cross-section of the tubing 622, as shown in FIG. 16, shows the width of the stripe 620 as imaged by the eye 300. In this example, the width of stripe 620 appears narrower when lumen 640 is unfilled and wider when lumen 640 is filled with a liquid drug product. In the following examples, tubing 622 has an outer diameter of 1.6 mm and an inner diameter of 0.38 mm; however, those of skill in the art appreciate that the inner and outer diameter of tubing 622 may vary. An exemplary tubing 622 was placed over a piece of paper having a printed black line 620 about 0.25 mm in width, as shown in FIG. 17, with the axis of the tubing 622 and the printed line 620 coincident. Tubing 622 was half-filled with water to achieve a filled portion 635 and an empty portion 630 (e.g., containing air). As shown in FIG. 18, the magnification of stripe 620 differs depending upon the contents of lumen 640. The empty portion 630 of the tubing 622 has a narrow visible stripe 620a, and the filled portion 635 of tubing 622 has a wide visible stripe 620b.
Reflections at the Lumen/Cladding Interface.

a reflective optical effect occurs at the interface 655 of the lumen 640 with its cladding. The cladding is a covering of the lumen 640 or, as in FIG. 19, the tubing 622 itself. At interface 655, reflections occur that are dependent upon whether lumen 640 is filled (e.g., contains liquid drug product) or unfilled (e.g., contains air). FIG. 19 illustrates the incoming light rays entering the tubing 622 at an angle φ. Optical modeling as in FIG. 20 shows which rays will be reflected along the nominal optical axis 645 for tubing 622 (as in FIG. 19) having an outer diameter (OD) of about 1.6 mm and an inner diameter (ID) of about 0.38 mm. The model shows only the top half of the cross-section shown, but it is understood by those of skill in the art that the mirror image of rays are present also for the bottom half of the cross section. The reflection coefficient at the interface 655 between two materials is a function of incident angle for incident rays a, b, c, d, and e of FIG. 20 reflected at interface 655 and the refractive indexes of the two materials, where the first material is that from which the tubing 622 or cladding is made (e.g., plastic) and the second material is that which is contained within the lumen 640 (e.g., air and/or liquid drug product).

Figure 21:
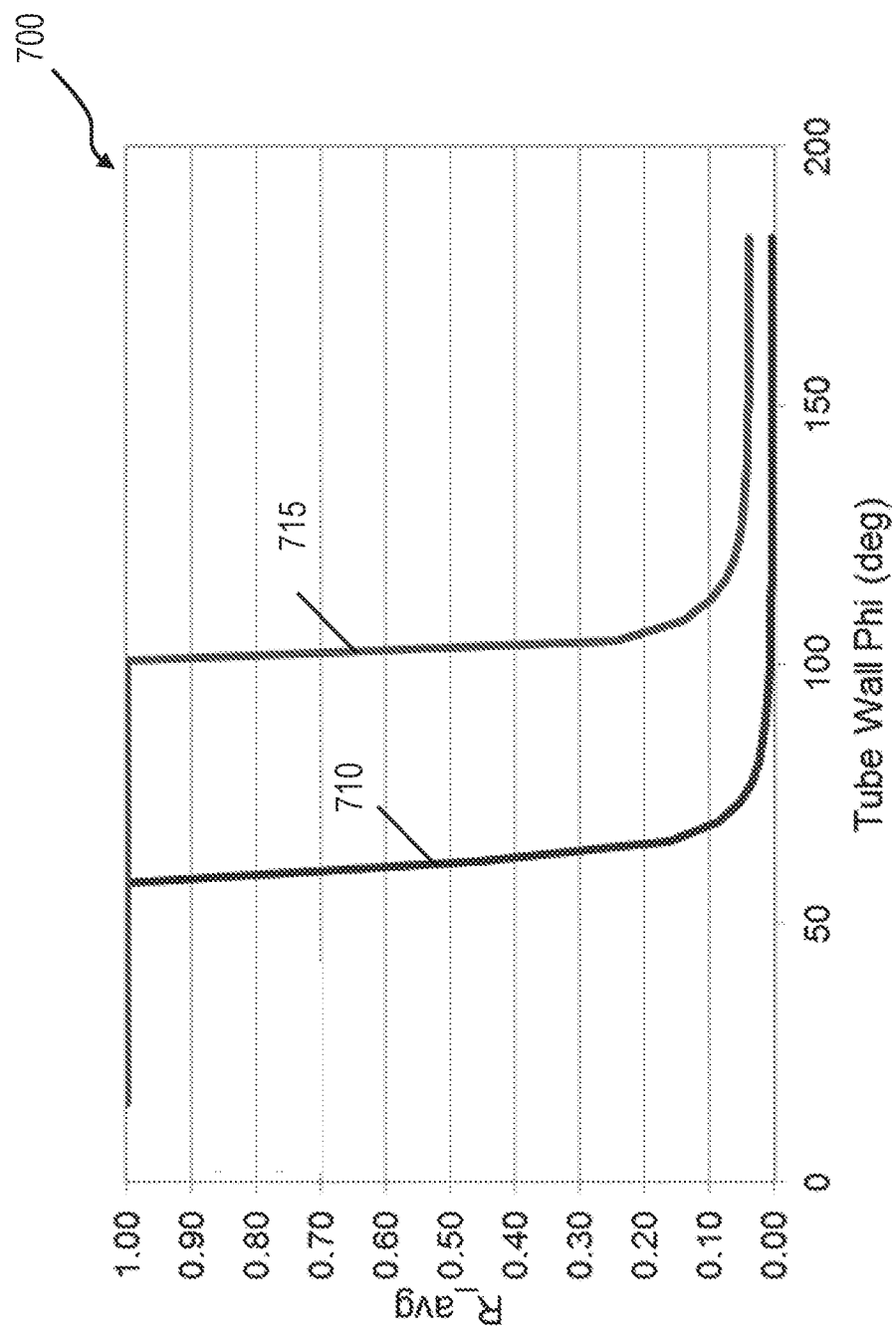
FIG. 21 is a plot of Fresnel reflection coefficients at the lumen/cladding interface for the tubing of FIG. 19.

As light moves from a first medium having a first refractive index, $n_1$, into a second medium having a second refractive index, $n_2$, both reflection and refraction of the light may occur. The Fresnel equations describe what fraction of the light is reflected and what fraction is refracted (i.e., transmitted). Fresnel reflection coefficients at the lumen/cladding boundary of a simple tubing 622, the reflection coefficients for light rays as a function of the positional angle phi, are plotted in graph 700 of FIG. 21. Plot 710 is shown for a lumen 640 filled with an aqueous solution where $n_1$ for plastic is about 1.46 and $n_2$ for water is equal to 1.33. Plot 715 is shown for an empty lumen 640 where $n_1$ for plastic is about 1.46 and $n_2$ for air is equal to 1. Reflection coefficients are plotted as a function of the angle phi (φ) that denotes the radial location, with respect to the Z-axis of FIG. 19 at which the impinging rays intersect the outer wall of the tubing 622. As shown in FIG. 21, all rays that hit the tubing at a radial location less than the angle described by curve 710 are transmitted to the eye of the observer, regardless of the state of the lumen (filled or unfilled). Similarly, all rays that hit the tubing at a radial location greater than the angle described by curve 715 will miss the eye of the observer, regardless of the state of the lumen. Only at radial locations described by the window between the curves 710 and 715, does the tube differentially reflect some rays to the eye, depending upon the state of the lumen.

Within this window of radial angles, the angular cone of light that is differentially reflected to the eye is also a function of the angle of incidence that the rays of light make with the tubing. Thus, rays "a"-"e" in FIG. 20 represent not only the extremes of the radial positions of rays of light that can be differentially reflected, but also the extremes of the angles of incidence at which differential reflection can occur. For instance, ray "a" is illustrated in the farthest radial location and at the most acute angle of incidence that can be differentially reflected to the eye 300. Similarly, ray "e" is illustrated in the closest radial location, and at the most oblique angle of incidence that can provide differential reflection off the lumen 640. Between these two extremes, rays "b"-"d" illustrate the nominal ray path through a given radial position that leads to differential reflection from the lumen 640 as seen by the observer's eye 300.

Figure 22:
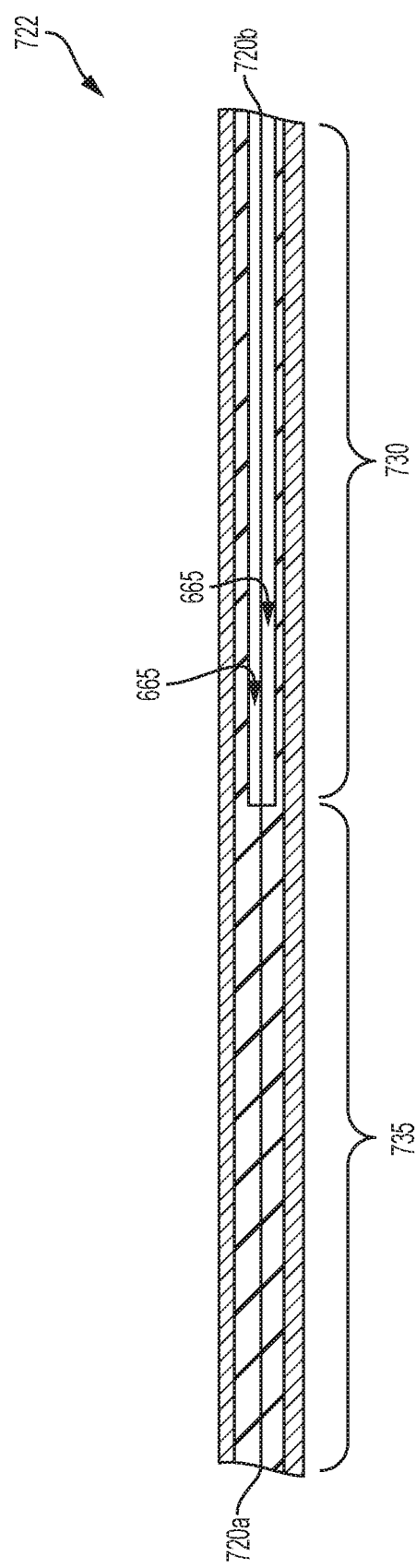
FIG. 22 is a top view of tubing of the present disclosure showing primary and secondary optical imaging effects.

The difference in the reflection coefficients, plots 710 and 715 as shown in FIG. 21, produces differences in reflected light that can also be useful as a visual marker to indicate the state of the lumen 640, in other words whether the lumen is filled or unfilled. In FIG. 22, an exemplary simple tubing 722 was placed over a piece of paper having a printed black line 720 of about 2.5 mm in width, with the axis of the tubing 722 coincident with the printed line 720. The tube 722 was half-filled with water to achieve a filled portion 735 and an unfilled portion 730. The reflections at the lumen/cladding interface are substantially more apparent in the unfilled portion 730 showing marker image 720b than in the filled portion 735 showing marker image 720a.
Secondary Images Through the Cladding.

Another optical effect, albeit potentially undesirable, occurs when a pattern or visual marker on the far wall of a tube is viewed through the tubing but does not pass through the lumen. Examples of secondary images 665 are shown in FIG. 18. Because the secondary imaging phenomenon bypasses the lumen, it is independent of the state of the lumen. The secondary images are unaltered by the presence or absence of liquid in the lumen. In other words, secondary images do not provide information as to whether the lumen is filled or unfilled. For example, these secondary images do not aid in visualizing air bubbles in a lumen carrying liquid drug product. In fact, these secondary images may distract and/or confuse the user, particularly because the secondary images can appear and disappear as the user rotates the tubing to slightly different observation angles as shown in FIGS. 23-25. As the tubing size (inner diameter and/or outer diameter) is reduced, the secondary images and primary magnification optical effect appear in very close proximity to each other, which is increasingly difficult for the user to discern.

Secondary effects are shown in FIGS. 23-25 for an exemplary simple tubing 822 having an outer diameter of 9.525 mm (⅜" O.D.), an inner diameter of 2.286 mm (0.090" I.D.), and a longitudinal visual marker or stripe 820 having a width of 3.175 mm (⅛") positioned on the far exterior wall of the tubing 822. As tubing 822 is rotated slightly about longitudinal axis A in a first direction, as in FIG. 23, with the stripe 820 appearing slightly more towards the top of the tubing 822, the secondary image(s) 865a of the stripe 820 appears only in the upper portion of the tubing 822. At the desired observation angle, as in FIG. 24, wherein the stripe 820 is positioned coincident with axis A so that the stripe 820 is viewed directly through the tubing 822, secondary images 865b of the stripe 820 appear both in the top and bottom portions of the tubing 822. As tubing 822 is rotated about longitudinal axis A in a second direction, opposite the first direction, as in FIG. 25, so that the stripe 820 is observed slightly more towards the bottom of the tubing 822, the secondary image(s) 865c of the stripe appear only in the bottom portion of the tubing 822. Secondary images 865a, 865b, 865c, as shown in FIGS. 23-25, may be a distraction and obscure information desired from the desired visual marker 820.

Figure 26:
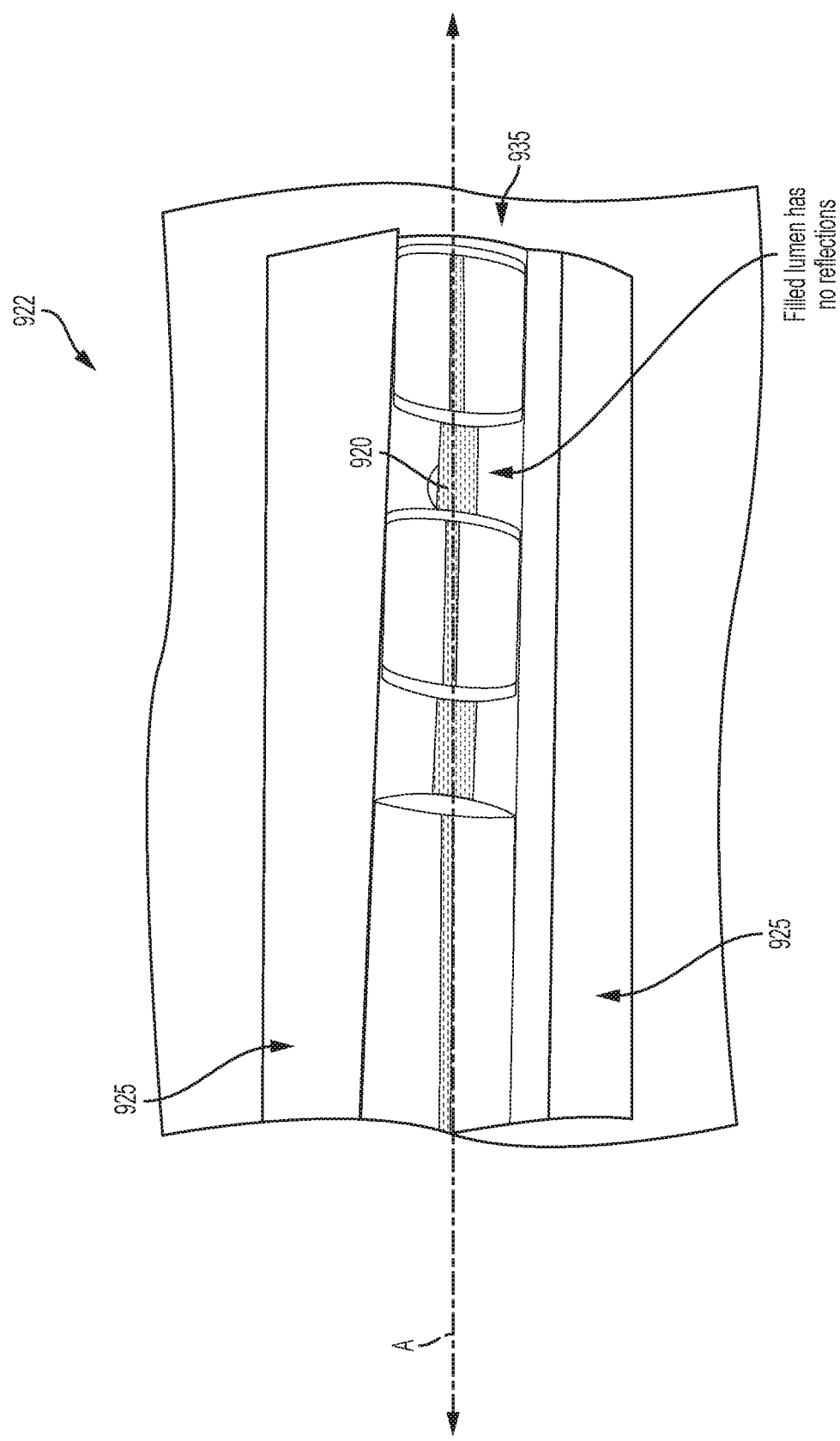
FIG. 26 is a top view of a tubing of the present disclosure having masking markers to prevent secondary optical imaging effects.

Because the secondary images 865a, 865b, 865c, obscure rather than contribute to the user's ability to distinguish between a filled and unfilled lumen, it may be desirable to mask these secondary images 865a, 865b, 865c. In an exemplary embodiment as shown in FIG. 26, secondary images (not shown) are successfully blocked or masked using a mask 925 (e.g., another marker, tape) positioned on the tubing 922 away from the stripe or visual marker 920 to be viewed through the tubing 922. The secondary images are blocked through masking while the reflections at the lumen/cladding interface are enhanced. As shown in FIG. 26, an exemplary simple tubing 922 having an outer diameter of 12.7 mm (0.5" O.D.) and an inner diameter of 3.048 mm (0.120" I.D.) includes a pattern of markers: (i) a single longitudinal marker or stripe 920 on the back wall, wherein stripe 920 may be of a first color or pattern, and (ii) two or more masks 925 applied to the front of the tubing 922, wherein masks 925 are of a second color. For example, the stripe of the visual marker 920 may be red and the mask 925 may be white. A limitation of the radially-asymmetric embodiment described in FIG. 26 is that the user must rotate the tubing 922 until the visual marker 920 is aligned with axis A to provide the proper viewing angle. This use of the term 'pattern' means arrangement of a plurality of markers (e.g. a plurality of stripes). The visual markers 920 may be opaque, translucent, or reflective. In some embodiments, the markers 920 may be simple, such as a straight, longitudinal stripe having a uniform width and thickness. In other embodiments, the markers 920 may be complex, such as shapes that are non-uniform or irregular in width or thickness or a repeated design or form.

Figure 27:
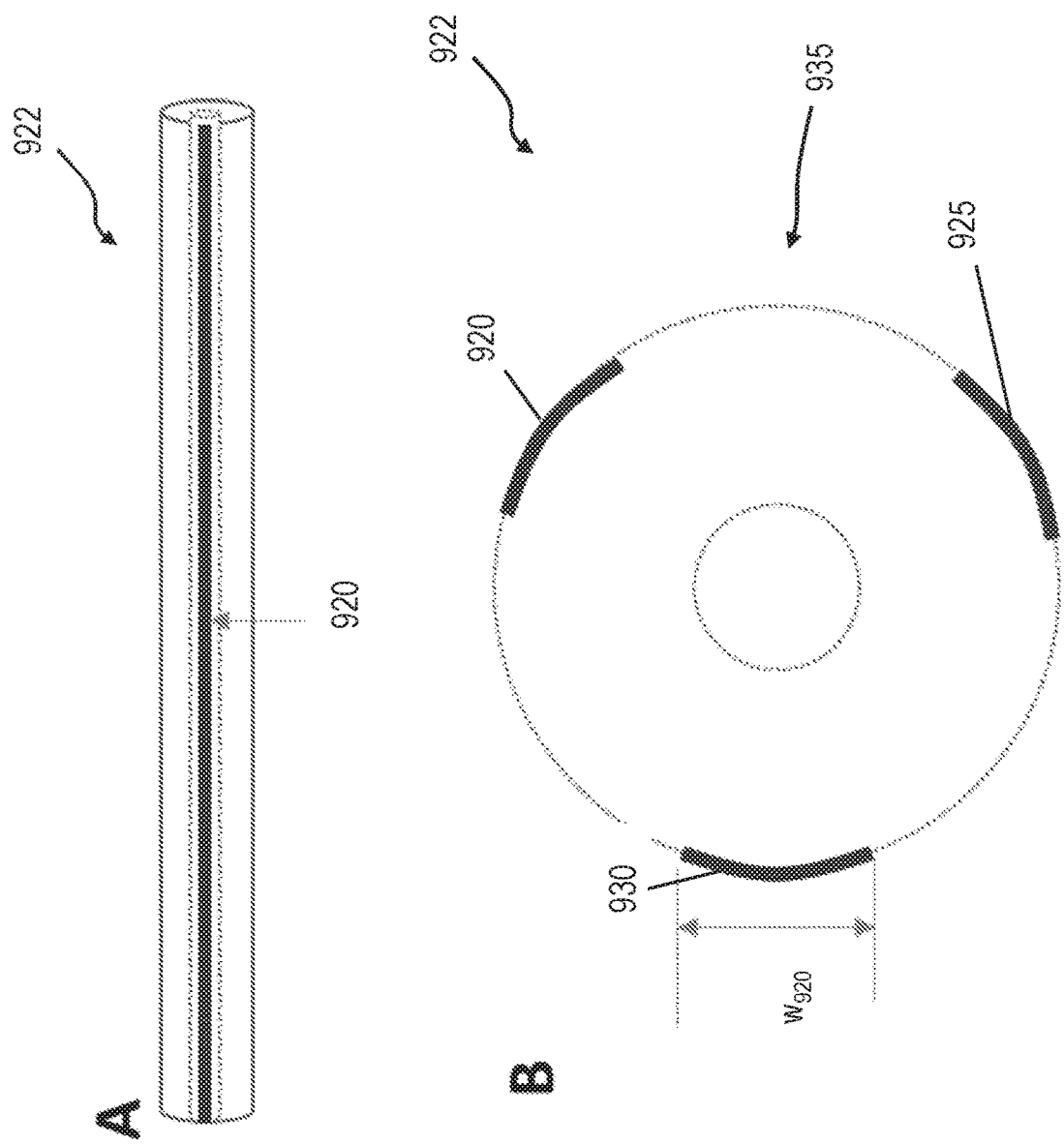
FIG. 27 shows a top view and a perspective view of the tubing of the present disclosure having a radially symmetric pattern of visual markers where the number of markers $N_m=3$.

In some embodiments, the pattern 935 on the tubing is radially symmetric, and may be referred to interchangeably herein as radially symmetric wall patterning. This symmetric pattern 935 provides the user with flexibility because the proper viewing angle may be achieved at more than one position. An exemplary symmetric pattern 935 according to the present disclosure is shown in FIG. 27. Pattern 935 includes first marker 920, second marker 925, and third marker 930, each disposed about 120 degrees apart on tubing 922. In other words, markers 920, 925, and 930 are radially and symmetrically disposed about tubing 922.

In some embodiments, and as shown in FIG. 27, markers 920, 925, and 930 are identical. For example, markers 920, 925, and 930 may be the same width and color. In other embodiments, markers 920, 925, and 930 have at least one distinguishing feature, such as width and/or color. For example, marker 920 may have a first width, marker 925 may have a second width, and marker 930 may have a third width. In some embodiments, the second width and the third width are about equal, and the first width is different from the second and third widths. In another example, marker 920 may have a first color, marker 925 may have a second color, and marker 930 may have a third color, wherein the second and third colors are the same and the first color is different from the second and third colors.

Figure 28:
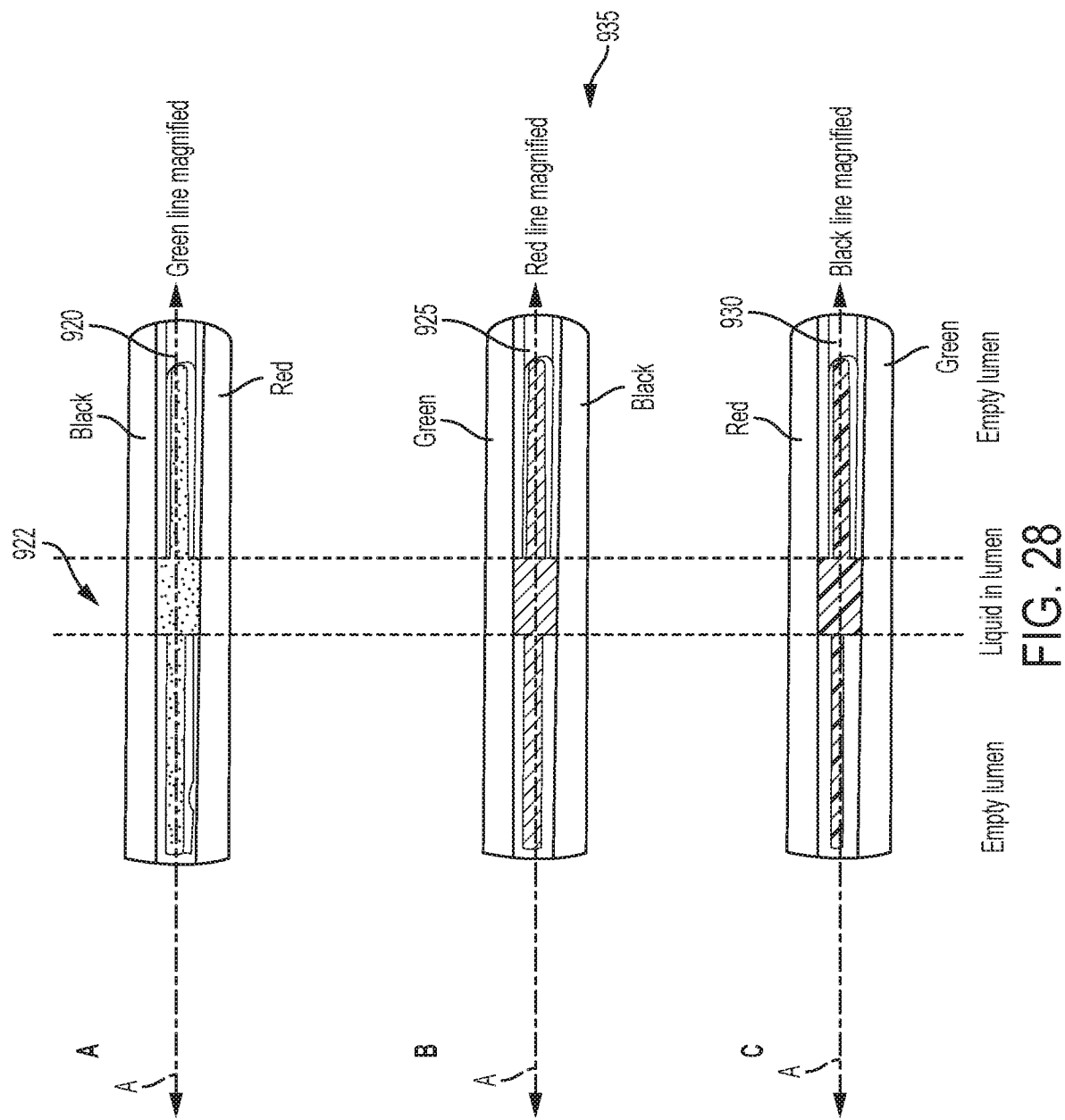
FIG. 28 is a top view of a tubing of the present disclosure having a radially symmetric pattern, wherein the markers are each of a different color.

In another exemplary embodiment, and as shown in FIG. 28, markers 920, 925, and 930 each have the same width, are symmetrically and radially disposed, but each of markers 920, 925, and 930 have a different color. For example, marker 920 may be a green longitudinal stripe, marker 925 may be a red longitudinal stripe, and marker 930 may be a black longitudinal stripe. Any three distinguishable colors may be used. In addition, it is understood that while colors are used in the present examples, distinguishing markings, patterns, or contours may also be used in place of color and or in conjunction with color. Again, the three optical effects as detailed above are produced, namely (a) primary magnified images through the lumen, (b) reflections at the lumen/cladding interface, and (c) secondary images are observed when using an embodiment that has multiple stripes. In the example of FIG. 28, the masking of the secondary reflections is preferably done with stripes of different colors. For example, a three-stripe embodiment might use three different colors for the stripes. In this way, the primary image may be easily distinguished from the masking stripes. Tubing 922 of FIG. 28 shows three views, rotated 120 degrees apart, the tubing 922 having an outer diameter of 12.7 mm (0.5"). Tubing 922 is applied with three differently-colored parallel longitudinal stripes 920, 925, 930. In the top view of FIG. 28, tubing 922 is rotated so that the green marker/stripe 920 is at back (and aligned with longitudinal axis A) and is magnified by a central, liquid-filled portion of the lumen. In the middle view of FIG. 28, tubing 922 is rotated so that the red marker/stripe 925 is at back (and aligned with longitudinal axis A) and is magnified by the central, liquid-filled portion of the lumen. In the bottom view of FIG. 28, tubing 922 is rotated so that the black marker/stripe 930 is at back (and aligned with longitudinal axis A) and is magnified by the central, liquid-filled portion of the lumen. In the example of FIG. 28, each of the markers 920, 925, and 930 may be used as visual markers together or interchangeably.

Radially asymmetric patterns (as in FIG. 26) or radially symmetric patterns (as in FIG. 28) may vary in the number, width, color, and other feature of the visual markers (e.g., stripes). Although any number of markers may be envisioned for a pattern according to the present disclosure, the radially-symmetric patterns may advantageously include an odd number of markers. For radially-symmetric designs, it will usually be advantageous to have an odd number of lines (1, 3, 5, 7, etc.) so that at any given viewing angle a stripe will be aligned at 180 degrees with a viewing window as will be discussed in further detail below.

FIGS. 29-32 are cross-sectional views of exemplary radially symmetric patterns for tubing 1022. Each pattern includes a plurality of markers 1020, wherein each marker 1020 has a uniform width $w_1$ and a window 1070 disposed between each marker 1020, wherein each window also has a uniform width $w_2$, wherein $w_1$ and $w_2$ may be the same or different. For example, the tubing 1022 of FIG. 29 includes three markers 1020 having width $w_1$ and three windows 1070 having width $w_2$ disposed therebetween. The number of markers 1020 is represented by $N_m$ wherein each marker 1020 is distributed radially $[360/N_m]$ degrees relative to the longitudinal axis A and along the exterior circumferential wall 1010 of tubing 1022. In the example of FIG. 29, tubing 1022 has three markers 1020 ($N_m$=3) disposed [360/3] or 120 degrees apart. In the example of FIG. 30, tubing 1022 has five markers 1020 ($N_m$=5) disposed [360/5] or 72 degrees apart. In the example of FIG. 31, tubing 1022 has six markers 1020 ($N_m$=6) disposed [360/6] or 60 degrees apart. In certain embodiments, particularly when tubing 1022 has an even number of markers 1020, the markers 1020 may have different color, reflectivity, translucency, and/or opacity. In the example of FIG. 32, tubing 1022 has three markers 1020 ($N_m$=3) disposed [360/3] or 120 degrees apart, and each marker 1020 is of a different color (similar to FIG. 28).

FIGS. 33-36 are cross-sectional views of exemplary radially asymmetric patterns for tubing 1122. Each pattern includes at least one marker 1120 having a width $w_3$ and at least one window 1170 having a width $w_4$. In the example of FIG. 33, tubing 1122 has a single marker 1120 and a single window 1170 for viewing. In the example of FIG. 34, tubing 1122 has a visual marker 1120 and further includes two flanking or masking markers 1165 disposed on either side adjacent to marker 1120, and a window 1170 for viewing. In the example of FIG. 35, tubing 1122 has a visual marker 1220 formed by the absence of a marker or stripe and further includes two flanking or masking markers 1265 disposed on either side adjacent to marker 1220, and a window 1270 for viewing. In the example of FIG. 36, tubing 1122 has three markers 1120a, 1120b, 1120c ($N_m$=3) of different colors, different widths, and disposed radially non-uniformly about tubing exterior 1110. Such radially asymmetric patterns may include any number of markers and windows of various widths, and markers may have various colors, opacities, and reflectivity.

Pattern Optimization. As illustrated in FIGS. 29-36, radially symmetric patterns and radially asymmetric patterns are printed-on or embedded-in the exterior walls of the simple tubings 1022, 1122, 1222, and may be of varying number, width, color, etc. Advantageously, patterns including non-limiting examples of longitudinal markers or stripes 1020, 1120, 1220, are useful because the patterns can be extruded with the tubing 1022, 1122, 1222, while providing imaging windows 1070, 1170, 1270, along the full length of the tubing 1022, 1122, 1222.

In another exemplary embodiment according to the present disclosure, such patterns can be optimized to take advantage of one or more of the above-described optical effects that have been disclosed, particularly the magnification effect and the reflection at the cladding/lumen interface, while limiting undesirable secondary imaging effects. In particular, it is an advantage of a radially asymmetric design that patterns can be placed at any desired radial location to optimize the desired optical effects (e.g., magnification of the primary image, and reflections that depend upon the state of the lumen), and to reduce or eliminate undesired optical effects (e.g., secondary images formed by the tube cladding). Radially symmetric designs may be more limited to ensure symmetry, but considerable optimization can still be done to maximize the desired optical effects.

I. Optimization of Marker Size.

Figure 37:
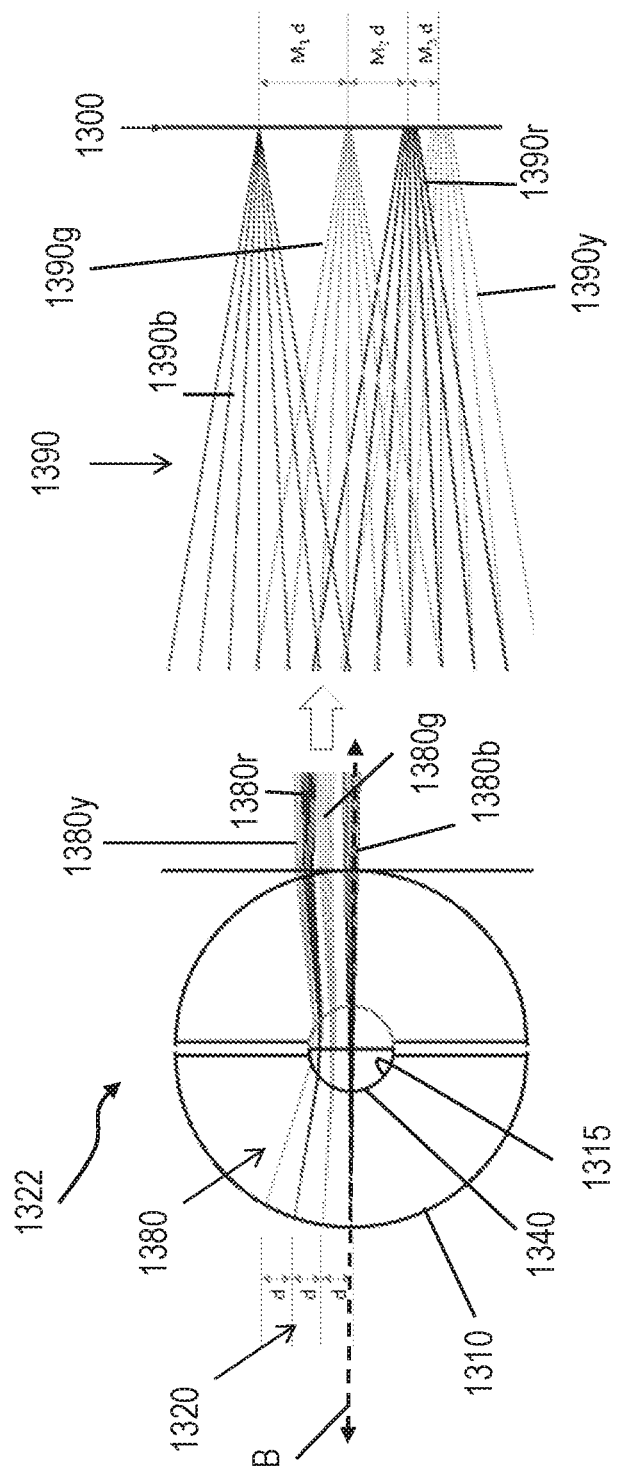
FIG. 37 illustrates a ray-trace diagram of a top portion for a tubing of the present disclosure showing the magnification optical effect, wherein the tubing itself is used as an imaging lens.

To optimize the magnification optical effect, wherein the tubing 1322 itself is used as an imaging lens, a visual marker 1320 with a contrasting color may be positioned directly opposite the image plane 1300 of the viewer's eye 300. FIG. 37 schematically illustrates a ray-trace through a cross-section of an exemplary tubing 1322 having an outer diameter of 1.6 mm and an inner diameter of 0.38 mm, having a filled lumen 1340, and the corresponding rays at the image plane of the viewer's eye 300. Optical rays from the visual marker 1320 are separated from each other, normal to the main axis B by distance "d". Rays 1380 pass through the lumen 1340, propagate to the eye 300 along paths 1390, and impinge upon the eye 300, where they appear magnified. In the model according to FIG. 37, only rays 1380 on the upper portion of the cross-section are shown; however, it is understood that mirror-image rays could be shown on the bottom portion of the cross-section. FIG. 37 illustrates that the magnification of marker 1320, or ratio of true object size to image size, is not constant. As the marker 1320 is moved further off-axis B, the magnification is reduced, and vice versa. In FIG. 37, rays 1380 (blue 1380b, green 1380g, red 1380r, and yellow 1380y) from marker 1320 are separated by distance "d". When they are imaged by the eye 300, the blue rays 1390b are separated from the green rays 1390g by a distance Mid, the green rays 1390g are separated from the red rays 1390r by a distance $M_2$d, and the yellow rays 1390y are separated from the red rays 1390r by a distance $M_3$d, where $M_3$d<$M_2$d<$M_1$d. The farther off-axis B that object 1320 is, the less pronounced will be the difference in magnification between the filled and empty states of the lumen 1340. Therefore, in order to maximize the difference in magnification between the filled and unfilled states of the tube 1322, the size of the marker 1320 should be optimized.

Figure 38:
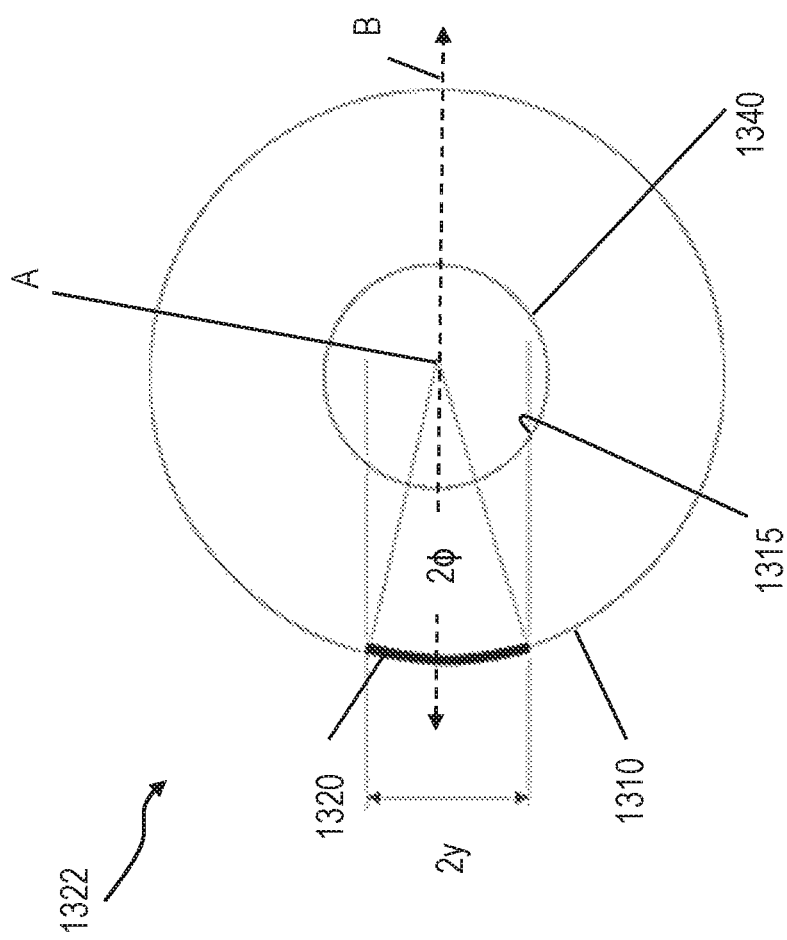
FIG. 38 is a cross-sectional view showing marker width as a function of angular extent for a tubing of the present disclosure.

Generally, for simple tubing 1322 having concentric exterior and interior walls 1310, 1315, as shown in FIGS. 37 and 38, and having a lumen 1340 filled with a medium of lower index of refraction than that of the tubing 1322, there is an approximately linear relationship between the size of the marker 1320 and the apparent size of the magnified image, which may be used to establish bounds on the optimal size of marker 1320. The linear magnification relationship approximation is valid so long as the chief ray from the outer edge of the marker 1320 traverses the lumen 1340 within its "clear aperture", meaning the area of the tubing 1322 over which the desired optical performance is achieved.

In FIG. 38, marker 1320 has a total vertical extent or width (2y, where y is measured vertically from main axis B which is perpendicular to longitudinal axis A) and a total angular extent (2φ, where φ is also measured relative to main axis B). In this example, the maximum clear aperture ($A_{max}$) of the lumen 1340 is about 90% of its diameter ($D_L$, where $D_L$=$2R_L$). Beyond this 90% limit, optical aberrations and the physical edge of the lumen 1340 may act to limit the size of the image viewed by a user's eye 300 (FIG. 37). That is, the perceived size of the marker 1320 saturates and ceases to increase in size, even if the size of marker 1320 is increased. Additionally, portions of the visual marker 1320 can also be viewed through the imaging path around the lumen 1340. As a result, the images of the visual marker 1320 may appear to fill the entire inner diameter and potentially outer diameter of the tubing 1322. Therefore, in the example of FIG. 38, the maximum vertical extent ($2y_{max}$) of marker 1320 may be defined as the point when the chief ray from the outer edge of the marker 1320 intersects the lumen 1340 at the edge of the clear aperture ($A_{max}$), such that $2y_{max}$=$A_{max}D_L$=$0.9D_L$ (or $y_{max}$=$0.9R_L$).

Discernment of smaller markers 1320 is possible; however, the marker 1320 must be large enough that the magnified image can be observed by a user 1300 with typical visual acuity. If the marker 1320 is too narrow, the difference will be difficult to perceive regardless of filling medium because any image formed of the marker 1320 would still be very small. In the example of FIG. 38, the minimum vertical extent ($2y_{min}$) of visual marker 1320 may be defined as $2y_{min}$=$A_{min}D_L$=$0.25D_L$ (or $y_{min}$=$0.25R_L$).

Based on the above teachings, the total vertical extent (2y) of visual marker 1320 may be selected according to Equations 1a and 1b below. Equations 1a and 1b set forth an optimal range for the vertical extent (2y) of visual marker 1320 on the outer circumferential surface 1310 of the tubing 1322.

$$0.25D_L < 2y < 0.9D_L \quad \text{Equation 1a}$$

$$0.25R_L < y < 0.9R_L \quad \text{Equation 1b}$$

The design of tubing 1322 and lumen 1340 may be constrained by the Lens-Maker's Formula, as shown in Equation 2 below.

$$0.5 < \frac{R_T(n_T - n_L)}{R_L(n_T - 1)} < 1.5 \quad \text{Equation 2}$$

wherein:
R_T=outer radius of tubing;
R_L=radius of lumen;
n_T=index of refraction of tubing; and
n_L=index of refraction of the filling medium within the lumen.

The index of refraction within the lumen $n_L$ will be greater (and closer to the index of refraction of the tubing $n_T$) when the lumen 1340 contains a liquid drug product ($n_L$=about 1.33) than when the lumen 1340 contains air ($n_L$=1.0). As a result, the overall optical power of the tubing 1322, which is a function of ($n_T$−$n_L$), will be lower when the lumen 1340 contains the liquid drug product than when the lumen 1340 contains air.

Within the constraints of Equations 1b and 2, the angular extent (2ϕ) of visual marker 1320 may be approximated according to Equation 3 and confirmed using ray tracing.

$$0 = R_T\sin\phi + \theta_p\left(R_L\sqrt{1-A^2} - R_T\cos\phi\right) - AR_L, \quad \text{Equation 3}$$

$$\theta_p = \phi - \sin^{-1}\left(\frac{\sin(\phi)}{n_T}\right)$$

wherein y=AR_L.

II. Optimization of Differential Reflections.

Patterns for marking the outer circumferential surface of the tubing according to embodiments of the present disclosure may also be optimized by maximizing the difference between the reflections that occur at the lumen/cladding interface in the filled and unfilled states. As previously illustrated in FIG. 21, the reflection coefficient at the lumen/cladding interface depends upon the medium in the lumen (e.g., air and/or liquid drug product). By taking into account the reflections at the lumen/cladding interface, marker width for the pattern can be optimized to afford maximum visual contrast. Typically, the markers or stripes are printed-on, or embedded-in the outer circumferential surface of the tube cladding, and are uniform along the length of the tube.

In the illustrated embodiment of FIGS. 39 and 40, tubing 1422 is shown with a visual marker 1420 having a total vertical extent (2y, where y is measured vertically from main axis B which is perpendicular to longitudinal axis A) and a total angular extent (2φ, where φ is also measured relative to main axis B). Tubing 1422 also includes optional masks 1465 for restricting the illumination of the back wall, to enhance the contrast obtained by differentially reflected light rays. Marker 1420, masks 1465, and windows 1470 are positioned on the outer circumferential surface 1410 of tubing 1422 so as to permit passage of rays of light that are differentially reflected at the lumen/cladding interface depending upon whether the lumen 1450 is filled (e.g., contains liquid drug product) or unfilled (e.g., contains air). As shown in FIG. 40, incident rays of light 1480g (green), 1480b (blue), 1480r (red), pass through at least one window 1470 toward the inner circumferential surface 1415 that defines lumen 1450. In this particular embodiment, the incident rays contact the inner circumferential surface 1415 at the following angles (measured relative to a line perpendicular to the inner circumferential surface 1415): 42.6° for 1480r (red), 52.3° for 1480b (blue), and 62.4° for 1480g (green). The reflected rays 1490g (green), 1490b (blue), 1490r (red) then exit through at least one window 1470 to be viewed by the user's eye 300. The incident rays 1480r (red) and 1480g (green) correspond to the "critical angle" when the lumen is filled with a red medium that reflects rays 1490r (red) and/or a green medium that reflects rays 1490g (green), respectively. The critical angle is the angle of incidence beyond which light rays are completely reflected from a lumen/cladding interface. To maximize the difference in reflected light between the filled and unfilled lumen states, these rays should be allowed to pass through a transparent window 1470, while other areas of the tube may be covered with masks 1465, for example. For a given geometry and filling media, the angular extent of the transparent windows 1470 can be found by calculating the critical angles and then finding the intersection points between the corresponding chief rays and the masking surface 1465. It is noted that in the model illustrated in FIG. 40, only rays 1480 and 1490 are shown for the top portion of the cross-section of tubing 1422, however, it is understood that the mirror-image of the rays could be shown on the bottom portion of the cross-section.

III. Optimization of Radially Asymmetric Patterns.

Figure 41:
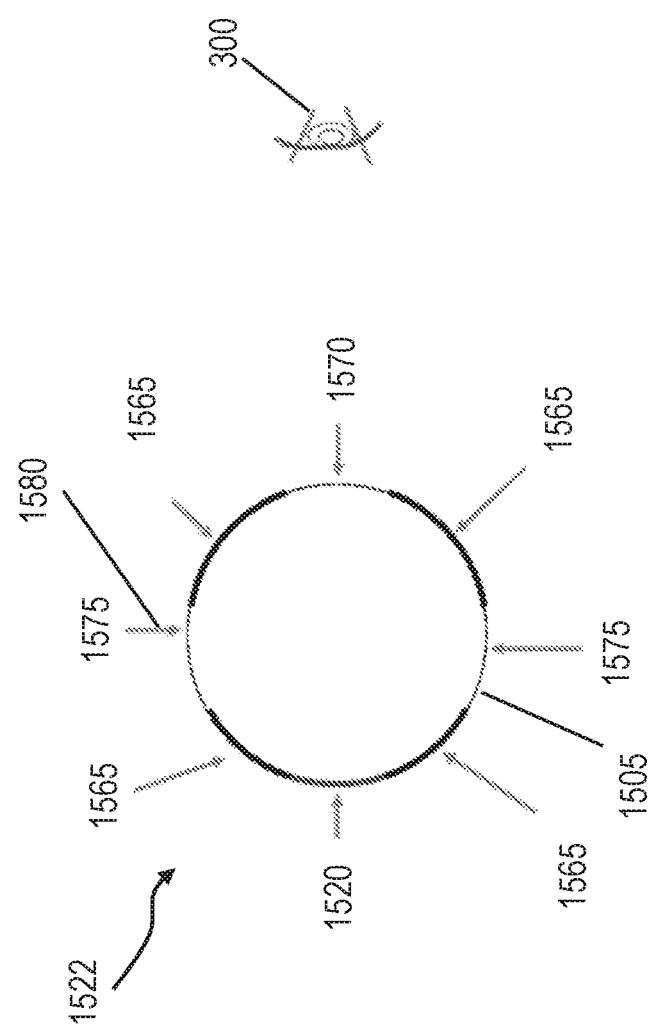
FIG. 41 is a schematic view of a radially asymmetric pattern for optimization of magnification and reflection optical effects according to the present disclosure.

An exemplary tubing 1522 with an optimized asymmetric design is illustrated in FIG. 41. Tubing 1522 has an outer circumferential surface 1505 with a visual marker 1520 positioned at about −18°<ϕ<18° and four opaque masks 1565 positioned at about 18°<ϕ<60°, 100°<ϕ<160°, −18°<ϕ<−60°, and −100°<ϕ<−160°. Between marker 1520 and masks 1565, outer circumferential surface 1505 may include transparent windows 1575, which permit rays 1580 of light to enter tubing 1522 and contribute to the differential reflection (as shown in FIG. 40). The reflected rays then exit through at least one viewing window 1570 to be viewed by the user's eye 300 (as shown in FIG. 40).

IV. Optimization of Radially Symmetric Patterns.

Figure 42:
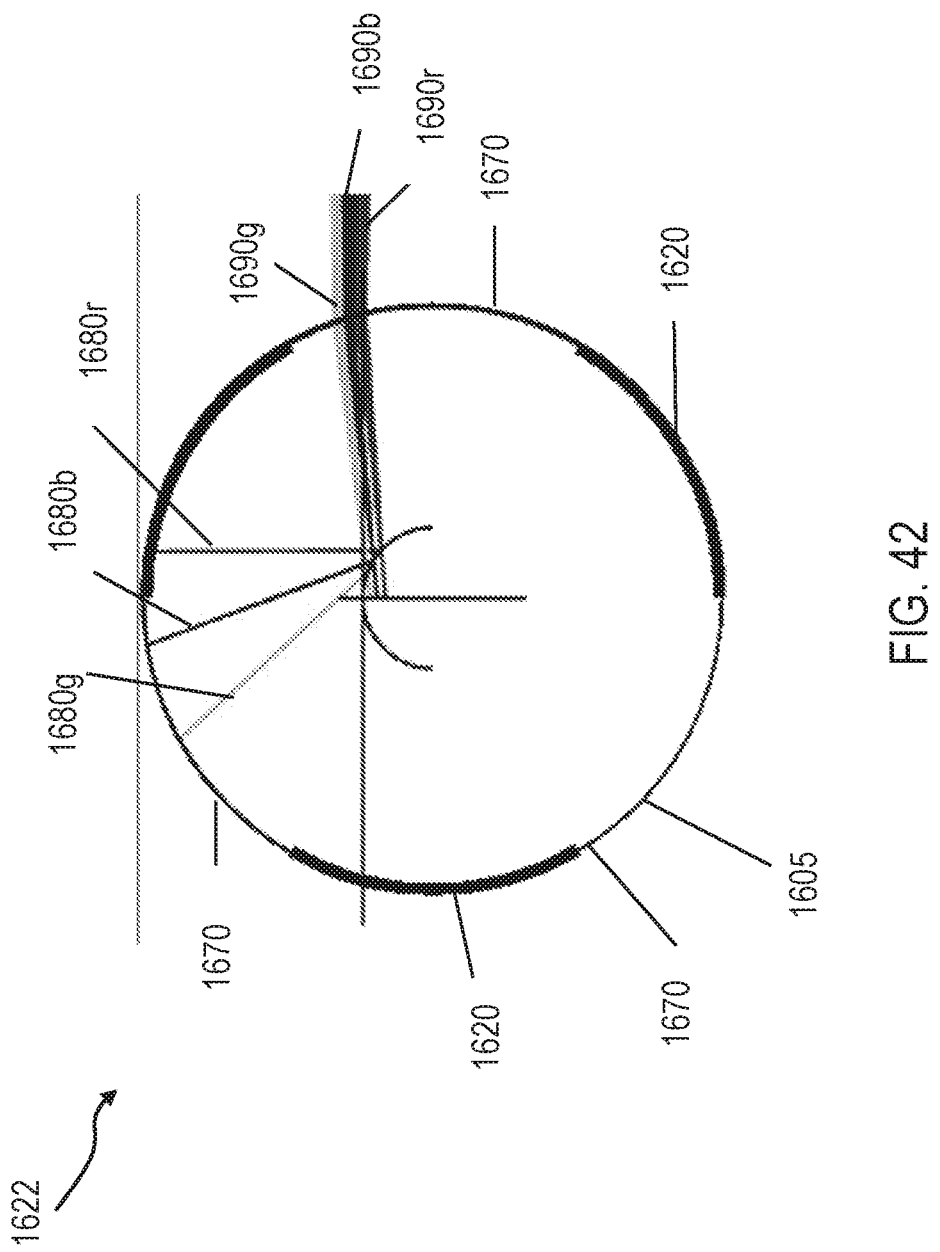
FIG. 42 is a ray-trace diagram for a tubing of the present disclosure having a radially symmetric pattern.

An exemplary tubing 1622 with an optimized symmetric design is illustrated in FIG. 42. Tubing 1622 has an outer circumferential surface 1605 with three opaque visual markers 1620 ($N_m$=3), and three transparent windows 1670 disposed therebetween, with each marker 1620 and window 1670 having an equal angular extent of about 60°. FIG. 42 includes a ray-trace diagram showing incident rays 1680r (red), 1680b (blue), and 1680g (green) and exiting rays 1690r (red), 1690b (blue), and 1690g (green). These rays are shown for the top portion of the cross-section of tubing 1622; however, it is understood that the mirror-image of the rays could be shown on the bottom portion of the cross-section.

Another exemplary tubing 1722 with an optimized symmetric design is illustrated in FIG. 43. Tubing 1722 has an outer circumferential surface 1705 with five opaque visual markers 1720 ($N_m$=5), each having a first angular extent ($\phi_{1720}$), and five transparent windows 1770 disposed therebetween, each having a second angular extent ($\phi_{1770}$). In this embodiment, the angular extents $\phi_{1720}$ and $\phi_{1770}$ are not equal. Specifically, each angular extent $\phi_{1720}$ is about 30° and each angular extent $\phi_{1770}$ is about 42°. FIG. 43 includes a ray-trace diagram showing incident rays 1780r (red), 1780b (blue), and 1780g (green) and exiting rays 1790r (red), 1790b (blue), and 1790g (green). These rays are shown for the top portion of the cross-section of tubing 1722; however, it is understood that the mirror-image of the rays could be shown on the bottom portion of the cross-section.

Another exemplary tubing 1822 with an optimized symmetric design is illustrated in FIG. 44. Tubing 1822 has an outer circumferential surface 1805 with three opaque visual markers 1820 ($N_m$=3), each having a first angular extent ($\phi_{1820}$), and three transparent windows 1870 disposed therebetween, each having a second angular extent ($\phi_{1870}$). In this embodiment, the angular extents $\phi_{1820}$ and $\phi_{1870}$ are not equal. Specifically, each angular extent $\phi_{1820}$ is about 30° and each angular extent $\phi_{1870}$ is about 90°. FIG. 44 includes a ray-trace diagram showing incident rays 1880$r$ (red), 1880$b$ (blue), and 1880$g$ (green) and exiting rays 1890$r$ (red), 1890$b$ (blue), and 1890$g$ (green). These rays are shown for the top portion of the cross-section of tubing 1822; however, it is understood that the mirror-image of the rays could be shown on the bottom portion of the cross-section.

In other embodiments according to the present disclosure, rather than being a continuous, solid longitudinal stripe along the longitudinal axis of the tubing, the visual marker may be discontinuous or vary along the longitudinal axis of the tubing. A continuous visual marker may have a "fill factor" of 1, whereas a discontinuous visual marker may have a "fill factor" less than 1. The fill factor may be calculated by dividing the area filled by the marker by the total area.

Figure 45:
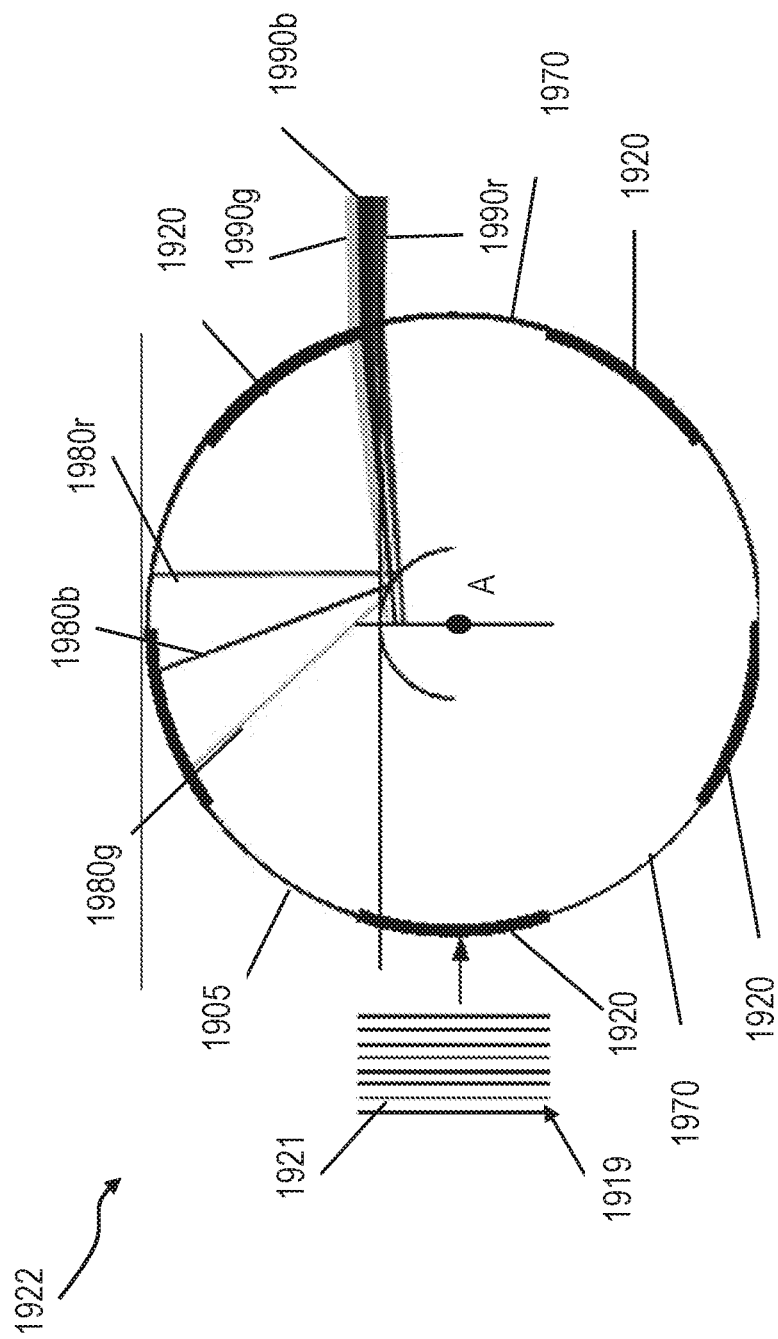
FIG. 45 is a ray-trace diagram for tubing similar to that as shown in FIG. 43 except that the longitudinal visual marker is discontinuous.

An exemplary tubing 1922 with a discontinuous visual marker 1920 is illustrated in FIG. 45. When tubing 1922 is viewed radially in FIG. 45, each visual marker 1920 on outer circumferential surface 1905 includes a series of partially circumferential lines 1921 separated longitudinally by spaces 1919, similar in appearance to a bar code. In this embodiment, marker 1920 may have a fill factor of about 0.1 to about 0.3, for example, but this fill factor may vary. When tubing 1922 is viewed in cross-section in FIG. 45, outer circumferential surface 1905 of tubing 1922 includes five visual markers 1920 ($N_m$=5), each having an angular extent of about 36°. The vertical extent and angular extent of the markers 1920 may be determined as discussed above. FIG. 45 includes a ray-trace diagram showing incident rays 1980$r$ (red), 1980$b$ (blue), and 1980$g$ (green) and reflected rays 1990$r$ (red), 1990$b$ (blue), and 1990$g$ (green). These rays are shown for the top portion of the cross-section of tubing 1922; however, it is understood that the mirror-image of the rays could be shown on the bottom portion of the cross-section. The discontinuous markers 1920 of FIG. 45 may allow illuminating light rays 1980$b$ and 1980$g$ (which would be blocked by a fully opaque marker) to pass relatively unobstructed to the user's eye via the corresponding reflected light paths 1990$b$ and 1990$g$. Additionally, the magnified image of the opaque parts of marker 1920 may fill the spaces 1919 between the lines 1921 of marker 1920, providing an additional optical change that can be observed by the user.

V. Tubes with Complex Geometries to Enhance Magnification Optical Effect.

The optical effects described above relate to simple tubing having a circular cross section, a concentric lumen, and radially symmetric patterns or radially asymmetric patterns imprinted or embedded into the outer circumferential surface of the tubing. Such designs are attractive because of simplicity in manufacturing and usefulness as infusion set tubes, and because the tubes are small. However, other geometries of the tubing and/or the lumen can also be used to maximize the visual differences between a filled and unfilled lumen for ease of visualization for the user and discernment to the user's eye.

Oval-Shaped or Slot-Shaped Lumen Designs.

In yet other embodiments of the present disclosure, tubing having circular cross-sections includes a lumen extending asymmetrically in one direction to provide a slot-shaped or oval-shaped lumen in cross-section. The slot-shaped or oval-shaped lumen can be useful for improving the performance of the differential magnification effect.

FIGS. 65 and 66 illustrate tubing 2722 including a slot-shaped lumen 2740 having major diameter $a_{2720}$ and minor diameter $b_{2720}$. Tubing 2722 also has a visual marker 2720 which will be differentially magnified by the eye 300 of the observer, as similarly described above. Marker 2720 is applied to tubing 2722 so that the width $w_{2720}$ of marker 2720 is parallel to the major diameter $a_{2720}$ of the lumen 2740 and perpendicular to the minor diameter $b_{2720}$ of the lumen 2740. Because the major diameter $a_{2720}$ of the lumen 2740 is oriented to fill more space between the visual marker 2720 and the eye 300 of the user, the image of the marker 2720 will occupy a greater part of the resulting image, while any undesirable secondary images, which pass exclusively through the cladding, will be reduced. Because lumen 2740 is elongated in the same direction as the width $w_{2720}$ of marker 2720, width $w_{2720}$ can also be made somewhat larger than in the simple tube embodiments, for example, as shown in FIGS. 15-45. Advantageously, this size flexibility makes manufacturing the marker 2720 easier.

In the embodiment illustrated in FIGS. 67 and 68, tubing 2822 has an oval-shaped lumen 2840 having major diameter $a_{2820}$ and minor diameter $b_{2820}$. In this case, however, tubing 2822 is optimized to improve the performance of the reflective effect, and marker 2820 is applied to tubing 2822 so that the width $w_{2820}$ of marker 2820 is parallel to the minor diameter $b_{2820}$ of the lumen 2840 and perpendicular to the major diameter $a_{2820}$ of the lumen 2840. The size and shape of the oval lumen 2840 may be optimized to provide a maximum set of differentially reflected light rays.

The improved optical performance provided by a slot-shaped lumen 2740 or oval-shaped lumen 2840, for example, should be balanced by a desire to maintain small fill-volumes and low pressure-drops across the length of the corresponding tubing 2722, 2822. With respect to tubing 2722 of FIGS. 65 and 66 designed for an insulin infusion set, for example, the major diameter $a_{2720}$ may be about 0.75 mm and the minor diameter $b_{2720}$ may be about 0.2 mm. In this example, the volume required to fill the lumen 2740 of the tubing 2722 is about 25% more as compared with a standard tubing having a 0.38 mm diameter circular lumen, with any pressure drop along the length of the tubing 2722 expected to be similar to that of the standard tubing.

Thermometer Design.

Figure 46:
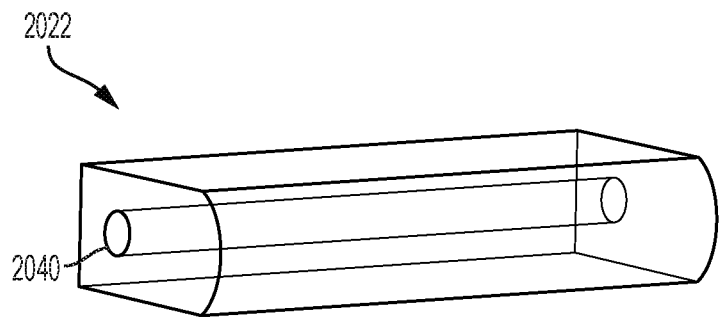
FIG. 46 is a perspective, isometric view of a portion of tubing of the present disclosure having 'thermometer' geometry.
Figure 47:
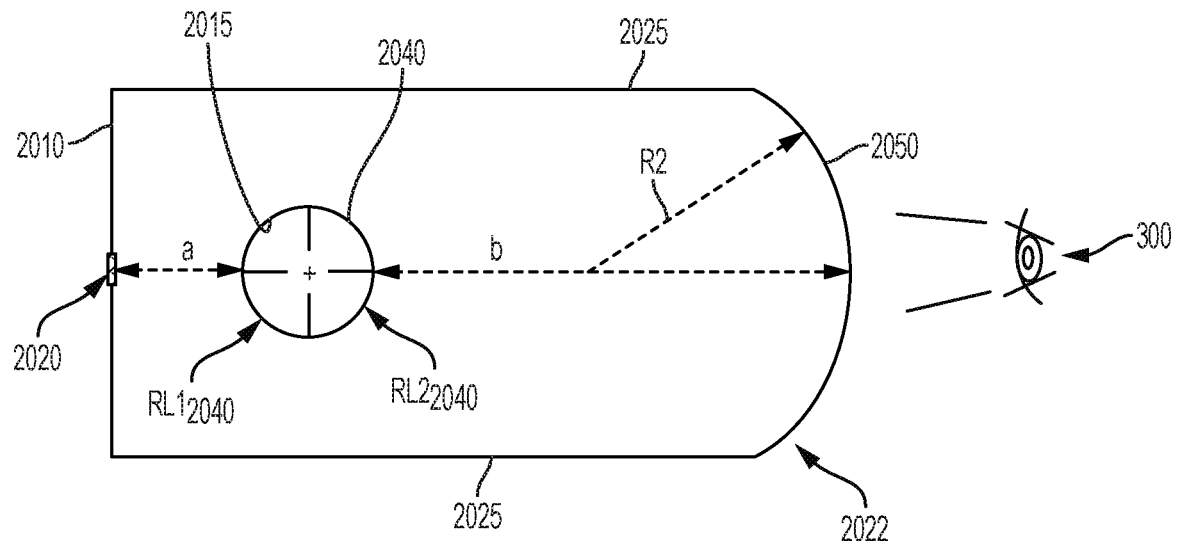
FIG. 47 is a cross-sectional view of the tubing of FIG. 46.

In another exemplary embodiment according to the present disclosure, complex tubing 2022 as illustrated in FIGS. 46-47 utilizes a tubing geometry to enhance the difference in magnification optical effects that occur when the lumen is filled versus unfilled. FIG. 46 is a perspective, isometric view of a portion of tubing 2022 having lumen 2040 designed to enhance the difference in image magnification between filled and unfilled conditions, while FIG. 47 illustrates a corresponding cross-section of tubing 2022. Tubing 2022 having the so-called 'thermometer' geometry creates a greater magnification optical effect when the lumen 2040 is filled (e.g., contains liquid drug product) and a lessor magnification optical effect when the lumen 2040 is unfilled (e.g., contains air). Tubing 2022 has a primary lens 2050 through which a user's eye 300 views lumen 2040. Lens 2050 has a curvature (1/R2) and is positioned distance "b" from lumen 2040 to provide a focal length of the formed lens 2050 that is equal to the optical thickness of the tubing 2022 when the lumen 2040 is filled with the higher density medium (e.g., liquid drug product). Because lumen 2040 is surrounded by a higher index material (e.g., plastic), lumen 2040 will act as a negative lens and modulate the overall effective focal length of the tubing 2022 and the consequent magnification. Tubing 2022 also has a visual marker 2020 on a far wall 2010, which is positioned at distance "a" from lumen 2040. The lumen 2040 may be positioned closer to the far wall 2010 than the lens 2050, such that a<b. This arrangement may maximize the magnification and minimize aberrations and/or ray paths that do not intersect the side walls 2025. While the lumen 2040 of FIG. 47 has a simple circular cross-section having a radius of curvature $RL1_{2040}=RL2_{2040}$, other variants are contemplated including a lumen 2040 having a non-circular cross-section and/or having different radii of curvature (RL1, RL2) on the left and right sides so that $RL1_{2040}$ is not equal to $RL2_{2040}$.

Figure 48:
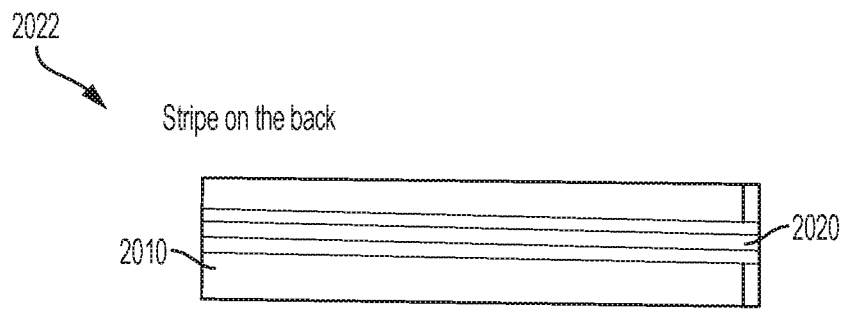
FIGS. 48-50 shows photographic view from the back (FIG. 48), side (FIG. 49), and front (FIG. 50) of the tubing of FIGS. 46-47.
Figure 49:
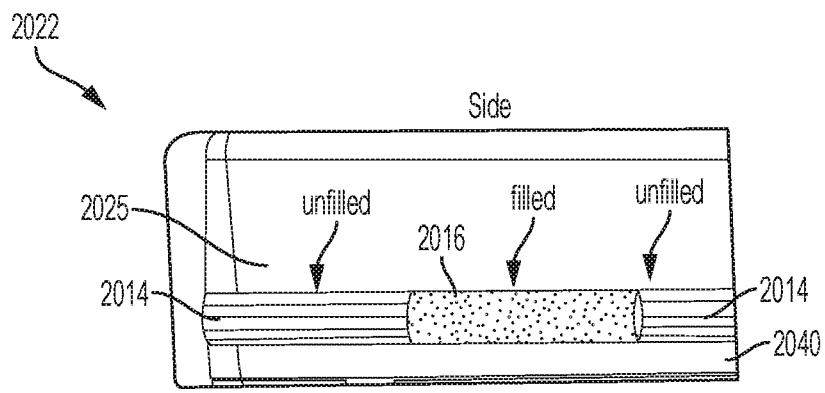
Figure 50:
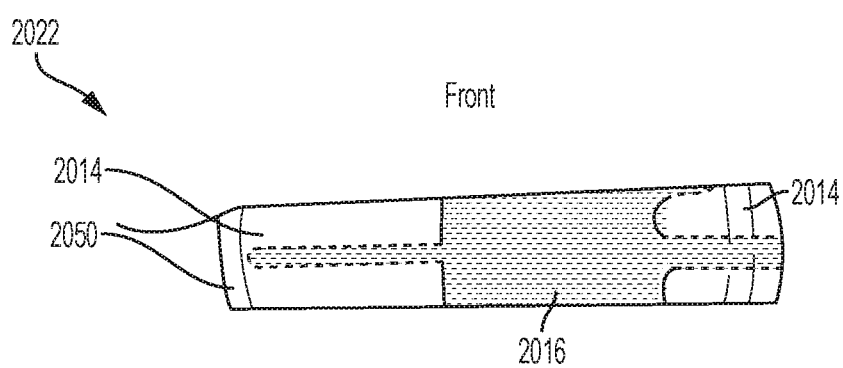

An exemplary embodiment of tubing 2022 is shown in FIGS. 48-50. Tubing 2022 has an outer diameter of 9.525 mm (0.375" O.D.) and an inner diameter of 2.286 mm (0.090" I.D.), wherein the outer diameter corresponds to the sum of the distances a+b+RL1+RL2 according to FIG. 47 and the inner diameter corresponds to the diameter of lumen 2040. When lumen 2040 is viewed through a side wall 2025 in FIG. 49, unfilled portions 2014 and filled portions 2016 of lumen 2040 must be distinguished directly without the aid of marker 2020. However, when lumen 2040 is viewed through lens 2050 in FIG. 50, marker 2020 is more magnified for filled portions 2016 than for unfilled portions 2014.

Wide Angle Thermometer Design.

Figure 51:
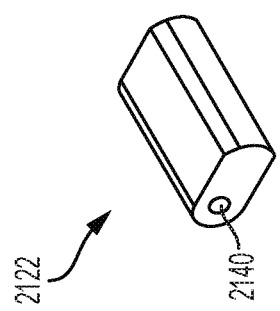
FIG. 51 is a perspective, isometric view of a portion of tubing of the present disclosure having wide-angle thermometer geometry.
Figure 52:
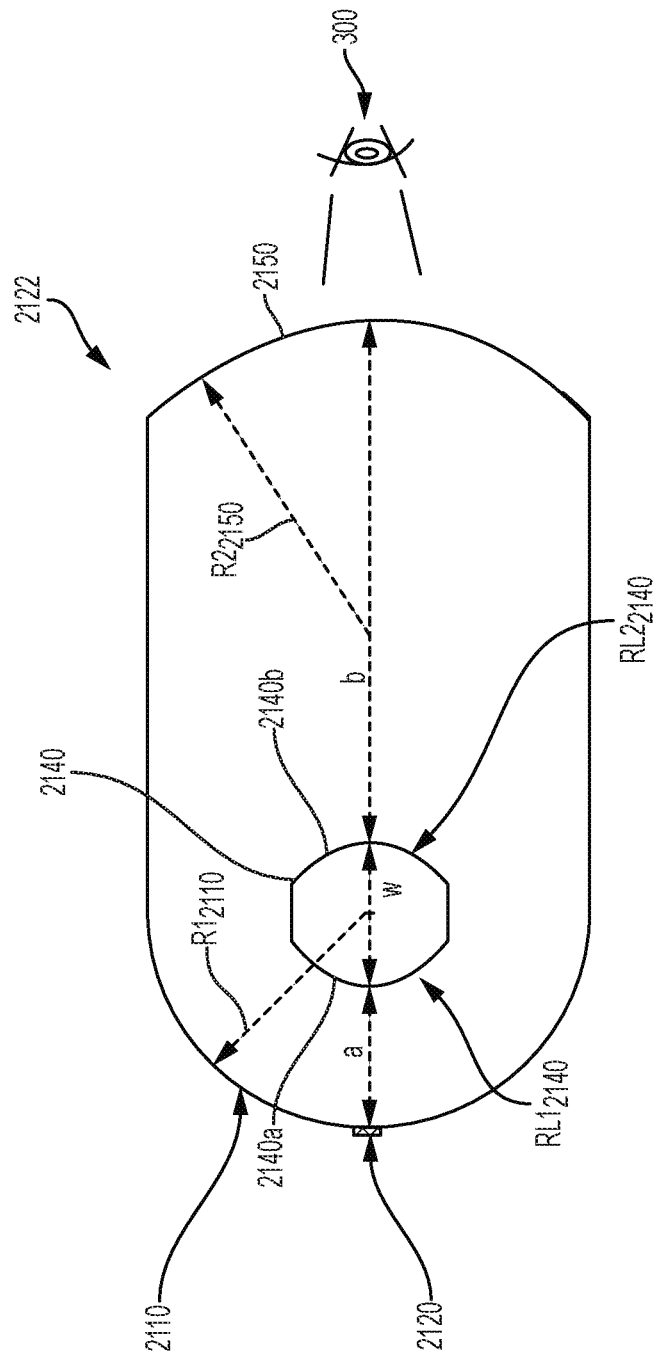
FIG. 52 is a cross-sectional view of the tubing of FIG. 51.

In the illustrated embodiment of FIG. 50, the lens 2050 of tubing 2022 is relatively small. A modified embodiment of tubing 2122 according to the present disclosure is illustrated in FIGS. 51-52. Tubing 2122 has a modified design to both the tubing geometry and the lumen geometry to achieve the magnification optical effect with an increasing viewing angle.

Tubing 2122 of FIG. 52 includes surface 2110 having marker 2120 and a radius of curvature, $R1_{2110}$. The radius of curvature $R1_{2110}$ matches or aligns with the tubing outer circumferential surface, so that the object distance to the rest of the optical system varies less with viewing angle.

Opposite to surface 2110 of tubing 2122 is a primary lens 2150 through which a user's eye 300 views lumen 2140. Lens 2150 has a radius of curvature $R2_{2150}$ and is positioned at distance "b" from lumen 2140, which is chosen so that the effective focal length of the tubing 2122 is positive and greater than or equal to the optical thickness of the tubing 2122 when the lumen 2140 is filled with a higher density medium (i.e. a liquid drug product). The curvature $R2_{2150}$ of lens 2150 is "detuned" so that the tube 2122 does not produce a collimated beam, but rather a slightly diverging bundle of rays.

Lumen 2140 includes surfaces 2140a having a radius curvature $RL1_{2140}$ and 2140b having a radius of curvature $RL2_{2140}$, that are curved to act as a secondary lens and as a field stop to limit the field of view. Because lumen 2140 is surrounded by a higher index material (e.g., plastic), the lumen 2140 will act as a negative lens and modulate the overall effective focal length of the tubing 2122 and the consequent magnification. The secondary lens 2140a, 2140b formed by the lumen 2140 is disposed offset from the center of the tubing 2122 and closer to surface 2210 than the lens 2150, such that a<b. The lumen 2140 is constructed to be symmetric about the center plane (that is, the curvature on either side is identical, but of opposite sign) and convex ($RL1_{2140}=-RL2_{2140}$). The curvature of the lumen walls $RL1_{2140}$ and $RL2_{2140}$ are chosen so that when filled with the lower index material, the total effective focal length of the tubing 2122 becomes negative. Distance "a" is chosen so that the center of the lumen 2140 is approximately coincident with the center of radius of curvature $R1_{2110}$ of surface 2110. The apparent size of the marker 2120, when viewed through the tubing 2122 by a human observer having eye 300, will be about 2.7× larger when the tubing 2122 is in the filled state versus the unfilled state.

It is also within the scope of the present disclosure for lumen 2140 to have an asymmetric curvature, wherein the radii of curvature $RL1_{2140}$ and $RL2_{2140}$ are different. In some embodiments, $RL1_{2140}$ and $RL2_{2140}$ are less than $RL1_{2040}$ of FIG. 47 (where $RL1_{2040}=RL2_{2040}$).

Geometry of tubing 2122 minimizes the difference in path length for the chief ray across the field of view and as the viewing angle is changed. As those of skill in the art would appreciate, a continuum of varying designs balancing magnification against viewing angle may be realized and the example as described in FIGS. 51-52 is non-limiting. Therefore, the designs of FIGS. 47 and 52 and any design therebetween are contemplated by the present disclosure.

VI. Complex Tube Geometries to Enhance Image Differences by Image Translation.

Tubing having complex geometries to cause an image to appear translated differently in space when the lumen is filled with liquid versus unfilled are described in accordance with embodiments of the present disclosure.

Parallel Prism Lumen.

Figure 53:
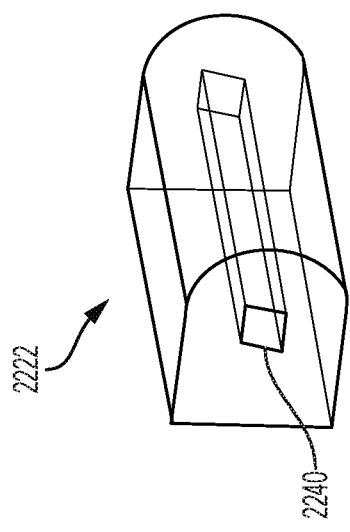
FIG. 53 is a perspective, isometric view of a portion of tubing of the present disclosure having parallel prism lumen geometry.
Figure 54:
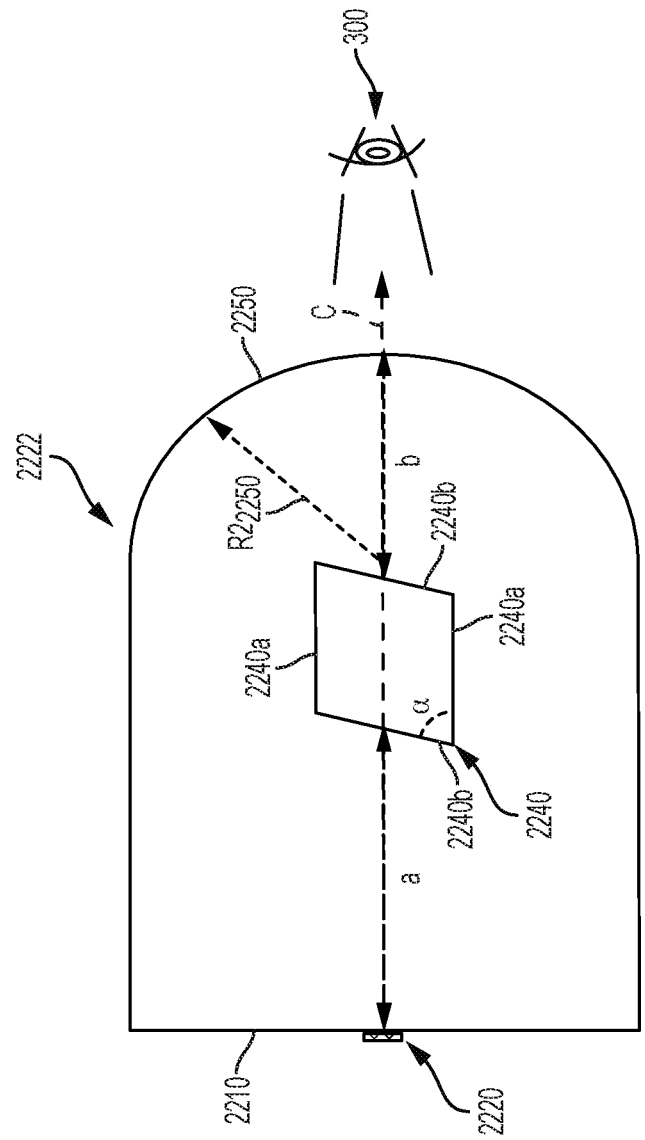
FIG. 54 is a cross-sectional view of the tubing of FIG. 53.

In another exemplary embodiment according to the present disclosure, complex tubing 2222 as illustrated in FIGS. 53-54 utilizes a tubing geometry wherein the cross-section of the lumen 2240 is a parallelogram and the lumen 2240 is configured as a parallelepiped. As shown in perspective, isometric view as in FIG. 53, the tubing 2222 incorporates a primary lens 2250 on at least one side through which a user's eye 300 views lumen 2240. The lens 2250 may be included as part of the tubing 2222 cladding. Surface 2210 includes marker 2220 opposite the lens 2250. Lumen 2240 includes planar surfaces 2240a, which are parallel to optical axis C. Lumen 2240 further includes planar, parallel surfaces 2240b, which are tilted with respect to the optical axis C.

As shown in FIG. 54, surface 2250 has a curvature ($1/R2_{2250}$) and tube thickness ("a" and "b"), which are chosen so that the effective focal length of the tubing 2222 is positive and nearly equal to the optical thickness of the tubing 2222. The focal length is chosen so that a magnified image is presented to the viewer's eye 300. Since the lumen 2240 has no curvature, it displaces the imaging field of view on the marker side 2210 of the tubing 2222 by different amounts depending on whether lumen 2240 is filled or unfilled. Fluids with different indices of refraction will also change the effective object distance and thus the overall magnification. The geometry of tubing 2222 is insensitive to the position of the lumen 2240 inside the tubing, as long as the center of the lumen 2240 is aligned with the transverse optical axis C between the marker 2220 and the vertex of the primary lens 2250. Tubing 2222 transmits an image of marker 2220 that is translated depending on whether lumen 2240 is filled or unfilled.

Figure 55:
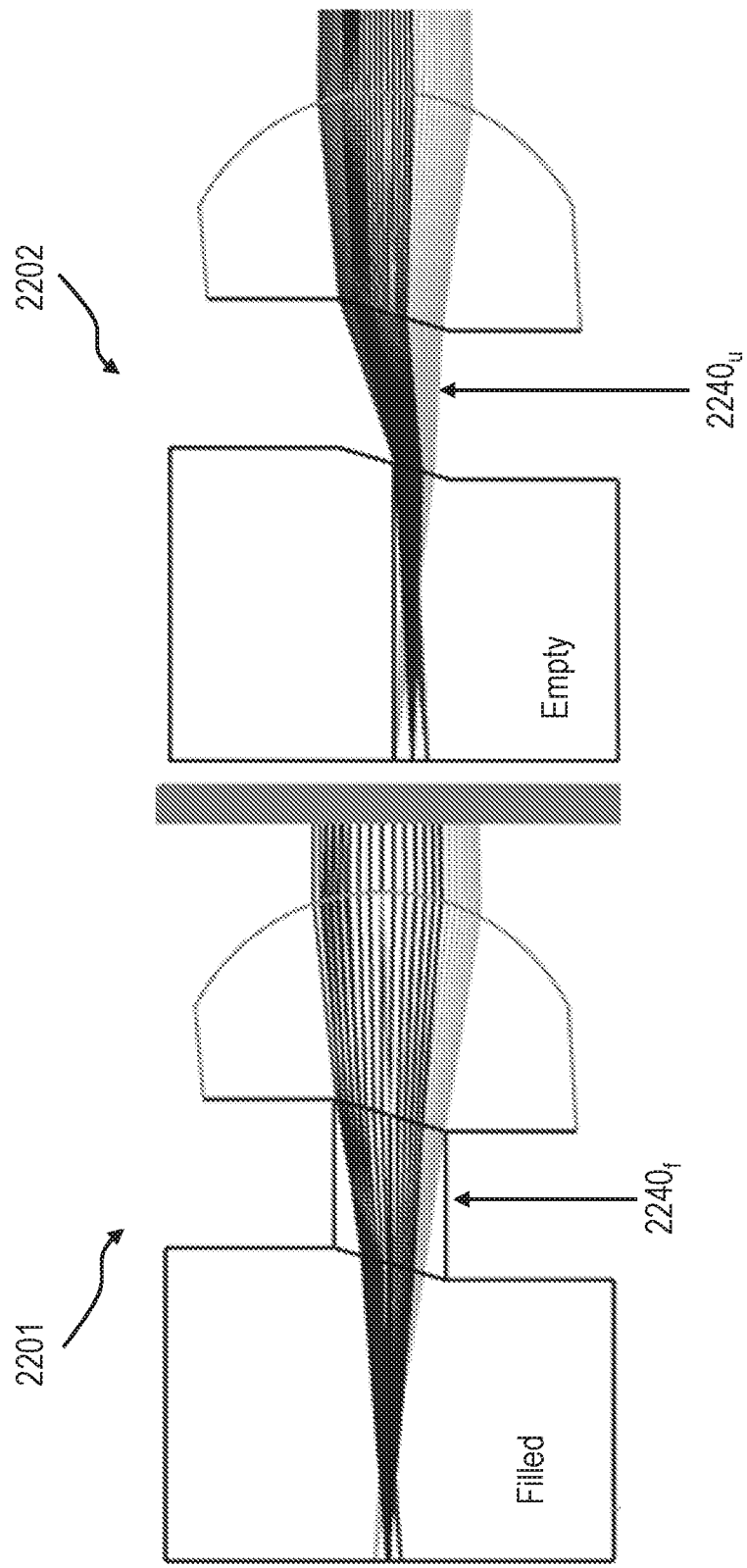
FIG. 55 is a ray-trace schematic of the tubing of FIGS. 54-55 having a lumen in the filled and unfilled condition.

FIG. 55 is a ray-trace diagram of the parallel prism lumen geometry for tubing 2222 of FIGS. 53-54. The ray-trace diagram 2201 (to the left) demonstrates the image formation when the lumen 2240 is filled (2240f) and the ray-trace diagram 2202 (to the right) demonstrates the image formation when the lumen 2240 is unfilled ($2240_n$). The geometry of tubing 2222 also provides differential magnification. The apparent size of the marker 2220, when viewed through the tubing 2222 by a human observer having eye 300, will be about 1.8× larger when the tubing 2222 is in the filled state versus the unfilled state.

Figure 56:
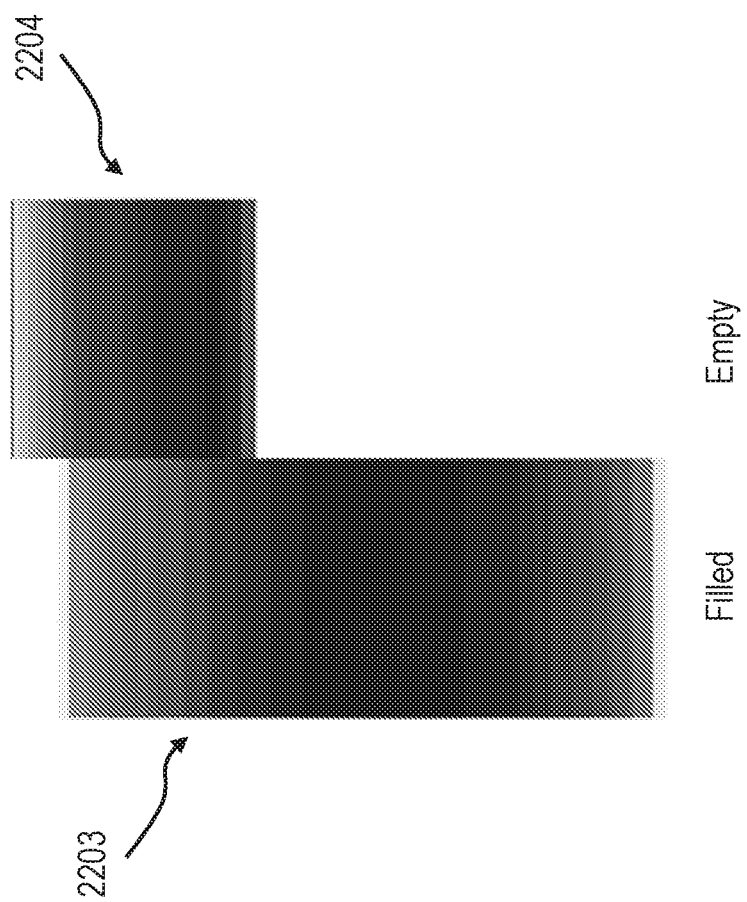
FIG. 56 shows the image translation effect for the tubing having parallel prism lumen geometry as in FIGS. 54-55.

The translation offset between filled and unfilled states is partially dependent upon the width of the marker 2220 of FIG. 54. A marker or stripe centered at the vertex of the surface 2210 of tubing 2222 is expected to produce the images shown in FIG. 56. This composite image is a scale representation; while the scale is arbitrary, the relative size of the images is accurate. FIG. 56 simulates the locations and spatial extent of an imaged object in filled 2203 and empty 2204 states. The simulation is illustrative of predicted translation effects but does not include specular reflections from the lumen 2240, or off-axis paths that bypass the lumen 2240 completely.

Wedge Prism Lumen.

In another exemplary embodiment according to the present disclosure, an alternative embodiment of tubing 2322 having a prismatic lumen 2340 is described. As shown in perspective, isometric view of tubing 2322 of FIG. 57, tubing 2322 includes outer circumferential surface 2305 having marker 2320. Opposite of marker 2320 is surface 2350 of tubing 2322, which is curved to produce a primary cylindrical lens. Lumen 2340 includes two opposing optical surfaces 2340a and 2340b with some separation between them and a non-zero difference in the orientation of the surface normal or "wedge angle". Surface 2340a has a tilt angle $\alpha$ and surface 2340b has a tilt angle $\beta$. Lumen 2340 acts to deflect the chief ray of the optical system, thereby moving the field of view on the object surface depending on whether lumen 2340 is filled or unfilled. Lumen 2340 acts as a field stop. If the lumen 2340 surfaces are also curved, the lumen 2340 may also be used as a field lens.

The wedge prism lumen 2340 allows considerable flexibility in the design of the surrounding marker surface 2305 and primary lens surface 2350. The choice of lateral position, wedge angle(s), and curvature(s) may be optimized to obtain a particular magnification, field of view, and or image quality based on the index difference of the fluids to be used in the lumen 2340. In all cases, a wedge prism lumen 2340 will act to displace the field of view on the marker surface 2305 and alter the effective focal length of the tubing 2322 as a function of the filling fluid, which results in differential image sizes (magnification) and position.

Figure 57:
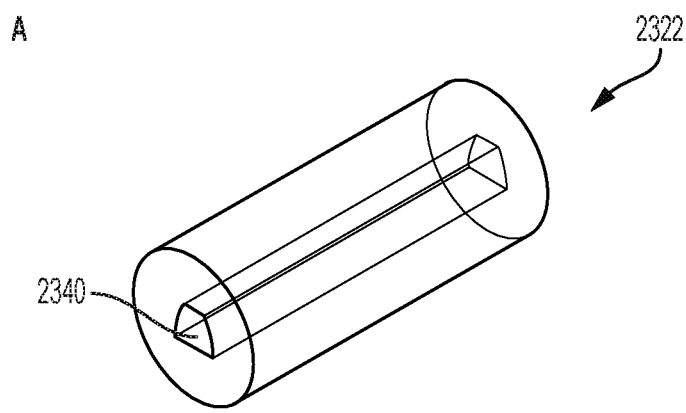
FIG. 57 is a perspective, isometric view of a portion of tubing of the present disclosure having wedge prism lumen geometry.
Figure 58:
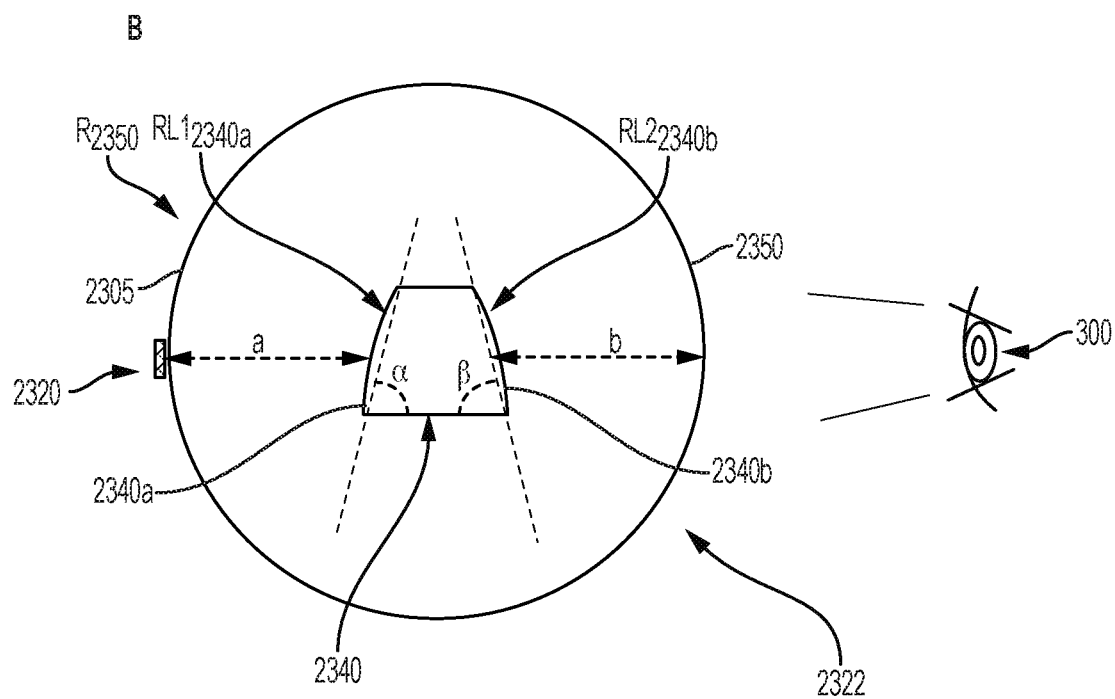
FIG. 58 is a cross-sectional view of the tubing of FIG. 57.
Figure 59:
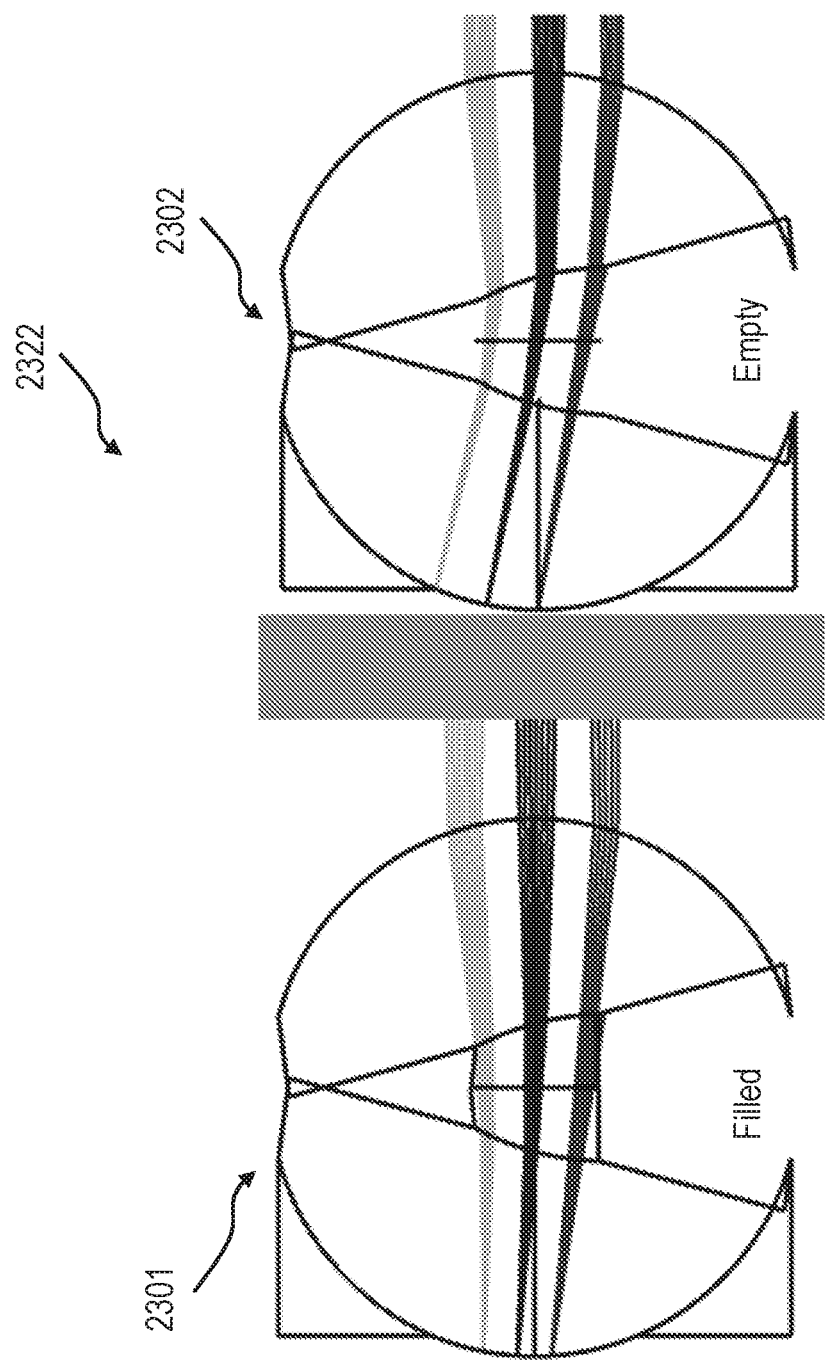
FIG. 59 is a ray-trace schematic of the tubing of FIGS. 57-58 having a lumen in the filled and unfilled condition.

FIG. 59 is a ray-trace diagram of the powered wedge prism lumen 2340 of tubing 2322 of FIGS. 57-58. The ray-trace diagram 2301 (to the left) demonstrates the image formation when the lumen 2340 is filled ($2340f$) and the ray-trace diagram 2302 (to the right) demonstrates the image formation when the lumen 2340 is unfilled ($2340_n$). In this design, lumen 2340 is centered in a cylindrical tubing 2322 (a=b). Lumen 2340 is constructed as a symmetric wedge prism with curved surfaces 2340a and 2340b having equal and opposite tilt angles, such that $\alpha=-\beta$, and equal and opposite radii of curvature, such that $RL1_{2340a}=-RL2_{2340b}$.

Figure 60:
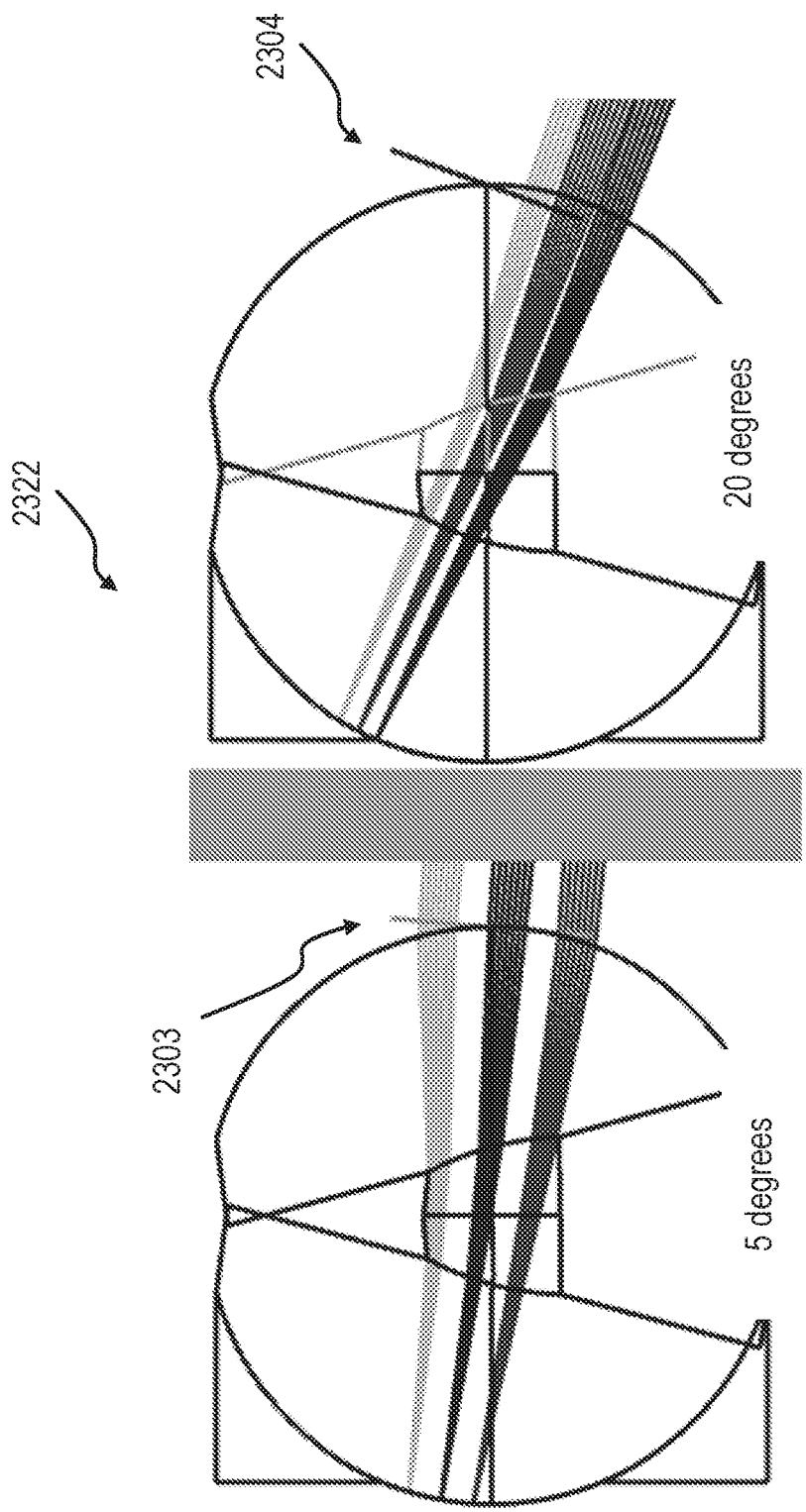
FIG. 60 is a ray-trace schematic of the tubing of FIGS. 57-58 wherein the viewing angle is offset by 5 degrees and 20 degrees.

FIG. 60 shows ray-trace diagrams with a 5° viewing angle 2303 (to the left) and a 20° viewing angle 2304 (to the right) for the filled lumen 2340 of FIG. 59. These diagrams show that the differential magnification, image quality, and relative shearing offset remains approximately the same for these off-axis viewing angles. It is noted that in the diagrams of FIGS. 59-60, only rays on the top portion of the cross-section are shown; it is understood that the mirror-image of the rays could be shown on the bottom portion of the cross-section.

Figure 61:
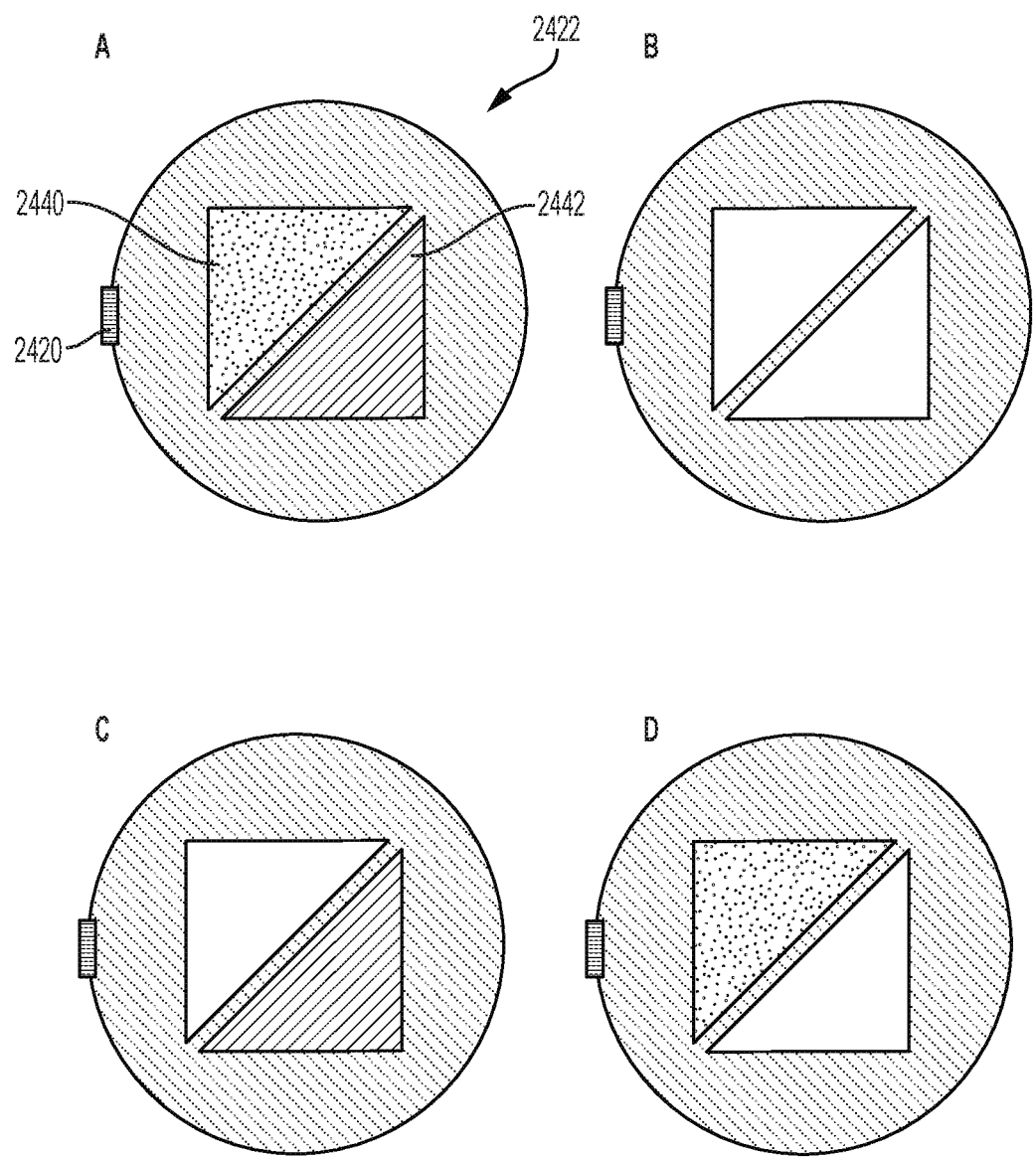
FIG. 61 is a cross-sectional view of tubing of the present disclosure having multiple lumens, as shown in four conditions: (A) first and second lumens are filled; (B) first and second lumens are unfilled; (C) the first lumen is unfilled and the second lumen is filled; and (D) the first lumen is filled and the second lumen is unfilled.

Multi-Lumen Tubing. In another exemplary embodiment according to the present disclosure, tubing having multiple lumens is described. Tubing having more than one lumen are manufacturable, i.e. by extrusion, and are useful in delivering multiple drug products through infusion tubing. In one non-limiting example, to prevent both hyper- and hypo-glycemia in patients with diabetes, it is desirable to have both insulin and the hormone glucagon available as an infusion within single tubing delivery systems. An exemplary double-lumen tubing 2422 is shown in FIG. 61 and includes a first lumen 2440, a second lumen 2442, and a marker 2420. The marker 2420 may enable the user to discern between the following four conditions: (A) the first and second lumens 2440, 2442 are filled; (B) the first and second lumens 2440, 2442 are unfilled; (C) the first lumen 2440 is unfilled and the second lumen 2442 is filled; and (D) the first lumen 2440 is filled and the second lumen 2442 is unfilled. Each of the four conditions (A)-(D) gives rise to a discernable visual image. As with previous examples according to the present disclosure, the index of refraction associated with the media within each lumen 2440, 2442 and the difference between that index of refraction and that of the tubing 2422 material, each condition results in different optical ray propagation utilizing magnification and/or reflections at the cladding/lumen interface.

Figure 62:
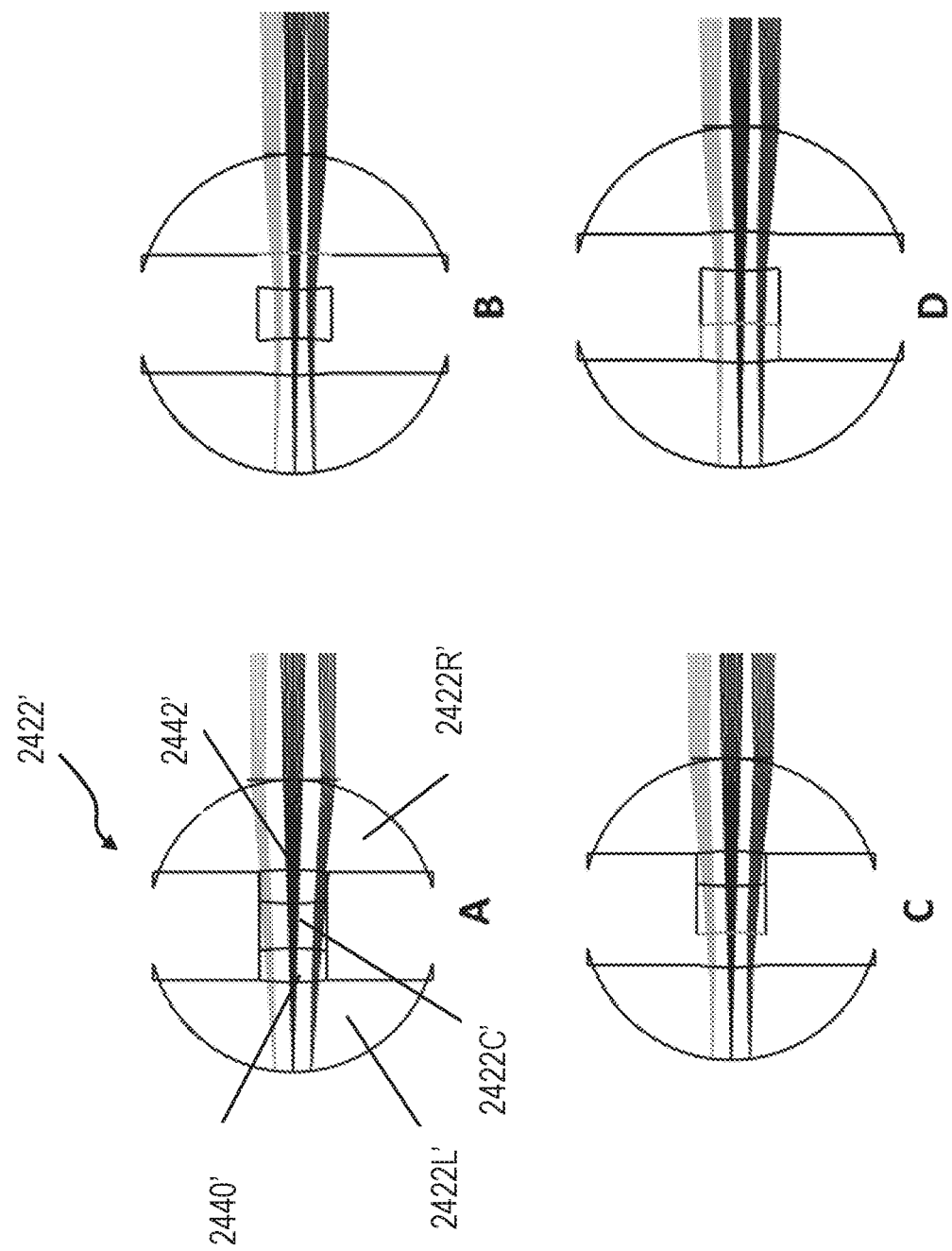
FIG. 62 show ray-trace schematics for the tubing of FIG. 62 in the four conditions: (A) first and second lumens are filled; (B) first and second lumens are unfilled; (C) the first lumen is unfilled and the second lumen is filled; and (D) the first lumen is filled and the second lumen is unfilled.

Any of the embodiments of the present disclosure as described above may be adapted to employ more than one lumen. In one example, and as shown in FIG. 62, a double-lumen tubing 2422' having two identical lumens 2440', 2442' positioned symmetrically about the longitudinal axis of the tubing 2422' is constructed according to the parameters of Table 2 below.

TABLE 2

Double-Lumen Tubing Parameters

| Element | Radius | Thickness | Material |
| --- | --- | --- | --- |
| Left tubing portion 2422L' | 0.032 | 0.020 | Polyurethane |
| First lumen 2440' | 0.060 | 0.0075 | Fluid |
| Central tubing portion 2422C' | −0.060 | 0.0100 | Polyurethane |
| Second lumen 2442' | 0.060 | 0.0075 | Fluid |
| Right tubing portion 2422R' | −0.060 | 0.020 | Polyurethane |

Ray-trace diagrams for the double-lumen tubing 2422' described in Table 2 are shown in FIG. 62 for the following four conditions: (A) the first and second lumens 2440', 2442' are filled; (B) the first and second lumens 2440', 2442' are unfilled; (C) the first lumen 2440' is unfilled and the second lumen 2442' is filled; and (D) the first lumen 2440' is filled and the second lumen 2442' is unfilled. Each of the four conditions (A)-(D) gives rise to a unique field of view and magnification, as summarized in Table 3 below. The field points are chosen near the limit of the field of view.

TABLE 3

Double-Lumen Tubing Magnification and Field of View

| First Lumen 2440' | Second Lumen 2442' | Relative Magnification | Field of View (obj. space, mils) |
| --- | --- | --- | --- |
| Filled | Filled | 1.7× | 4 |
| Filled | Empty | 1.2× | 6 |
| Empty | Filled | 1.4× | 5 |
| Empty | Empty | 1.0× | 7 |

Figure 63:
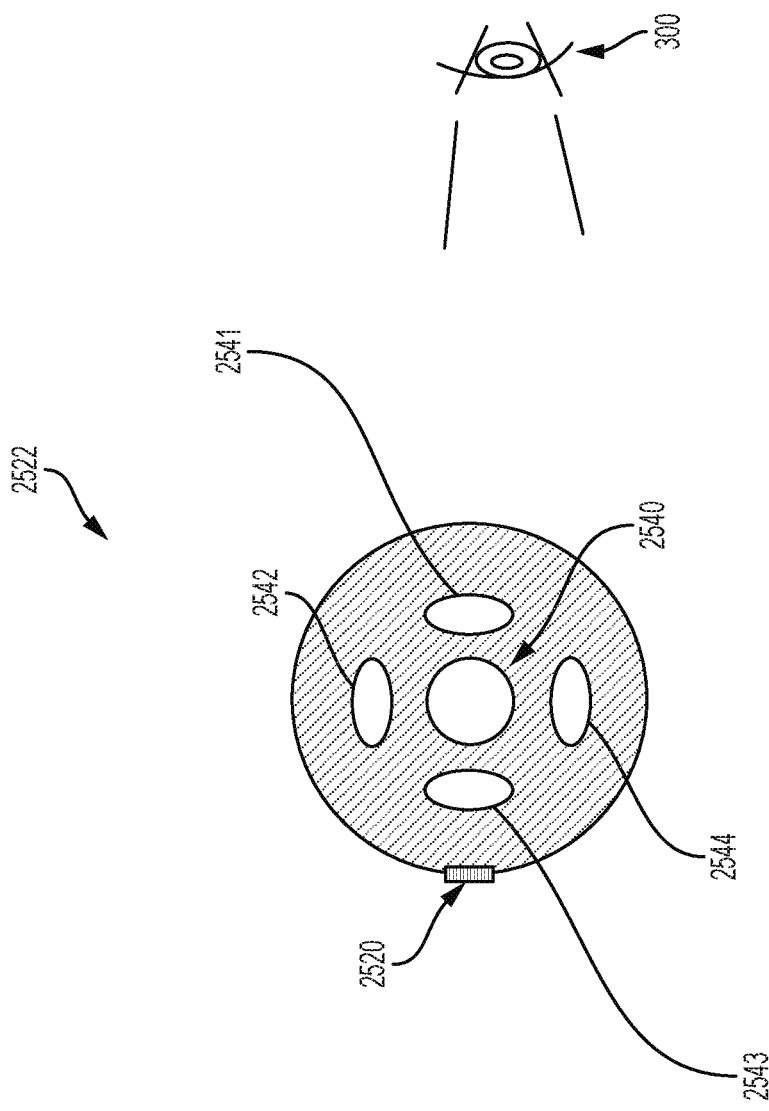
FIG. 63 is a cross-sectional view of tubing of the present disclosure having multiple lumens for serving as optical elements that can steer, shape, or focus a beam of light.

Another multi-lumen tubing 2522 is shown in FIG. 63. Tubing 2522 includes lumen 2540 for carrying a liquid drug product, for example, and additional lumens 2541, 2542, 2543, and 2544, which are unfilled. The additional lumens 2541, 2542, 2543, and 2544, may serve as optical elements that can steer, shape, or focus a beam of light, such as that used to image marker 2520.

Other tubing geometries including non-cylindrical tubing, multiple lumens including those with non-cylindrical lumen geometries, and symmetrical or asymmetrical patterns of markers may be used in accordance with the concepts of the present disclosure. Tubing geometries may be further optimized to provide greater discrimination between the conditions using the optimization methods as described in the present disclosure.

Multi-Filament Tubing.

Figure 64:
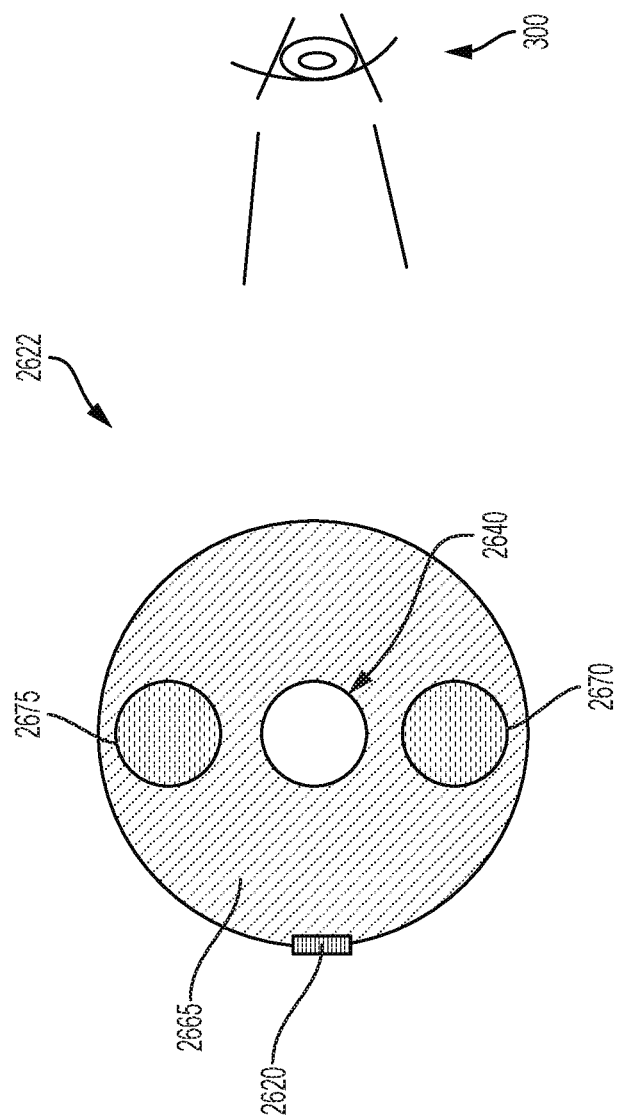
FIG. 64 is a cross-sectional view of tubing of the present disclosure having multiple filaments so that light rays may be further steered or shaped to provide discernable images for visualization.

Filaments of different materials may be integrated into a tubing according to other embodiments of the present disclosure. By including multiple filaments, light rays may be further steered or shaped to provide discernable images for visualization. As shown in FIG. 64, tubing 2622 includes lumen 2640 for carrying a liquid medium and marker 2620 for use in forming an image for visualization by user's eye 300. Tubing 2622 also includes multiple filaments 2670 and 2675 made of a different material than the tubing wall 2665. The materials of filaments 2670 and 2675 may be the same or different. The materials of tubing wall 2665 and filaments 2670 and 2675 may all be made of plastic, for example. However, filaments 2670 and 2675 may be made of different plastics than tubing wall 2665 which are selected to absorb certain wavelengths of light at certain portions of the tubing 2622. Filaments 2670 and 2675 may be coextruded with the transparent tubing wall 2665 to form tubing 2622. Filaments 2670 and 2675 may be used to mask or eliminate the secondary images as described in the present disclosure and as shown in FIGS. 23-25. For example, filaments 2670 and 2675 may be opaque to absorb all visible light. Alternatively, filaments 2670 and 2675 may be made of material to absorb only certain wavelengths of the visible spectrum.

The infusion sets described herein may further comprise a drug. In another embodiment, a system may comprise one or more devices including the infusion set and a drug. The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of transport or delivery by the infusion set. The drug as used in the infusion set may be formulated with one or more excipients. The infusion set is operated in a manner generally as described above by a patient, caregiver or healthcare professional to deliver drug to a person.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A transparent tubing, the transparent tubing comprising:
    a longitudinal axis having a center;
    an inner circumferential surface disposed at a first radial distance (r1) from the center and defining a fluid pathway therethrough for delivering a liquid having a first index of refraction $n_1$;
    an outer circumferential surface disposed at a second radial distance (r2) from the center;
    a wall extending between the inner circumferential surface and the outer circumferential surface;
    a plurality of markers including at least one visual marker applied to, etched onto, or embedded in the wall and comprising at least one of a word, a symbol, a stripe, and a pattern, wherein the plurality of markers are disposed radially about the tubing and further include at least one masking marker configured to inhibit a secondary image effect of the at least one visual marker; and,
    at least one integrated lens disposed opposite the longitudinal axis from the at least one visual marker, the at least one integrated lens configured to direct light from the at least one visual marker for detecting a presence or an absence in the fluid pathway of air having a second index of refraction $n_2$, wherein the second index of refraction $n_2$ is different from the first index of refraction $n_1$.

2. The transparent tubing of claim 1, the at least one integrated lens further comprising an exterior surface including at least one point coincident with the outer circumferential surface, wherein the exterior surface of the at least one integrated lens protrudes from the outer circumferential surface, and wherein the exterior surface of the lens includes at least one point at a third radial distance ($r_3$) from the center, wherein the third radial distance ($r_3$) is greater than the second radial distance ($r_2$).

3. The transparent tubing of claim 2, wherein the exterior surface of the lens is convex.

4. The transparent tubing of claim 2, wherein the outer circumferential surface has a first radius of curvature ($R_1$) and the exterior surface of the lens has a second radius of curvature ($R_2$), wherein the first radius of curvature ($R_1$) and the second radius of curvature ($R_2$) are different.

5. The transparent tubing of claim 2, wherein the outer circumferential surface has a first radius of curvature ($R_1$) and the exterior surface of the lens has a second radius of curvature ($R_2$), wherein the first radius of curvature ($R_1$) is greater than the second radius of curvature ($R_2$).

6. The transparent tubing of claim 2, wherein the outer circumferential surface has a first radius curvature ($R_1$) and the exterior surface of the lens has a plurality of radii of curvature ($R_{2-5}$).

7. The transparent tubing of claim 2, wherein the outer circumferential surface and the exterior surface of the lens meet at first and second edges.

8. The transparent tubing of claim 2, wherein the outer circumferential surface is connected to the exterior surface of the lens by first and second planar faces.

9. The transparent tubing of claim 8, wherein the first planar face is inclined at a first slope and the second planar face is inclined at a second slope, wherein the first slope is opposite the second slope.

10. The transparent tubing of claim 1, wherein the integrated lens includes an exterior surface connected to the outer circumferential surface by first and second coplanar faces, wherein the exterior surface of the lens includes at least one point at a third radial distance ($r_3$) from the center, wherein the third radial distance ($r_3$) is greater than the first radial distance ($r_1$).

11. The transparent tubing of claim 1, wherein the integrated lens is aspheric.

12. The transparent tubing of claim 1, wherein the transparent tubing is a material chosen from at least one of polypropylene, polyvinyl chloride, polyethylene, polyurethane, silicone, and glass.

13. The transparent tubing of claim 1, wherein the transparent tubing including the integrated lens is formed in a single extrusion process.

14. The transparent tubing of claim 1, wherein the integrated lens comprises a plurality of plano-convex lenses disposed linearly and parallel to the longitudinal axis.

15. The transparent tubing of claim 1, wherein the integrated lens is an elongated cylindrical lens disposed parallel to the longitudinal axis.

16. The transparent tubing of claim 1, wherein the integrated lens further includes an interior surface protruding from the inner circumferential surface at a radial distance from the center, wherein the radial distance of the interior surface from the center is less than the first radial distance ($r_1$).

17. The transparent tubing of claim 1, the at least one integrated lens having a third index of refraction $n_3$, wherein $n_3$ is different from $n_1$ and $n_2$.

18. The transparent tubing of claim 17, the wall having a fourth index of refraction $n_4$, wherein $n_4$ and $n_3$ are the same or different.

19. The transparent tubing of claim 18, wherein the wall is made of glass or plastic.

20. The transparent tubing of claim 1, wherein the inner circumferential surface has a conic section cross-sectional shape.

21. The transparent tubing of claim 1, wherein the inner circumferential surface has a polygonal cross-sectional shape.

22. The transparent tubing of claim 1, wherein the transparent tubing is a transparent infusion-set tubing for an insulin pump.

23. The transparent tubing of claim 1, wherein the fluid pathway defined by the inner circumferential surface has a radius $R_L$, and the at least one visual marker has a width of about $0.25R_L$ to about $0.90R_L$.

24. The transparent tubing of claim 1, wherein the at least one visual marker includes a stripe disposed longitudinally along the outer circumferential surface.

25. The transparent tubing of claim 1, wherein the plurality of markers includes a radially symmetric pattern wherein each marker is disposed radially and symmetrically about the tubing.

26. The transparent tubing of claim 25, wherein the plurality of markers includes differently-colored parallel longitudinal stripes.

27. The transparent tubing of claim 1, wherein the plurality of markers includes a radially asymmetric pattern wherein each marker is disposed radially and non-uniformly about the tubing.

* * * * *